US008097612B2

(12) United States Patent
Glick

(10) Patent No.: US 8,097,612 B2
(45) Date of Patent: Jan. 17, 2012

(54) COMPOSITIONS AND METHODS RELATING TO NOVEL COMPOUNDS AND TARGETS THEREOF

(75) Inventor: Gary D. Glick, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 335 days.

(21) Appl. No.: 12/303,272

(22) PCT Filed: Jun. 8, 2007

(86) PCT No.: PCT/US2007/013576
§ 371 (c)(1),
(2), (4) Date: May 1, 2009

(87) PCT Pub. No.: WO2007/146167
PCT Pub. Date: Dec. 21, 2007

(65) Prior Publication Data
US 2010/0004227 A1    Jan. 7, 2010

Related U.S. Application Data

(60) Provisional application No. 60/812,270, filed on Jun. 9, 2006.

(51) Int. Cl.
*C07D 243/12* (2006.01)
*A61K 31/55* (2006.01)
(52) U.S. Cl. .................................. 514/221; 540/504
(58) Field of Classification Search .................. 540/504; 514/221
See application file for complete search history.

(56) References Cited

U.S. PATENT DOCUMENTS

| | | |
|---|---|---|
| 3,261,828 A | 7/1966 | Uskokovic |
| 3,374,264 A | 3/1968 | Uskokovic |
| 3,384,635 A | 5/1968 | Calabateas |
| 3,415,814 A | 12/1968 | Calabeteas |
| 3,847,905 A | 11/1974 | Bub |
| 4,076,823 A | 2/1978 | Wade |
| 4,088,756 A | 5/1978 | Voorhees |
| 4,108,852 A | 8/1978 | Bub |
| 4,110,337 A | 8/1978 | Szarvasi |
| RE30,293 E | 6/1980 | Bub |
| 4,495,101 A | 1/1985 | Klaubert |
| 4,551,480 A | 11/1985 | Stiefel |
| 4,560,684 A | 12/1985 | Sugasawa |
| 4,623,646 A | 11/1986 | Casals-Stenzel |
| 4,751,223 A | 6/1988 | Glamkowski |
| 4,820,834 A | 4/1989 | Evans |
| 4,894,366 A | 1/1990 | Okuhara |
| 4,898,861 A | 2/1990 | Morgan |
| 4,916,138 A | 4/1990 | Ueda |
| 4,929,611 A | 5/1990 | Okuhara |
| 4,946,778 A | 8/1990 | Ladner |
| 5,004,741 A | 4/1991 | Evans |
| 5,041,438 A | 8/1991 | Hsu |
| 5,141,930 A | 8/1992 | Nakao |
| 5,147,872 A | 9/1992 | Golwyn |
| 5,216,148 A | 6/1993 | Klaus |
| 5,288,514 A | 2/1994 | Ellman |
| 5,324,726 A | 6/1994 | Bock |
| 5,391,566 A | 2/1995 | Chakravarty |
| 5,444,092 A | 8/1995 | Collins |
| 5,521,170 A | 5/1996 | Setoi |
| 5,545,568 A | 8/1996 | Ellman |
| 5,559,230 A | 9/1996 | Ogawa |
| 5,591,227 A | 1/1997 | Dinh |
| 5,597,915 A | 1/1997 | Chambers |
| 5,599,352 A | 2/1997 | Dinh |
| 5,633,251 A | 5/1997 | Claremon |
| 5,677,282 A | 10/1997 | Oleksyszyn |
| 5,697,967 A | 12/1997 | Dinh |
| 5,763,437 A | 6/1998 | Sato |
| 5,776,946 A | 7/1998 | McGeer |
| 5,861,380 A | 1/1999 | Gyorkos |
| 5,962,337 A | 10/1999 | Ohlmeyer |
| 6,004,942 A | 12/1999 | Firestein |
| 6,074,859 A | 6/2000 | Hirokawa |
| 6,080,588 A | 6/2000 | Glick |
| 6,100,254 A | 8/2000 | Budde |
| 6,239,131 B1 | 5/2001 | Shinozaki |
| 6,277,844 B1 | 8/2001 | Spector |
| 6,319,931 B1 | 11/2001 | Kroemer |
| 6,506,744 B1 | 1/2003 | Alig |
| 6,524,623 B1 | 2/2003 | Hodosh |
| 6,524,832 B1 | 2/2003 | Kufe |
| 6,579,854 B1 | 6/2003 | Mitchell |

(Continued)

FOREIGN PATENT DOCUMENTS
CA        2457405        2/2003
(Continued)

OTHER PUBLICATIONS

International Search Report, International Patent Application No. PCT/US04/013455 dated Jan. 6, 2006. European Search Report, EP Patent Application No. 03 027 484.9-2117 dated May 3, 2004.
European Search Report, EP Patent Application No. 04 775 923.8-2123 dated Nov. 9, 2007.
European Search Report, EP Patent Application No. 00 928 586.7-2117 dated Apr. 23, 2002.
European Search Report, EP Patent Application No. 05 769 345.9 dated Oct. 22, 2007.
International Search Report, PCT/US2006/042753, dated May 6, 2008.
Written Opinion of the International Searching Authority, PCT/US06/21561, dated Aug. 17, 2007.
International Preliminary Report on Patentability, PCT/US2006/041446, mailed May 8, 2008.
International Search Report and Written Opinion, PCT/US2006/00442, mailed May 12, 2006.
International Report on Patentability, PCT/US2006/000442 mailed Jul. 12, 2007.

(Continued)

*Primary Examiner* — Bruck Kifle
(74) *Attorney, Agent, or Firm* — Casimir Jones SC

(57) ABSTRACT

The present invention relates to novel chemical compounds, methods for their discovery, and their therapeutic use. In particular, the present invention provides benzodiazepine derivatives and related compounds and methods of using benzodiazepine derivatives and related compounds as therapeutic agents to treat a number of conditions associated with the faulty regulation of the processes of programmed cell death, autoimmunity, inflammation, hyperproliferation, and the like.

16 Claims, No Drawings

U.S. PATENT DOCUMENTS

| | | |
|---|---|---|
| 6,605,593 B1 | 8/2003 | Naicker |
| 6,613,739 B1 | 9/2003 | Naicker |
| 6,767,533 B1 | 7/2004 | Casellas |
| 6,824,561 B2 | 11/2004 | Soykan |
| 6,916,813 B2 | 7/2005 | Atwal et al. |
| 7,125,866 B1 | 10/2006 | Glick |
| 7,144,880 B2 | 12/2006 | Glick |
| 7,150,433 B2 | 12/2006 | Healy |
| 7,175,953 B2 | 2/2007 | Licha |
| 7,220,739 B2 | 5/2007 | Glick |
| 7,250,410 B2 | 7/2007 | Bourguignon |
| 7,276,348 B2 | 10/2007 | Glick |
| 7,351,241 B2 | 4/2008 | Bendett |
| 7,572,788 B2 | 8/2009 | Glick |
| 7,638,624 B2 | 12/2009 | Glick |
| 7,683,046 B2 | 3/2010 | Glick |
| 7,851,465 B2 | 12/2010 | Glick |
| 2002/0025946 A1 | 2/2002 | Buchanan |
| 2002/0048566 A1 | 4/2002 | El-Deiry |
| 2002/0128208 A1 | 9/2002 | Snyder |
| 2003/0044776 A1 | 3/2003 | Dykens |
| 2003/0119029 A1 | 6/2003 | Glick |
| 2004/0009972 A1 | 1/2004 | Ding |
| 2004/0087489 A1 | 5/2004 | Ruiz |
| 2004/0157833 A1 | 8/2004 | Harris |
| 2004/0176358 A1 | 9/2004 | Glick |
| 2005/0113460 A1 | 5/2005 | Glick |
| 2005/0261176 A1 | 11/2005 | Glick |
| 2005/0272723 A1 | 12/2005 | Glick |
| 2006/0025388 A1 | 2/2006 | Glick |
| 2006/0052369 A1 | 3/2006 | Glick |
| 2006/0166975 A1 | 7/2006 | Glick |
| 2007/0036854 A1 | 2/2007 | Glick |
| 2007/0043033 A1 | 2/2007 | Glick |
| 2007/0105844 A1 | 5/2007 | Glick |
| 2007/0111994 A1 | 5/2007 | Glick |
| 2007/0135418 A1 | 6/2007 | Glick |
| 2007/0299059 A1 | 12/2007 | Glick |
| 2008/0064686 A1 | 3/2008 | Durrani |

FOREIGN PATENT DOCUMENTS

| | | |
|---|---|---|
| CA | 2372150 | 11/2007 |
| DE | 1810423 | 10/1969 |
| EP | 0 349 949 | 1/1990 |
| EP | 0227539 | 5/1990 |
| EP | 0 906 907 | 7/1999 |
| EP | 1143946 | 10/2001 |
| EP | 1423122 | 2/2003 |
| EP | 1398033 | 3/2004 |
| EP | 1398033 | 6/2004 |
| EP | 1622684 | 2/2006 |
| EP | 1742460 | 7/2006 |
| EP | 1778204 | 5/2007 |
| EP | 1786429 | 5/2007 |
| EP | 1845996 | 10/2007 |
| GB | 1363735 | 8/1974 |
| RU | 2096044 | 11/1997 |
| WO | 90/05305 | 5/1990 |
| WO | 90/13332 | 11/1990 |
| WO | 91/12779 | 9/1991 |
| WO | 92/01683 | 2/1992 |
| WO | 94/08234 | 4/1994 |
| WO | 97/01560 | 1/1997 |
| WO | 97/30992 | 8/1997 |
| WO | 98/14192 | 4/1998 |
| WO | 98/57161 | 12/1998 |
| WO | 99/19306 | 4/1999 |
| WO | 99/29347 | 6/1999 |
| WO | 99/58117 | 11/1999 |
| WO | 99/66958 | 12/1999 |
| WO | 99/67220 | 12/1999 |
| WO | 00/19200 | 6/2000 |
| WO | 00/66106 | 11/2000 |
| WO | 01/51922 | 7/2001 |
| WO | 02/67988 | 9/2002 |
| WO | 02/098865 | 12/2002 |
| WO | 03/015703 | 2/2003 |
| WO | 03/014658 | 5/2003 |
| WO | 03/045901 | 6/2003 |
| WO | 03/050261 | 6/2003 |
| WO | 03/106628 | 12/2003 |
| WO | 2005/004988 | 1/2005 |
| WO | 2006/014526 | 2/2006 |
| WO | 2006/029245 | 3/2006 |
| WO | 2006/073448 | 7/2006 |
| WO | 2006/074358 | 7/2006 |
| WO | 2006/053193 | 5/2007 |
| WO | 2007/050587 | 5/2007 |
| WO | 2007/053725 | 5/2007 |
| WO | 2007/146167 | 12/2007 |
| WO | 2008/012553 | 9/2008 |
| WO | 2008/116156 | 9/2008 |
| WO | 2008/133635 | 11/2008 |
| WO | 2009/061916 | 5/2009 |

OTHER PUBLICATIONS

Puodziunaite, B., et al., "Bromination of Aromatic Ring of Tetrahydro-1,5-Benzodiazepin-2-Ones", Chemistry of Heterocyclic Compounds, vol. 36, No. 6, 2000.
AU Patent App. No. 2005323519 dated Nov. 27, 2007.
EP Search, EP Patent App. No. 03 027 484.9-2117, dated Jan. 31, 2005.
Canadian Patent Search, CA Patent Application No. 2,457,405, dated Feb. 6, 2007.
Wolvetang, et al., FEBS Letters (1994), 339, 40-44.
Nawrocka, et al., Arch. Pharm. (Weinheim) Jan. 2001, 334(1), 3-10.
International Search Report and Written Opinion, PCT/US08/56231, mailed Jun. 24, 2008.
International Search Report and Written Opinion, PCT/US05/14463, mailed Dec. 4, 2006.
International Search Report and Written Opinion, PCT/US07/11422, mailed Nov. 15, 2007.
International Search Report and Written Opinion, PCT/US07/13576, mailed Nov. 23, 2007.
International Search Report, PCT/US06/042753, mailed Apr. 19, 2007.
Desjardins, P. and Stephanie Ledoux, "The Role of Apoptosis in Neurodegenerative Disease," Metabolic Brian Disease, vol. 13, No. 2, pp. 79-96 (1998).
International Search Report, PCT/US06/41446, mailed Aug. 1, 2007.
Godic, "New approaches to psoriasis treatment. A review." 2004. Acta Dermatoven APA, vol. 13, No. 2, pp. 50-57.
Bisaha, S.N., et al., A switch in enantiomer preference between mitochondrial F1F0-ATPase chemotypes, Bioorganic & Medicinal Chemistry Letters, 2005 15(11), pp. 2749-2751.
International Search Report and Written Opinion dated Mar. 27, 2009, PCT/US2008/076021.
Chinese Office Action, CN Patent Application No. 200580029827.4, dated Apr. 17, 2009.
Gupta et al., "Psychitripic drugs in dermatology . . . " Database:EMbase (AN:86111413), Journal of the American Academy of Dermatology, 1986, vol. 14, No. 4, pp. 633-645.
Lowe, "Systemic treatment of severe psoriasis," The New England Journal of Medicine, 324 (5), Feb. 7, 1991, pp. 333-334.
Laupacis, et al., "Cyclosporin A: a powerful immunosuppressant", CMA Journal, May 1, 1982, vol. 126, pp. 1041-1046.
Otto, M.W., et al. (2005) J. Clin. Psychiatry 66 Suppl. 2:34-38.
Yoshi, M., et al., (2005) Nippon Yakurigaku Zasshi 125(1):33-36.
Yasuda, K., (2004) Nippon Rinsho. 62 Suppl. 12:360-363.
Dacaudin, D. (2004) 15(8):737-745.
Bonnot, O., et al., (2003) Encephale. 29(6):553-559.
International Search Report and Written Opinion, PCT/US2008/082629, mailed Jun. 1, 2009.
Lacapere, J.J., et al. (2003) Steroids 68(7-8):569-585.
Galiegue, S., et al. (2003) Curr. Med. Chem (10(16):1563-1572.
Papadopoulo, V. (2003) Ann. Pharm. Fr. 61(1):30-50.
Goethals, I., et al. (2003) Eur. J. Nucl. Med. Mol. Imaging 30(2):325-328.
Casedo, M., et al. (2002) J. Exp. Med. 196(9):1121-1125.
Buffett-Jerrott S.E. et al. (2002) Curr. Pharm. Des. 8(1):45-58.
Smyth, W.F., et al. (1998) Electrophoresis 19(16-17):2870-2882.

Yoshii, M., et al. (1998) Nihon Shinkeo Seishin Yakurigaku Zasshi, 18(2):49-54.
Varani, J., et al., "A Novel Benzodiazepine Selectively Inhibits Keratinocyte Proliferation . . . ", The Journal of Pharmacology and Experimental Therapeutics, 2005, vol. 313, No. 1, pp. 56-63.
Varani, J., et al. (2001), J. Invest. Dermatol., 117:1335-1341.
Varani, et al., (1994), J. Clin. Invest., 94:1747-1753.
Griffith, C.E., Br. J. Dermatol., 2001, Apr.; 144(4):679-81.
Stern, R.S. (1995), dERMATOL. cLIN. 13:717-722.
Fry, L (1988), Brit. J. Dermatol., 119:445-461.
Krueger GC, et al., (1984), J. Am. Acad. Dermatol., 11:937-947.
AU Patent Application No. 2006203946 Examiner's Report dated Sep. 10, 2008.
EP Search, EP Patent Application No. 05856659, mailed Dec. 9, 2008.
Iiangumaran, et al., "CD44 Selectively Associates with Active Src Family Protein Tyrosine Kinases Lck and Lyn in Glycosphingolipid-Rich . . . ", Blood, vol. 91, No. 10 (May 15, 1998), pp. 3901-3908.
Sato, et al., "CD22 negatively and positively regulates signal transduction through the B lymphocyte antigen receptor," seminars in Immunology, vol. 10, 1998, pp. 287-297.
Joshi, et al., "Oligomycin Sensitivey-conferring Protein (OSCP) of Mitochodrial ATP Synthase," The Journal of Biological Chemistry, vol. 267, No. 18,m Issue of Jun. 25, pp. 12860-12867, 1992.
Giuseppe Piedimonte, et al., "Association of Tyrosine Protein Kinase Activity With Mitochondria in Human Fibroblasts," Journal of Cellular Biochemistry 32:113-123 (1986).
EP Search, EP Patent Application No. 04 775 923.8, dated Dec. 15, 2008.
Appleby, et al., "Murine chronic graft-versus-host disease as a model of osystemic lupus erythematosus: effect of immunosuppressive drugs on disease development," Clin. Exp. Immunol. (1989) 78, 449-453.
Bastian, et al., "Casein Interference in Bovine Plasmin Assays Using a Synthetic Substrate," (1991) J Dairy Sci 74:4119-4124.
Johnson, et al., "Mechanistic Basis for Therapeutic Targeting of the Mitochondrial FF-ATPase", downloaded from http://pubs.acs.org on Dec. 5, 2008, ASC Chem. Biol. 1 (5), 304-308, Publication Date (WEB): Jun. 9, 2006.
Thompson, C.B., "Apoptosis in the Pathogenesis and Treatment of Disease," Science 267:1456-1462 (1995).
Ursini et al., "Synthesis and SAR of New 5-Phenyl-3-ureido-1,5-benzodiazepines as cholecystokinin-B receptor antagonists", J. Med. Chem. 43 (2000) 3596-3613.
Walser, et al., "Quinazolines and 1,4-benzodiazepines. LILX. Preparation of Pyrrolo[2,1-c]-1,4-benzodiazepin-2- ones", J. Org. Chem. 38:3502-3507 (1973).
Watanabe-Fukunaga, R., et al., "Lymphoproliferation Disorder in Mice Explained by Defects in Fas Antigen that Mediates Apoptosia,"Nature 356:314-317 (1992).
White, E., "Life, Death, and the Pursuit of Apoptosis," Genes & Development 10:1-15 (1996).
Williams, D. et al, "Identification of compounds the bind mitochondrial F1F0 ATPase by screening a triazine library . . . " Chemistry & Biol. 11:1251-1259, 9(2004).
Wu, G.Y., et al., "Receptor-Mediated in Vitro Gene Transformation by a Soluble DNA Carrier System," The Journal of Biological Chemistry 262(10):4429-4432 (1987).
Wyllie, A.H., "The Genetic Regulation of Apoptosis," Current Opinion in Genetics & Development 5:97-104 (1995).
Zamzami, N., et al., "Mitochondrial Control of Nuclear Apoptosis," J. Exp. Med. 183:1533-1544 1996.
Zoratti, M., et al., "The Mitochondrial Permeability Transition," Biochimica et Biophysica Acta 1241:139-176 (1995).
International Search Report, International Patent Application No. PCT/US05/24060, dated Dec. 13, 2006.
International Search Report, International Patent Application No. PCT/US02/26171 dated Aug. 8, 2003.
International Search Report, International Patent Application No. PCT/US01/11599 dated Mar. 6, 2001.
International Search Report, International Patent Application No. PCT/US005/031942 dated Sep. 21, 2006.

EP Supplementary Search Report, EP Application No. 02794914.8 dated Nov. 6, 2008.
Lee, et al., J. Org. Chem. 1999, 64, 3060-3065.
Solomko, et al., Chemistry of Heterocyclic Compounds, vol. 11, No. 11, Nov. 1975, pp. 1231-1248.
EP Patent Application No. 05 80 4417 Supplementary European Search Report dated Mar. 26, 2009.
Algarra, et al., "Application of the Photo-Fries Rearrangement of Aryl N-Chloroacetylanthranylates as Key Step in the . . . ", Heterocycles, vol. 36 1993, pp. 2335-2344.
EP Patent Application No. 06 717616 Supplementary Search Report dated Mar. 26, 2009.
Levitzki, Alexander, "Protein Tyrosine Kinase Inhibitors as Novel Therapeutic Agents," Pharmacol. Ther. vol. 82, Nos. 2-3, pp. 231-239 (1999).
Sanchez, et al., "Tumorigenic activity of the BCR-ABL oncogenes is mediated by BCL2" Proc Natl Acad Sci U S A (Jun. 6, 1995) 92(12) 5287-5291.
Ji Yang, et al., "Prevention of Apoptosis by BCL-2; Release of Cytochrome c from Mitochondria Blocked" Science vol. 275, No. 5303, pp. 1129-113221 (1997).
Prindull, "Apoptosis in the embryo and tumorigenesis" European Journal of Cancer, vol. 31, Issue 1 (1995) pp. 116-123.
Kerver et al, "In situ detection of spontaneous superoxide anion and singlet oxygen production by mitochondria in . . . ", Histochem. J., 29:229-237 [1997] (Abstract only).
Kim et al., "Synthesis of 3-substituted 1,4-benzodiazepin-2-ones," J. Braz. Chem. Soc. 9:375-379 (1998).
Kohler and Milstein, "Continuous cultures of fused cells . . . ", Nature, 256:495-497 [1975].
Koopman, W.J., et al., "The MRL-Ipr/Ipr Mouse. A Model for the Study of Rheumatoid Arthritis," Scan& J. Rheumatolo Suppl 75:284-o289 (1988).
Korsmeyer, S.J., "Bcl-2 Initiates a New Category of Oncogenes: Regulators of Cell Death," Blood 80(4):879-886 1992.
Kozbor, et al.• "The production of monoclonal antibodies from human lymphocytes", Immunol. Today, 4:72 [1983].
Lee, Sunwoo, et al., "Improved Catalysts for the Palladium-Catalyzed Synthesis of Oxindoles by . . . ", J. Org. Chem. 2001, 66, pp. 3402-3415.
Lewis et al., "Editors' view: Cancer pharmacotherapy: 21st century 'magic bullets' and changing paradigms", British Journal of Clinical Pharmacology, 2006, 62:1,pp. 1-4.
Liu, J.R., et al., "Bclox•. is Expressed in Ovarian Carcinoma and Modulates Chemotherapy-induced Apoptosis," Gynecologic Oncology 70:398-403 (1998).
Los, M., et al., The Role of Caspases in Development, Immunity, and Apoptotic Signal Transduction: Immunity-10:629-639 (1999).
Lowman, et al., "Mutational analysis and protein engineering of receptor-binding determinants in human placental lactogen", J. Biol. Chem. 266:10982 [1991].
Luria,et al., "Tumor Viruses", General Viology 3rd edition,. 436-446 (1978)- Eds. John Wile & Sons, New York.
Malgrange, B., et al., "l•-Carbolines Induce Apoptotic Death of Cerebellar Granule Neurones in Cultures," NeuroReport 7(18):3041-3045 (1996).
Marino, M., et al., "Prevention of Systemic Lupus Erythematosus in MRL/Ipr Mice by Administration of an Immunoglobulin . . . ," Nature Biotechnology -18:735-739 (2000).
MCDonnell'—349:254-256T'J"et al.,"Progression from Lymphoid Hyperplasia to High-Grade . . . Nature-349:254-256 (1991).
Miccoli, et al., "Potentiation of Lonidamine and Diazepam . . . ", Journal of the National Cancer Institute, vol. 90, No. 18, pp. 1400-1406, Sep. 1998.
Miernik et al., "The antimitotic activities of some benzodiazepines", Experientia, 1986, 42, pp. 956-958.
Miller, K.A., et al., "Benzodiazepines Prevent Neuronal Death by Apoptosis & Necrosis . . . ," Society for Neuroscience Abstracts—24(1-2):979 (1998).
Monks, A., et., Feasibility of High-Flux Anticancer Drug Screen Using a Diverse Panel of Cultured Human Tumor Cell Lines, Journal of the National Cancer Institute, 83:757-766 (1991).

Nagata, S., "Human Autoimmune Lymphoproliferative Syndrome, a Defect in the Apoptosis-Inducing Fas Receptor: A 55 Lesson from the Mouse Model," J. Hum. Genet 43:2-8 (1998).

Okuyama, H., et al., "Analysis of Defective Delayed-Type Hypersensitivity in Autoimmune Mice Bearing Ipr Gene," Clln. Ex p. ImmunoL 63:87-94 1986.

Okuyama, H., et al., "Effect of Cyclophosphamide Pretreatment on Defective Delayed-Type Hypersensitivity . . . ," Int Arch. Allergy Appl. Immunol. 88:394-40 (1989).

Ozols, R.F., "Paclitaxel Plus Carboplatin in the Treatment of Ovarian Cancer," Seminars in Oncology 26(1) (Supp.2:84-89 (1999).

Paola Costantini et al., "Mitochondrion as Novel Target of Anticancer Chemotherapy", JNCI Journal of the National Cancer Institute 2000 92(13): 1042-1053; doi:10. 1093/jnci/92. 13. 1042. (2000).

Parks, Daniel J. "1,4-benzodiazepine-2,5-diones as small molecule antagonists of the HDM2-p53 interaction . . . " Bioorg Med Chem. Ltrs,. 15,(2005), 765-770.

Paull, K.D., et al., "Display and analysis of patterns of differential activity of drugs against human tumor . . . ", J. Natl. Cancer Inst., 81:1088-1092 [1989] (Abstract only).

Pestell, K.E., et al., "Charactehsation of the P53 Status, BCL-2 Expression and Radiation and Platinum Drug Sensitivity of . . . ," Int J. Cancer -77:913-918 (1998).

Raboisson, P. "Structure-based design, synthesis and biological evaluative of novel 1,4-diazepines as HDM2 antagonists," Bioorg Med Chem. Ltrs., 15,(2005), 1857-1861.

Ramdas et al., "Benzodiazepine compounds as inhibitors of the Src protein tyrosine kinase . . . " Archives of Biochemistry and Biophysics 368 (1999) 394-400.

Raynaud, F.I., et al., "Intracellular Metabolism of the Orally Active Platinum Drug JM216: Influence of Glutathione Levels," Br. J. Cancer 74(3) :380-?386 (1996).

Russell, J.H., et al., "Mature T Cells of Autoimmune lpr/lpr Mice have a Defect in Antigen-Stimulated Suicide,"Proc. Nat. Acad. Sci. USA 90:4409-4413 (1993).

Sakata, K., et al., "Role of Fas/FasL Interaction in Physiology and Pathology: The Good and the Bad," Clinical Immunology and Immunopathology 87(1):1-7 (1998).

Sandstrom, P.A., et al., Autocrine Production of Extracellular Catalase Prevents Apoptosis.. Proc. Natl. Acad. Sci. USA-90:4708-4712 (1993).

Schlumpf, M., et al., "Delayed Developmental Immunotoxicity of Prenatal Benzodiazepines,"Toxic. In Vitro—8 (5):1061-1065(1994).

Schoemaker, H., et al., "Specific High-Affinity Binding Sites for [3H]Ro5—4864 in Rat Brain and Kidney," The J. of Pharm and Experimental Therapeutics -225(1)61-69 (1983).

Schwab, M., et al., "Amplified DNA with Limited Homology to myc Cellular Oncogene is Shared by Human Neuroblastoma Cell Lines and . . . ," Nature -305:245-248 (1983).

Scott, C.F., et al., "Comparison of Antigen-Specific T Cell Responses in Autoimmune MRL/mp-Ipr/Ipr and MRUMp-++ Mice," The Journal of Immunology- 1322:633-639 (1994.

Sentman, C.L., et al., "bcl-2 Inhibits Multiple Forms of Apoptosis but not Negative Selection in Thymocytes," Cell 67:879-886 (1991).

Shaughnessy, Kevin, H., et al., "Palladium-Catalyzed Inter- and Intramolecular . . . " J. Org. Chem. 1998, 63, pp. 6546-6553.

Sheppard, R.C., et al., "Acid-Labile Resin Linkage Agents for Use in Solid Phase Peptide Synthesis;" Int J. Peptide Protein Res. 20:451-454 (1982).

Snyder, Jane R., et al, "Dissection of melanogenesis with small molecules identifies prohibition as a regulator", Chemistry & Biol. 12:477-484, 4(2005).

Stevens, S.Y., et al., "Non Nucleic Acid Inhibitors of Protein-DNA Interactions Identified Through Combinatorial Chemistry," J. Am. Chem.Soc. -118:10650-10651 (1996).

Sugimoto, T., et al., Determination of Cell Surface Membrane Antigens . . . JNCI-73: (1):51-57 (1984).

Swanson et al, "Ligand recognition by anti-DNA Autoantibodies," Biochemistry, 35:1624-1633 [1996] (Abstract only).

Swanson, P.C., et al., "Ligand Recognition by Murine Anti-DNA Autoantibodies," J. Clin. Invest 97(7):1748-1760 (1996).

Swanson, P.C.,et al., "High Resolution Ephope Mapping of an Anti-DNA Autoantibody Using Model DNA Ligands," J. Immunology 71 152(5):2601-2612 (1994).

Takahashi, T., et al., "Generalized Lymphoproliferative Disease in Mice, Caused by a Point Mutation in the Fas Ligand;" Cell 76:969-976 (1994).

Tanimoto, Y., et al., Benzodiazepine Receptor Agonists Modulate Thymocyte Apoptosis Through Reduction of the Mitochondrial . . . Jpn. J. Pharmacol. 79:177-183 (1999).

Taupin, V., et al., Endogenous Anxiogenic peptide, ODN-Diazepam-Binding Inhibitor, and Benzodiazepines.. Lymphokine and Cytoklne Research 10(1):7-13 (1991).

Theoffopoulous, AN, et al., "Murine Models of Systemic Lupus Erythematosus," Advances in Immunology 37:269-390 (1985).

Adachi, M., et al., "Aberrant Transcription Caused by the Insertion an Early Transposable Element . . . ," PNAS. USA-90:1756-1760 (1993).

Adelman, N.E., et al., Treatment of (NZB X NZW)F1 Disease with Anti-I-A Monoclonal Antibodies; J. Exp. Med.-158:1350.1355 (1983).

Atwal, K.S., et al., "N-(1-Aryl-2-(1-imidazolo)ethyl)-guanidine derivates as potent inhibitors of the bovine mitochondrial F140 ATP hydrolase" Bioorganic & Medicinal Chem. Ltr., vol. 14, pp. 1021-1030 (2004).

Atwal, K.S., et al., "Small Molecule Mitochondrial F1F0 ATPase Huydrolase Inhibitors as Cardioprotective Agents" J. Med. Chem. 47, pp. 1081-1084 (2004).

Baader, S.L., et al., Uptake and Cytotoxicity of Ascorbic Acid and Dehydroascorbic Acid . . . Anticancer Research-14:221-228 (1994).

Beale, P.J., et al., "BCL-2 Family Protein Expression and Platinum Drug Resistance in Ovarian Carcinoma," British Journal of Cancer-82 (2) :436-440 (2000).

Beurdeley-Thomas, et al., "The peripheral benzodiazepine receptors: a review," Journal of Neuro-Oncology 46 (2000) 45-56.

Blatt, Neal B., "Benzodiazepine-induced superoxide signals B cell apoptosis: mechanistic insight and potential therapeutic utility", The Journal of Clinical Investigation, Oct. 2002, vol. 110, No. 8., pp. 1123-1132.

Blum, P., et al., "Stiff-Person Syndrome: An Autoimmune Disease," Movement Disorders 6(1):12-20 (1991).

Boitano, Anthony, et al., "Structure activity studies of a novel cytotoxic benzodiazepine", Bioorganic & Medicinal Chemistry Letters, Oxford, GB, vol. 13, No. 19, 2003, pp. 3327-3330.

Bono et al., "Peripheral benzodiazepine receptor agonists exhibit potent antiapoptotic activities," Biochemical and Biophysical Research Communications, 1999, 265, pp. 457-461.

Boojamra, C.G., et al., "Solid-Phase Synthesis of 1,4. Benzodiazepine-2,5-Diones. Library Prep. and Demonstration of Synthesis Generality," J. Org. Chem.-62:1240-1256 (1997).

Bunin et al., "Synthesis and evaluation of 1,4-benzodiazepine libraries", Methods in Enzymology, 1996, 267, pp. 448-465.

Bunin, B.A., et al., "The Combinatorial Synthesis and Chemical and Biological Evaluation of a 1,4-Benzodiazepine Libra ," PNAS USA-91:4708-4712 (1994).

Bunin, BA., et al., "A General and Expedient Method for the Solid-Phase Synthesis of 1,4-Benzodlazepine Derivatives," J. Am. Chem. Soc. -114:10997-10998 (1992).

Chumakov,A.M., et al., "Analysis of p53 Transactivation Through High-Affinity Bindir•g Sites," Oncogene-8:3005o3011 (1993).

Churcher et al., "A new series of potent benzodiazepine y-Secretase inhibitors," Bioorganic & Medicinal Chemistry Letters 13 (2003) 179-.

Cohen, P.L., et al., "Lpr and gld: Single Gen• Models of Systemic Autoimmunity and Lymphoproliferative Disease," Annu. Rev. Immunol. 9:243-269 (1991).

Cole et al., "The EBV-Hybridoma Technique and its Application to Human Lung Cancer", Monoclonal Antibodies and Cancer Therapy, Alan R. Liss, Inc., pp. 77-96 [1985].

Colosi, et al,"Mutational analysis of the intracellular domain of the human growth hormone recetor", J. Biol. Chem., 268:12617 [1993].

Crabtree, R.H., "A New Type of Hydrogen Bond," Science 282:2000-2001 1998.

Darrow et al., "Structurally similar small molecule photoaffinity CCK-A Agonists and Antagonists as Novel Tools . . . ", Bioorganic & Medicinal Chemistry Letters 8 (1998) 3127-3132.

Desoize, B., "Anticancer Drug Resistance and Inhibition of Apoptosis," Anicancer Research -14:2291-2294 1994.

Dichek, David A., et al., "Seeding of intravascular stents with genetically engineered endothelial cells," Laboratory Investigation, 80:5 pp. 1347-1353 (1989).

Doble, A., et al., "Labelling of Peripheral-Type Benzodiazepine B Human Brain with [aH]l 1195: Anatomical and Subcellular Distribution," Brain Research Bulletin,18:49-61 1987.

Don, A. et al., Cancer Cell, vol. 3, May 2003 497-509.

Donadio, J.V., et al., Immunosuppressive Drug Therapy in Lupus Nephritis, American Journal of Kidney Diseases 21 (3):239-250 1993.

Ermak, T.H., et al., "Treatment of Murine Lupus with Monoclonal Antibody to L3T4," Laboratory Investigation 61(4):447-456 1989.

Fuh et al, "Rational design of potent antagonists to the human growth hormone receptor", Science, 256:1677 [1992].

Gallant, J.E., et al.,"Incidence and Natural History of Cytomegalovirus Disease in Patients with Advanced Human . . . " The Journal of Infect. Disease, 166: 1223-122 (1992).

Garcia-Calvo, M., et al. "Inhibition of Human Caspases by Peptide-Based and Macromolecular Inhibitors," The Journal of Biological Chemistry 273(49):32608-32613 1998.

Gorczyca, W., et al., "Induction of DNA Slrand Breaks Associated with Apoptosis During Treatment of Leukemias," Leukemia 7(5):659-670 1993.

Gordon, C., et al.. "Chronic Therapy with Recombinant Tumor Necrosis Factor-or in Autoimmune NZB/NZW Fi Mice," Clinical Immunology and Immunopatholoy- 52:421-434 (1989).

Gordon, E.M., et al., Applications of Combinatorial Technologies to Drug Discovery. 2. Combinatorial Organic 52 Synthesis, Library Screening . . . Journal of Med. Chem. 37(10): (1994).

Grasberger, Bruce L., "Discovery and cocrystal structure of benzodiazepinedione HDM2 antagonists that activate p53 in cells", J. Med. Chem., 48, (2005), 909-912.

Karle Jesper et al., "Diazepam protects against rat hippocampal neuronal cell death induced by antisense oligodeoxynucleotide to GABA-A receptor gamma-2 subunit" Brain Research, vol. 765, No. 1, 1997, pp. 21-29.

Hahn, B.H., et al.; "Influence of Cyclophosphamide and Other Immunosuppressive Drugs on Immune Disorders . . . ," Arthritis and Rheumatism -18(2):145-152 (1975).

Hamann, L.G., et al., "Benzodiazepine-based selective inhibitors of mitochondrial F1F0 ATP hydrolase" Bioorganic & Medicinal Chemistry Ltrs. 14 pp. 1031-1034 (2004).

Hang, L., et al., "A Spontaneous Rheumatoid Arthritis-Like Disease in MR/1 Mice," J. Exp. Mod. -155:1690-1701 1982.

Herranz, R., "Cholesystokinin Antagonists: Pharmacological and Therapeutic Potential", Medicinal Research Reviews 23 (2003) 559-603.

Hirsch, et al., "PK11195, a Ligand of the Mitochondrial Benzodiazepine Receptor, Facilitates the Induction of Apoptosis and Reverses Bcl-2-Mediated Cytoprotection," Experimental Cell Research 241, 426-434 (1998).

Horowitz, R.E., et al., "Cyclophosphamide Treatment of Mouse Systemic Lupus Erythematosus," Laboratory Investigation 21 (3): 199-206 1969.

Hulme, C. J. "Improved procedure for the solution phase preparation of 1,4-benzodiazepine-2,5-dione libraries . . . ", Org. Chem., 63,(1998), 8021-8023.

Huse et al., "Generation of a Large Combinatorial Library of the Immunoglobulin Repertoire in Phage Lambda", Science, 246:1275-1281 [1989].

International Search Report and Written Opinion of PCT/US2008/057827 dated Oct. 6, 2008.

IPER and ISR for PCT/us02/31942 mailed Feb. 2, 2007.

Itoh, N., et al., "The Polypeptide Encoded by the cDNA for Human Cell Surface Antigen Fas Can Mediate Apoptosis," Cell 66:233-243 (1991).

Jones, The non-conalent interaction of pyrrolo[2, 1-c][benzodiazepines-5, 11-diones with DNA, Anti-Cancer Drug Design, 5:249-264 (1990).

Kamal, A., "Synthesis of DNA-interactive Pyrrolo[2,1-c][1,4] benzodiazepines by employing polymer-supported reagents . . . ," Synlett, 14,(2004), 2533-35.

Bhagavathula, Narasimharao, et al., "7-Chloro-t-(4-hydroxyphenyl__-1-methyl-3-(naphthalen-2-ylmethyl) . . . ", J. Pharmacol & Exp Ther 324: 938-947 (2008).

Borea, "Stereochemical Features Controlling Binding and Intrinsic Activity Properties of Benzodiazepine Receptor Ligands", Molecular Pharmacology, Apr. 1987, 31 (4), pp. 334-344, p. 344, Abstract.

Mahrle, et al., Br. J. Bermatol. 1974, 91, 529-540.

Mui et al. Br. J. Dermatol. 1975, 92, 255-262.

EP Search Report dated Nov. 26, 2009, EP Patent Application No. 09003224.4.

Nadin, Alan, et al., "New Synthesis of 1,3-Dihydro-1,4-benzodiazepin-2(2H)-ones and 3-Amino-1,3-dihydro-1,4-benzodiazepin-2(2H)-ones: Pd-Catalyzed Cross-Coupling of Imidoyl Chlorides with Organoboronic Acids," J. Org. Chem., 2003, 68, pp. 2844-2852.

Reddy, Pavan, et al., "Interleukin-18 Regulates Acute Graft-Versus-Host Disease by Enhancing Fas-mediated Donor T Cell Apoptosis," J. Exp. Med., 2001, 194: 1433-1440.

Bossu, et al., "IL-18 cDNA vaccination protects mice from spontaneous lupus-like automimmune disease," PNAS 2003, 100: 14181-14186.

De Bandt, et al., "Systemic lupus erythematosus induced by antitumour necrosis factor alpha therapy: a French national survey," Arthritis Res. & Ther., 2005, 7: R545-R551.

Abunasser, et al., "Etanercept-Induced Lupus Erythematosus Presenting as a Unilateral Pleural Effusion," Chest 2008, 134: 850-853.

Busca, et al., "Recombinant human soluble tumor necrosis factor receptor fusion protein as treatment for steroid refractory graft-versus-host disease following allogeneic hematopoietic stem cell transplatation," Am. J. Hematol., 2007, 82: 45-52.

Kyungjin, Kim, Steven K. Volkkan, and Jonathan A. Ellman, Synthesis of 3-Substituted 1,4-Benzodiazepin-2-ones, J. Braz. Chem. Soc. vol. 9(4), 375-379 (1998).

Kluge, et al., "Kinetics of Inactivation of the F1F0 ATPase of Propionigenium modestum by Dicyclohexylcarbodiimide in Relationship to H+ and Na+ Concentration: Probing the Binding Site for the Coupling Ions," Biochemistry 1993, 32, 10378-10386.

Covelli, Vito, "Stress, Neuropsychiatric Disorders and Immunological Effects Exerted by Benzodiazepines," Immunopharmacology and Immunotoxicology, 20(2), 199-209 (1998).

EP Search Report dated Jun. 23, 2010, EP Patent Application No. 10 003 823.1.

EP Search Report dated Aug. 10, 2010, EP Patent Application No. 08731682.4.

Office Action Mailed Apr. 3, 2009, U.S. Appl. No. 11/176,719, filed Jul. 6, 2005.

Office Action Mailed Aug. 19, 2009, U.S. Appl. No. 11/176,719, filed Jul. 6, 2005.

Office Action Mailed May 24, 2010, U.S. Appl. No. 11/176,719, filed Jul. 6, 2005.

Tarpley, et al., J. Chroni Diseases (1965), 18 (abstract only).

Dourlat, et al., "Novel 1,4-benzodiazepine derivaties with antiproliferative properties on tumor cell lines," Bioorganic & Medicinal Chemistry Letters, 2007, vol. 17, Issue 9, pp. 2527-2530.

Elz et al., 1989 Eur. J. Med Chem. 259-262.

Atwal et al., Tet Lett. 30, 1989, 7313.

Johnson, K.M., et al., Chemistry & Biology, 2005, 12:486-496.

Francis, T.M., et al., "Identification of cytotoxic, T-cell-selective 1,4-benzodiazepine-2,5-diones," Bioorganic & Medicinal Chemistry Letters, Pergamon, Elsevier Science, GB, vol. 16, No. 9, May 1, 2006, pp. 2423-2427.

Akssira, M., et al., "New Routes to 1,4-benzodiazepin-2,5-diones," Tetrahedron (1994), vol. 50, No. 30, pp. 9051-9060.

Mohiuddin, G., et al., "A Versatile Synthesis of 3H-1(H), 4(H)-Benzodiazepin-2,5-diones," Indian Journal of Chenmistry, 1985, vol. 24B, pp. 905-907.

Boojamra, Constantine G., et al., "An Expedient and High-Yielding Method for the Solid-Phase Synthesis of Diverse 1,4-Benzodiazepine-2, 5-diones," Journal of Organic Chemistry, 1995, vol. 60, No. 18, pp. 5742-5743.

Keating, Thomas A., et al., "A Remarkable Two-Step Synthesis of Diverse 1, 4-Benzodiazepine-2, 5-diones Using the Ugi Four-Component Condensation," Journal of Organic Chemistry, 1996, vol. 61, No. 25, pp. 8935-8939.

Juaristi, Eusebio, et al., "Enantioselective Synthesis of α-Amino Acides from Chiral 1, 4-enzodiazepine-2, 5-diones Contianing the α-Phenethyl Group," Journal of Organic Chemistry, Mar. 26, 1999, vol. 64, No. 8, pp. 2914-2918.

Marc, Gasper, et al., "High Yield Phase Transfer N-Alkylation of Some Benzodiazepinese by Esters of ω-Halo Acids," Synthetic Communications, 1998, vol. 28, No. 7, pp. 1143-1157.

Bolli, M.H., et al., "Novel Benzo[1,4]diazepin-2-one-Derivatives as Endothelin Receptor Antagonists", Journal of Medicinal Chemistry, vol. 47, No. 11, Apr. 23, 2004, pp. 2776-2795.

Cunha, 2006, "The first bismuth(III)-catalyzed guanylation of thioureas", Tetrahedron Letters 47:6955-56.

Cunha, 2002, "Bismuth nitrate pentahydrate: a new and environmentally benign reagent for guanidylation of N-benzoylthioureas", Tetrahedron Letters 43: 49-52.

COMPOSITIONS AND METHODS RELATING TO NOVEL COMPOUNDS AND TARGETS THEREOF

RELATED APPLICATIONS CROSS REFERENCE TO RELATED APPLICATIONS

This application is a 371 United States national stage application of pending International Patent Application No. PCT/US2007/013576, International Filing Date Jun. 8, 2007, which claims the benefit of priority to U.S. Provisional Patent Application Ser. No. 60/812,270, filed Jun. 9, 2006, the contents of which are hereby incorporated by reference.

STATEMENT REGARDING FEDERALLY SPONSORED RESEARCH OR DEVELOPMENT

This invention was made with government support under Grant No. GM046831 awarded by the National Institutes of Health. The government has certain rights in the invention.

FIELD OF THE INVENTION

The present invention relates to novel chemical compounds, methods for their discovery, and their therapeutic use. In particular, the present invention provides benzodiazepine derivatives and related compounds and methods of using benzodiazepine derivatives and related compounds as therapeutic agents to treat a number of conditions associated with the faulty regulation of the processes of programmed cell death, autoimmunity, inflammation, hyperproliferation, and the like.

BACKGROUND OF THE INVENTION

Multicellular organisms exert precise control over cell number. A balance between cell proliferation and cell death achieves this homeostasis. Cell death occurs in nearly every type of vertebrate cell via necrosis or through a suicidal form of cell death, known as apoptosis. Apoptosis is triggered by a variety of extracellular and intracellular signals that engage a common, genetically programmed death mechanism.

Multicellular organisms use apoptosis to instruct damaged or unnecessary cells to destroy themselves for the good of the organism. Control of the apoptotic process therefore is very important to normal development, for example, fetal development of fingers and toes requires the controlled removal, by apoptosis, of excess interconnecting tissues, as does the formation of neural synapses within the brain. Similarly, controlled apoptosis is responsible for the sloughing off of the inner lining of the uterus (the endometrium) at the start of menstruation. While apoptosis plays an important role in tissue sculpting and normal cellular maintenance, it is also the primary defense against cells and invaders (e.g., viruses) which threaten the well being of the organism.

Not surprisingly many diseases are associated with dysregulation of the process of cell death. Experimental models have established a cause-effect relationship between aberrant apoptotic regulation and the pathenogenicity of various neoplastic, autoimmune and viral diseases. For instance, in the cell mediated immune response, effector cells (e.g., cytotoxic T lymphocytes "CTLs") destroy virus-infected cells by inducing the infected cells to undergo apoptosis. The organism subsequently relies on the apoptotic process to destroy the effector cells when they are no longer needed. Autoimmunity is normally prevented by the CTLs inducing apoptosis in each other and even in themselves. Defects in this process are associated with a variety of autoimmune diseases such as lupus erythematosus and rheumatoid arthritis.

Multicellular organisms also use apoptosis to instruct cells with damaged nucleic acids (e.g., DNA) to destroy themselves prior to becoming cancerous. Some cancer-causing viruses overcome this safeguard by reprogramming infected (transformed) cells to abort the normal apoptotic process. For example, several human papilloma viruses (HPVs) have been implicated in causing cervical cancer by suppressing the apoptotic removal of transformed cells by producing a protein (E6) which inactivates the p53 apoptosis promoter. Similarly, the Epstein-Barr virus (EBV), the causative agent of mononucleosis and Burkitt's lymphoma, reprograms infected cells to produce proteins that prevent normal apoptotic removal of the aberrant cells thus allowing the cancerous cells to proliferate and to spread throughout the organism.

Still other viruses destructively manipulate a cell's apoptotic machinery without directly resulting in the development of a cancer. For example, the destruction of the immune system in individuals infected with the human immunodeficiency virus (HIV) is thought to progress through infected $CD4^+$ T cells (about 1 in 100,000) instructing uninfected sister cells to undergo apoptosis.

Some cancers that arise by non-viral means have also developed mechanisms to escape destruction by apoptosis. Melanoma cells, for instance, avoid apoptosis by inhibiting the expression of the gene encoding Apaf-1. Other cancer cells, especially lung and colon cancer cells, secrete high levels of soluble decoy molecules that inhibit the initiation of CTL mediated clearance of aberrant cells. Faulty regulation of the apoptotic machinery has also been implicated in various degenerative conditions and vascular diseases.

It is apparent that the controlled regulation of the apoptotic process and its cellular machinery is vital to the survival of multicellular organisms. Typically, the biochemical changes that occur in a cell instructed to undergo apoptosis occur in an orderly procession. However, as shown above, flawed regulation of apoptosis can cause serious deleterious effects in the organism.

There have been various attempts to control and restore regulation of the apoptotic machinery in aberrant cells (e.g., cancer cells). For example, much work has been done to develop cytotoxic agents to destroy aberrant cells before they proliferate. As such, cytotoxic agents have widespread utility in both human and animal health and represent the first line of treatment for nearly all forms of cancer and hyperproliferative autoimmune disorders like lupus erythematosus and rheumatoid arthritis.

Many cytotoxic agents in clinical use exert their effect by damaging DNA (e.g., cis-diaminodichroplatanim(II) crosslinks DNA, whereas bleomycin induces strand cleavage). The result of this nuclear damage, if recognized by cellular factors like the p53 system, is to initiate an apoptotic cascade leading to the death of the damaged cell.

However, existing cytotoxic chemotherapeutic agents have serious drawbacks. For example, many known cytotoxic agents show little discrimination between healthy and diseased cells. This lack of specificity often results in severe side effects that can limit efficacy and/or result in early mortality. Moreover, prolonged administration of many existing cytotoxic agents results in the expression of resistance genes (e.g., bcl-2 family or multi-drug resistance (MDR) proteins) that render further dosing either less effective or useless. Some cytotoxic agents induce mutations into p53 and related proteins. Based on these considerations, ideal cytotoxic drugs should only kill diseased cells and not be susceptible to chemo-resistance.

Many autoimmune diseases and haematologic malignancies result from the aberrant survival and expansion of B and T cells in central and peripheral lymphoid organs. Current therapies for these for these disorders generally employ cytotoxic drugs whose mechanisms of action frequently involves DNA damage. Hence, the selectivity of these drugs is limited and often relies on the differential ability of diseased and healthy cells to tolerate and repair drug-induced cellular damage.

What are needed are improved compositions and methods for regulating the apoptotic processes in subjects afflicted with diseases and conditions characterized by faulty regulation of these processes (e.g., viral infections, hyperproliferative autoimmune disorders, chronic inflammatory conditions, and cancers).

SUMMARY

The present invention relates to novel chemical compounds, methods for their discovery, and their therapeutic use. In particular, the present invention provides benzodiazepine derivatives and related compounds and methods of using benzodiazepine derivatives and related compounds as therapeutic agents to treat a number of conditions associated with the faulty regulation of the processes of programmed cell death, autoimmunity, inflammation, hyperproliferation, and the like. Such compounds and uses are described throughout the present application and represent a diverse collection of compositions and applications.

In one aspect, the invention provides a compound represented by the following formula:

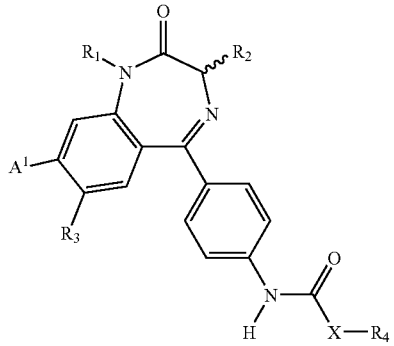

including salts and both R and S enantiomeric forms and racemic mixtures thereof;
wherein
A$^1$ is H, Br, Cl, NO$_2$, or CF$_3$;
R$_1$ is CH$_3$ or H;
R$_2$ is

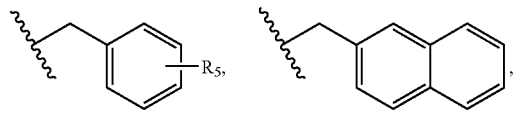

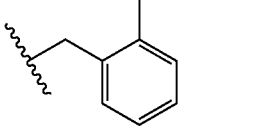, or 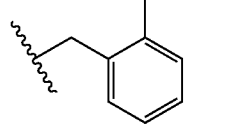

R$_3$ is H, Br, Cl, NO$_2$, or CF$_3$;
R$_4$ is phenyl,

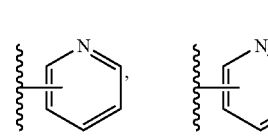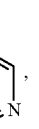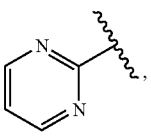

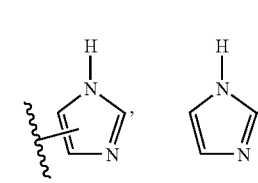, or 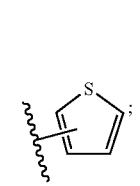

R$_5$ is CH$_3$, —CH$_2$CH$_3$, —(CH$_2$)$_2$CH$_3$, —CH(CH$_3$)$_2$, —(CH$_2$)$_3$CH$_3$, —C(CH$_3$)$_3$, phenyl, phenoxy, hydroxyphenyl, Br, F or Cl;
R$_6$ is H, Br, Cl, F, —OCH$_3$, or —OCH(CH$_3$)$_2$;
X is CH$_2$, or NH; and
provided that at least one of A$^1$ and R$_3$ is not H.

In certain embodiments, A$^1$ is Cl or NO$_2$; and R$_3$ is H. In other embodiments, A$^1$ is H; and R$_3$ is Cl or NO$_2$.

In certain embodiments, R$_2$ is

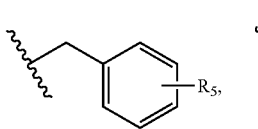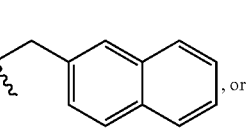,

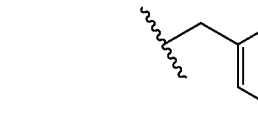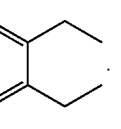.

In certain embodiments, X is CH$_2$. In other embodiments, X is NH.

In certain embodiments, R$_4$ is phenyl,

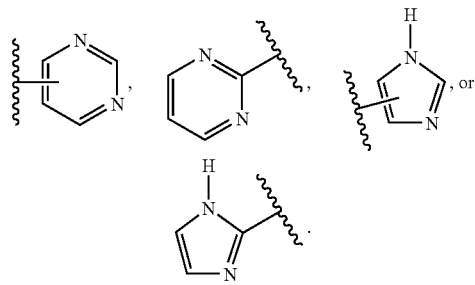

In another aspect, the invention provides a compound represented by the following formula:

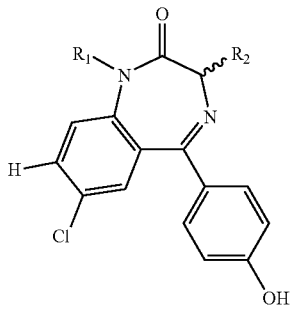

including salts and both R and S enantiomeric forms and racemic mixtures thereof;
wherein
R$_1$ is CH$_3$ or H;
R$_2$ is

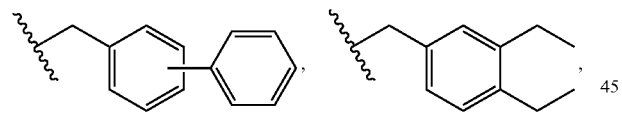

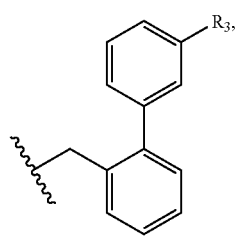

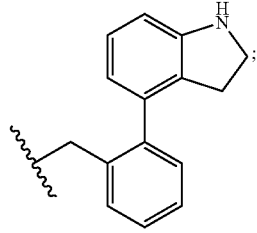

R$_3$ is Br, Cl, F, —OCH$_3$, or —OCH(CH$_3$)$_2$.
In certain embodiments, R$_2$ is

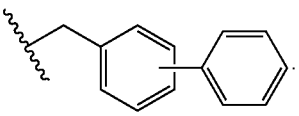

In another aspect, the invention provides a compound represented by the following formula:

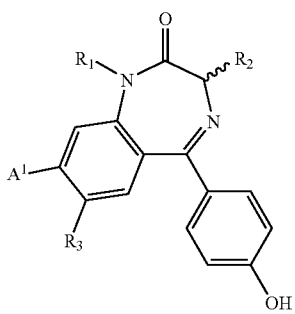

including salts and both R and S enantiomeric forms and racemic mixtures thereof;
wherein
A$^1$ is H or Cl;
R$_1$ is H or CH$_3$;
R$_2$ is

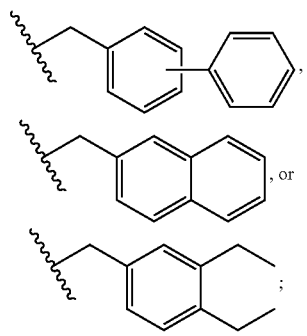

R$_3$ is H or Br; and
provided that at least one of A$^1$ and R$_3$ is not H.
In certain embodiments, A$^1$ is H, and R$_3$ is Br.
In another aspect, the invention provides a compound represented by the following formula:

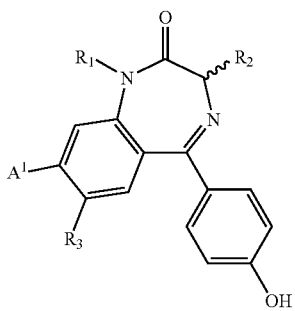

including salts and both R and S enantiomeric forms and racemic mixtures thereof;
wherein
A$^1$ is H or —NO$_2$;
R$_1$ is H or CH$_3$;
R$_2$ is

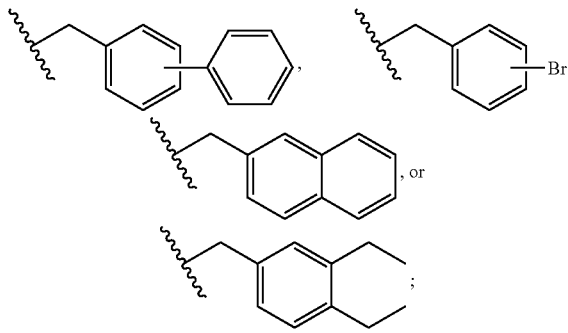

R$_3$ is H, —NO$_2$, or CF$_3$; and
provided that at least one of A$^1$ and R$_3$ is not H.

In certain embodiments, A$^1$ is H; and R$_3$ is —NO$_2$, or CF$_3$.

In addition, the invention provides a pharmaceutical composition comprising at least one of the foregoing compounds together with a pharmaceutically acceptable carrier.

In addition, the invention provides a method of treating a disorder selected from the group consisting of an immune disorder, a hyperproliferative disorder, and a chronic inflammatory condition. The method comprises administering an effective amount of at least one of the foregoing compounds to a subject in need thereof suffering from such a disorder.

The compounds of the invention may be used to treat immune disorders that include, for example, autoimmune hemolytic anemia, autoimmune hepatitis, Berger's disease or IgA nephropathy, Celiac Sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjorgren syndrome, systemic lupus erythematosus, type 1 diabetes, ulcerative colitis, and vitiligo. In addition, the compounds can be used to reduce or eliminate tissue or organ rejection following a transplant procedure.

The compounds of the invention may be used to treat a hyperproliferative disorder, for example, cancer, which can be malignant or benign. Exemplary cancers that may be treated include, for example, adenomas, adenocarcinomas, carcinomas, leukemias, lymphomas, melanomas, myelomas, sarcomas, and teratomas. In addition, it is contemplated that the compounds of the invention may be used to treat cancers of the bladder and the renal system, brain, breast, cervix, colon, lung, ovaries, prostate, rectum.

In addition, the compounds of the invention may be used to treat a chronic inflammatory condition, for example, asthma or psoriasis.

It is understood that in the method of treating of an immune disorder, the method optionally includes administering (separately or in combination) an additional agent for treating the immune disorder. Similarly, it is understood that in the method of treating a cancer, the method optionally includes administering (separately or in combination) an additional agent for treating the cancer. In addition, it us understood that in the method of treating the chronic inflammatory condition, the method optionally includes administering (separately or in combination) an additional agent for treating the chronic inflammatory condition.

DEFINITIONS

To facilitate an understanding of the present invention, a number of terms and phrases are defined below.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., C$_1$-C$_{30}$ for straight chain, C$_3$-C$_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the term "substituted aryl" refers to an aromatic ring or fused aromatic ring system consisting of no more than three fused rings at least one of which is aromatic, and where at least one of the hydrogen atoms on a ring carbon has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

The term "derivative" of a compound, as used herein, refers to a chemically modified compound wherein the chemical modification takes place either at a functional group of the compound or on the aromatic ring.

The term "epidermal hyperplasia," as used herein, refers to an abnormal multiplication or increase in the number of normal cells in normal arrangement in epidermal tissue. Epidermal hyperplasia is a characteristic of numerous disorders, including but not limited to, psoriasis.

The term "keratinocyte" as used herein, refers to a skin cell of the keratinized layer of the epidermis.

The term "fibroblast" as used herein, refers to mesodermally derived resident cells of connective tissue that secrete fibrillar procollagen, fibronectin and collegenase.

The term "pigment disorder" as used herein, refers to disorders involving skin pigment (e.g., melanin). Examples of pigment disorders include, but are not limited to, all forms of albinism, melasma, pigment loss after skin damage, and vitiligo.

The term "stent" or "drug-eluting stent," as used herein, refers to any device which when placed into contact with a site in the wall of a lumen to be treated, will also place fibrin at the lumen wall and retain it at the lumen wall. This can include especially devices delivered percutaneously to treat coronary artery occlusions and to seal dissections or aneurysms of splenic, carotid, iliac and popliteal vessels. The stent can also have underlying polymeric or metallic structural elements onto which the fibrin is applied or the stent can be a composite of fibrin intermixed with a polymer. For example, a deformable metal wire stent such as that disclosed in U.S. Pat. No. 4,886,062, herein incorporated by reference, could be coated with fibrin as set forth above in one or more coats (i.e., polymerization of fibrin on the metal framework by application of a fibrinogen solution and a solution of a fibrinogen-coagulating protein) or provided with an attached fibrin preform such as an encircling film of fibrin. The stent and fibrin could then be placed onto the balloon at a distal end of a balloon catheter and delivered by conventional percutaneous means (e.g. as in an angioplasty procedure) to the site of the restriction or closure to be treated where it would then be expanded into contact with the body lumen by inflating the balloon. The catheter can then be withdrawn, leaving the fibrin stent of the present invention in place at the treatment site. The stent may therefore provide both a supporting structure for the lumen at the site of treatment and also a structure supporting the secure placement of fibrin at the lumen wall. Generally, a drug-eluting stent allows for an active release of a particular drug at the stent implementation site.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by the dysregulation of apoptotic processes.

In some embodiments, the "target cells" of the compositions and methods of the present invention include, refer to, but are not limited to, lymphoid cells or cancer cells. Lymphoid cells include B cells, T cells, and granulocytes. Granulocycles include eosinophils and macrophages. In some embodiments, target cells are continuously cultured cells or uncultered cells obtained from patient biopsies.

Cancer cells include tumor cells, neoplastic cells, malignant cells, metastatic cells, and hyperplastic cells. Neoplastic cells can be benign or malignant. Neoplastic cells are benign if they do not invade or metastasize. A malignant cell is one that is able to invade and/or metastasize. Hyperplasia is a pathologic accumulation of cells in a tissue or organ, without significant alteration in structure or function.

As used herein, the term "effective amount" refers to the amount of a compound (e.g., a compound of the present invention) sufficient to effect beneficial or desired results. An effective amount can be administered in one or more administrations, applications or dosages and is not limited intended to be limited to a particular formulation or administration route.

As used herein, the term "dysregulation of the process of cell death" refers to any aberration in the ability of (e.g., predisposition) a cell to undergo cell death via either necrosis or apoptosis. Dysregulation of cell death is associated with or induced by a variety of conditions, including for example, autoimmune disorders (e.g., systemic lupus erythematosus, rheumatoid arthritis, myasthenia gravis, Sjögren's syndrome, etc.), chronic inflammatory conditions (e.g., graft-versus-host disease, psoriasis, respiratory diseases, granulomatus diseases, scarcoid diseases, copd, Wegener granulomatosis, TB, asthma and Crohn's disease), hyperproliferative disorders (e.g., tumors, B cell lymphomas, T cell lymphomas, etc.), viral infections (e.g., herpes, papilloma, HIV), and other conditions such as osteoarthritis and atherosclerosis.

It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

A "hyperproliferative disorder," as used herein refers to any condition in which a localized population of proliferating cells in an animal is not governed by the usual limitations of normal growth. Examples of hyperproliferative disorders include cancers, for example, tumors, neoplasms, lymphomas, myelomas, and the like. It is understood that cancers include pre-cancerous lesions. A neoplasm is said to be benign if it does not undergo, invasion or metastasis and malignant if it does either of these. A metastatic cell or tissue means that the cell can invade and destroy neighboring body structures. Hyperplasia is a form of cell proliferation involving an increase in cell number in a tissue or organ, without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium. Hyperproliferative disorder includes cancers, such as myeloma, bladder cancer, and renal cancer.

As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, Celiac Sprue, chronic fatigue syndrome, Crohn's disease, dermatomyositis, fibromyalgia, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjorgren syndrome, systemic lupus erythematosus, type 1 diabetes, ulcerative colitis, vitiligo, tuberculosis, and the like. Graft versus host disease can result from an immune response to transplanted tissues, organs and the like (e.g., bone marrow, solid organ, skin, etc.).

As used herein, the term "chronic inflammatory condition" refers to a condition wherein the organism's immune cells are activated. Such a condition is characterized by a persistent inflammatory response with pathologic sequalae. This state is characterized by infiltration of mononuclear cells, proliferation of fibroblasts and small blood vessels, increased connective tissue, and tissue destruction. Examples of chronic inflammatory diseases include, but are not limited to, Crohn's disease, psoriasis, chronic obstructive pulmonary disease, inflammatory bowel disease, multiple sclerosis, and asthma. Immune diseases such as rheumatoid arthritis and systemic lupus erythematosus can also result in a chronic inflammatory state.

As used herein, the term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy.

Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfinuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "sample" as used herein is used in its broadest sense. A sample suspected of indicating a condition characterized by the dysregulation of apoptotic function may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "modulate" refers to the activity of a compound (e.g., a compound of the present invention) to affect (e.g., to promote or retard) an aspect of cellular function, including, but not limited to, cell growth, proliferation, apoptosis, and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that modulate apoptosis in cells.

General Description of the Invention

As a class of drugs, benzodiazepine compounds have been widely studied and reported to be effective medicaments for treating a number of disease. For example, U.S. Pat. Nos. 4,076,823, 4,110,337, 4,495,101, 4,751,223 and 5,776,946 report that certain benzodiazepine compounds are effective as analgesic and anti-inflammatory agents. Similarly, U.S. Pat. No. 5,324,726 and U.S. Pat. No. 5,597,915 report that certain benzodiazepine compounds are antagonists of cholecystokinin and gastrin and thus might be useful to treat certain gastrointestinal disorders.

Despite the attention benzodiazepine compounds have drawn, it will become apparent from the description below, that the present invention provides novel benzodiazepine compounds and related compounds and methods of using the novel compounds, as well as known compounds, for treating a variety of diseases.

Benzodiazepine compounds are known to bind to benzodiazepine receptors in the central nervous system (CNS) and thus have been used to treat various CNS disorders including anxiety and epilepsy. Peripheral benzodiazepine receptors have also been identified, which receptors may incidentally also be present in the CNS. The present invention demonstrates that benzodiazepines and related compounds have pro-apoptotic and cytotoxic properties useful in the treatment of transformed cells grown in tissue culture. The route of action of these compounds is not through the previously identified benzodiazepine receptors.

Experiments conducted during the development of the present invention have identified novel biological targets for benzodiazepine compounds and related compounds (some of which are related by their ability to bind cellular target molecules rather than their homology to the overall chemical structure of benzodiazepine compounds). In particular, the present invention provides compounds that interact, directly or indirectly, with particular ATPase proteins to elicit the desired biological effects. In some embodiments, the ATPase protein is a mitochondrial ATPase protein. In some embodiments, the ATPase protein is a membrane based (e.g., plasma membrane based) ATPase protein (see, e.g., Tae-Jung Bae, et al., 2004 Proteomics 4:3536; Ki-Burn Kim, et al., 2006 Proteomics 6:2444; Bong-Woo Kim, et al., 2004 Experimental and Molecular Medicine 36:476; Elliot, J. I., et al., 2005 Arthritis Research and Therapy 7:R468; Seiffert, K., et al., 2006 Journal of Investigative Dermatology 126:1017; Pflugers Arch—Eur J. Physiol DOI 10.1007/s00424-006-0069-2; Martinez, L. O., 2003 Nature 421:75; Arakaki, N. 2003 Mol Cancer Res 1:931*9; Moser, T., et al., 1999 Proc Natl Acad Sci USA 96:2811-6; Moser, T., et al., Proc Natl Acad Sci U S A 98:6656-61; Burwick, N., et al., 2005 J Biol Chem 280:1740-5; Das, B., et al., 1994 J Exp Med 180: 273*81; Sulene, L., et al., 2006 Cancer Res. 66:875-82; each of which is herein incorporated by reference in their entireties). Experiments conducted during the course of the present invention demonstrated that compounds of the present invention bind cell membrane ATPase at lower concentrations as compared to mitochondrial ATPase.

Thus, in some embodiments, the present invention provides a number of novel compounds and previously known compounds directed against novel cellular targets to achieve desired biological results. In other embodiments, the present invention provides methods for using such compounds to regulate biological processes. The present invention also provides drug-screening methods to identify and optimize compounds. The present invention further provides diagnostic markers for identifying diseases and conditions, for monitoring treatment regimens, and/or for identifying optimal therapeutic courses of action. These and other research and therapeutic utilities are described below.

Similar benzodiazepine related compounds as described in U.S. Pat. Nos. 7,220,739, 7,144,880 and 7,125,866, and U.S. patent application Ser. Nos. 11/796,039, 11/662,103, 11/591,324, 11/586,097, 11/585,492, 11/445,010, 11/324,419, 11/176,719, 11/110,228, 10/935,333, 10/886,450, 10/795,535, 10/634,114, 10/427,211, 10/217,878, and 09/767,283, and U.S. Provisional Patent Nos. 60/906,167, 60/906,016, 60/878,519, 60/812,270, 60/802,394, 60/732,045, 60/730,711, 60/704,102, 60/686,348, 60/641,040, 60/607,599, 60/565,788, and related patent applications, are also characterized as modulators of cell death.

DETAILED DESCRIPTION OF THE INVENTION

The present invention relates to novel chemical compounds, methods for their discovery, and their therapeutic use. In particular, the present invention provides benzodiazepine derivatives and related compounds and methods of using benzodiazepine derivatives and related compounds as therapeutic agents to treat a number of conditions associated with the faulty regulation of the processes of programmed cell death, autoimmunity, inflammation, hyperproliferation, and the like.

Exemplary compositions and methods of the present invention are described in more detail in the following sections: I. Modulators of Cell Death; II. Exemplary Compounds; III. Pharmaceutical Compositions, Formulations, and Exemplary Administration Routes and Dosing Considerations; IV. Drug Screens; V. Therapeutic Applications; and VI. ATPase Inhibitors and Methods for Identifying Therapeutic Inhibitors.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology"; (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Modulators of Cell Death

In some embodiments, the present invention regulates apoptosis through the exposure of cells to compounds. The effect of compounds can be measured by detecting any number of cellular changes. Cell death may be assayed as described herein and in the art. In some embodiments, cell lines are maintained under appropriate cell culturing conditions (e.g., gas ($CO_2$), temperature and media) for an appropriate period of time to attain exponential proliferation without density dependent constraints. Cell number and or viability are measured using standard techniques, such as trypan blue exclusion/hemo-cytometry, or MTT dye conversion assay. Alternatively, the cell may be analyzed for the expression of genes or gene products associated with aberrations in apoptosis or necrosis.

In some embodiments, exposing the present invention to a cell induces apoptosis. In some embodiments, the present invention causes an initial increase in cellular ROS levels (e.g., $O_2^-$). In further embodiments, exposure of the compounds of the present invention to a cell causes an increase in cellular $O_2^-$ levels. In still further embodiments, the increase in cellular $O_2^-$ levels resulting from the compounds of the present invention is detectable with a redox-sensitive agent that reacts specifically with $O_2^-$ (e.g., dihyroethedium (DHE)).

In other embodiments, increased cellular $O_2^-$ levels resulting from compounds of the present invention diminish after a period of time (e.g., 10 minutes). In other embodiments, increased cellular $O_2^-$ levels resulting from the compounds of the present invention diminish after a period of time and increase again at a later time (e.g., 10 hours). In further embodiments, increased cellular $O_2^-$ levels resulting from the compounds of the present invention diminish at 1 hour and increase again after 4 hours. In some embodiments, an early increase in cellular $O_2^-$ levels, followed by a diminishing in cellular $O_2^-$ levels, followed by another increase in cellular $O_2^-$ levels resulting from the compounds of the present invention is due to different cellular processes (e.g., bimodal cellular mechanisms).

In some embodiments, the present invention causes a collapse of a cell's mitochondrial $\Delta\Psi_m$. In some embodiments, a collapse of a cell's mitochondrial $\Delta\Psi_m$ resulting from the present invention is detectable with a mitochondria-selective potentiometric probe (e.g., $DiOC_6$). In further embodiments, a collapse of a cell's mitochondrial $\Delta\Psi_m$ resulting from the present invention occurs after an initial increase in cellular $O_2^-$ levels.

In some embodiments, the present invention enables caspace activation. In other embodiments, the present invention causes the release of cytochrome c from mitochondria. In further embodiments, the present invention alters cystolic cytochrome c levels. In still other embodiments, altered cystolic cytochrome c levels resulting from the present invention are detectable with immunoblotting cytosolic fractions. In some embodiments, diminished cystolic cytochrome c levels resulting from the present invention are detectable after a period of time (e.g., 10 hours). In further preferred embodiments, diminished cystolic cytochrome c levels resulting from the present invention are detectable after 5 hours.

In other embodiments, the present invention causes the opening of the mitochondrial PT pore. In some embodiments, the cellular release of cytochrome c resulting from the present invention is consistent with a collapse of mitochondrial $\Delta\Psi_m$. In still further preferred embodiments, the present invention causes an increase in cellular $O_2^-$ levels after a mitochondrial $\Delta\Psi_m$ collapse and a release of cytochrome c. In further preferred embodiments, a rise in cellular $O_2^-$ levels is caused by a mitochondrial $\Delta\Psi_m$ collapse and release of cytochrome c resulting from the present invention.

In other embodiments, the present invention causes cellular caspase activation. In some embodiments, caspase activation resulting from the present invention is measurable with a pan-caspase sensitive fluorescent substrate (e.g., FAM-VAD-fmk). In still further embodiments, caspase activation resulting from the present invention tracks with a collapse of mitochondrial $\Delta\Psi_m$. In other embodiments, the present invention causes an appearance of hypodiploid DNA. In some embodiments, an appearance of hypodiploid DNA resulting from the present invention is slightly delayed with respect to caspase activation.

In some embodiments, the molecular target for the present invention is found within mitochondria. In further embodiments, the molecular target of the present invention involves the mitochondrial ATPase. The primary sources of cellular ROS include redox enzymes and the mitochondrial respiratory chain (hereinafter MRC). In some embodiments, cytochrome c oxidase (complex IV of the MRC) inhibitors (e.g., $NaN_3$) preclude a present invention dependent increase in cellular ROS levels. In other preferred embodiments, the ubiquinol-cytochrome c reductase component of MRC complex III inhibitors (e.g., FK506) preclude a present invention dependent increase in ROS levels.

In some embodiments, an increase in cellular ROS levels result from the binding of the compounds of the present invention to a target within mitochondria. In some embodiments, the compounds of the present invention oxidize 2',7'-dichlorodihydrofluorescin (hereinafter DCF) diacetate to DCF. DCF is a redox-active species capable of generating ROS. In further embodiments, the rate of DCF production resulting from the present invention increases after a lag period.

Antimycin A generates $O_2^-$ by inhibiting ubiquinol-cytochrome c reductase. In some embodiments, the present invention increases the rate of ROS production in an equivalent manner to antimycin A. In further embodiments, the present invention increases the rate of ROS production in an equivalent manner to antimycin A under aerobic conditions supporting state 3 respiration. In further embodiments, the compounds of the present invention do not directly target the MPT pore. In additional embodiments, the compounds of the present invention do not generate substantial ROS in the subcellular S15 fraction (e.g., cytosol; microsomes). In even further embodiments, the compounds of the present invention do not stimulate ROS if mitochondria are in state 4 respiration.

MRC complexes I-III are the primary sources of ROS within mitochondria. In some embodiments, the primary source of an increase in cellular ROS levels resulting from the compounds of the present invention emanates from these complexes as a result of inhibiting the $F_1F_0$-ATPase. Indeed, in still further embodiments, the present invention inhibits ATPase activity of bovine sub-mitochondrial particles (hereinafter SMPs). In particularly preferred embodiments, the compounds of the present invention bind to the OSCP component of the $F_1F_0$-ATPase.

Oligomycin is a macrolide natural product that binds to the $F_1F_0$-ATPase, induces a state 3 to 4 transition, and as a result, generates ROS (e.g., $O_2^-$). In some embodiments, the compounds of the present invention bind the OSCP component of the $F_1F_0$-ATPase. In some embodiments, the compounds of the present invention bind the junction between the OSCP and the $F_1$ subunit of the $F_1F_0$-ATPase. In some embodiments, the compounds of the present invention bind the $F_1$ subunit. In certain embodiments, screening assays of the present invention permit detection of binding partners of the OSCP, $F_1$, or OSCP/$F_1$ junction. OSCP is an intrinsically fluorescent protein. In certain embodiments, titrating a solution of test compounds of the present invention into an *E. Coli* sample over-expressed with OSCP results in quenching of the intrinsic OSCP fluorescence. In other embodiments, fluorescent or radioactive test compounds can be used in direct binding assays. In other embodiments, competition binding experiments can be conducted. In this type of assay, test compounds are assessed for their ability to compete with Bz-423 for binding to, for example, the OSCP. In some embodiments, the compounds of the present invention cause a reduced increase in cellular ROS levels and reduced apoptosis in cells through regulation of the OSCP gene (e.g., altering expression of the OSCP gene). In further embodiments, the present invention functions by altering the molecular motions of the ATPase motor.

II. Exemplary Compounds

Exemplary compounds of the present invention are provided below. Any one or more of these compounds can be used to treat a variety of dysregulatory disorders related to cellular death as described elsewhere herein. The compounds can also be used, for example, in drug screening assays and other diagnostic methods.

In one aspect, the invention provides a compound represented by the following formula:

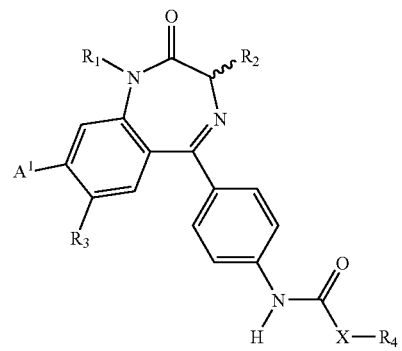

including salts and both R and S enantiomeric forms and racemic mixtures thereof;

wherein $A^1$ is H, Br, Cl, $NO_2$, or $CF_3$;

$R_1$ is $CH_3$ or H;

$R_2$ is

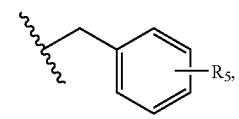 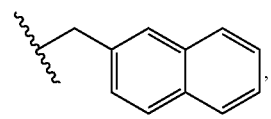

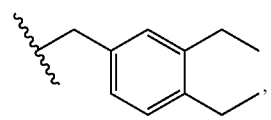 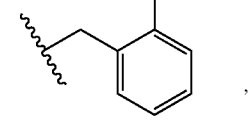

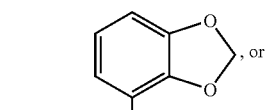 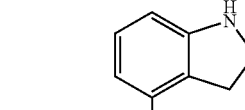

$R_3$ is H, Br, Cl, $NO_2$, or $CF_3$;

$R_4$ is phenyl,

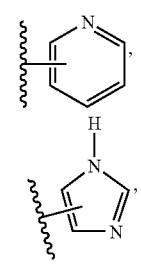 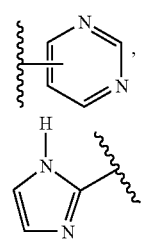 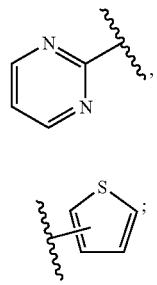

$R_5$ is $CH_3$, $-CH_2CH_3$, $-(CH_2)_2CH_3$, $-CH(CH_3)_2$, $-(CH_2)_3CH_3$, $-C(CH_3)_3$, phenyl, phenoxy, hydroxyphenyl, Br, F or Cl;

$R_6$ is H, Br, Cl, F, $-OCH_3$, or $-OCH(CH_3)_2$;

X is $CH_2$, or NH; and provided that at least one of $A^1$ and $R_3$ is not H.

In certain embodiments, $A^1$ is Cl or $NO_2$; and $R_3$ is H, while in other embodiments, $A^1$ is H; and $R_3$ is Cl or $NO_2$.

In certain embodiments, $R_2$ is

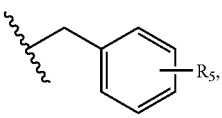 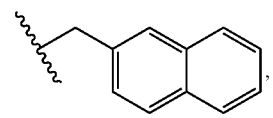

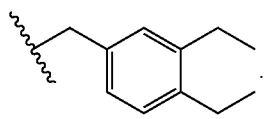

In certain embodiments, X is $CH_2$. In other embodiments, X is NH.

In certain embodiments, $R_4$ is phenyl,

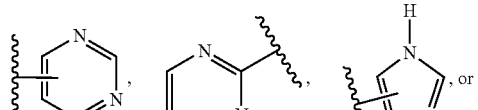

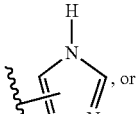

In certain embodiments, the compound is selected from the group consisting of:

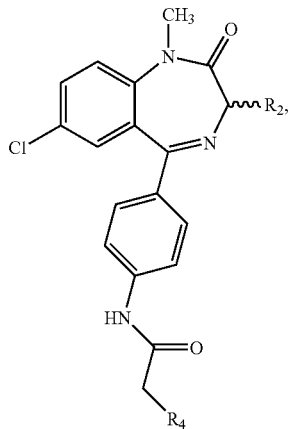

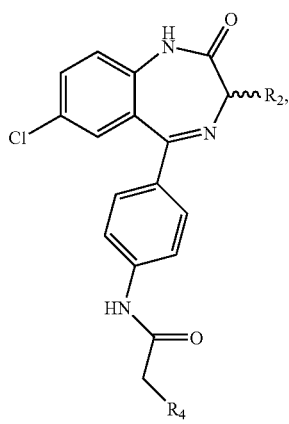

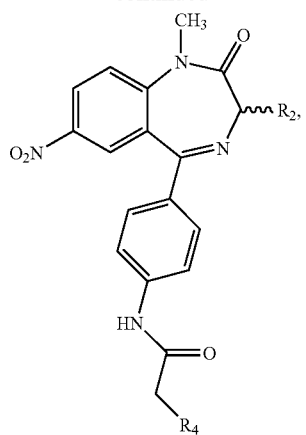
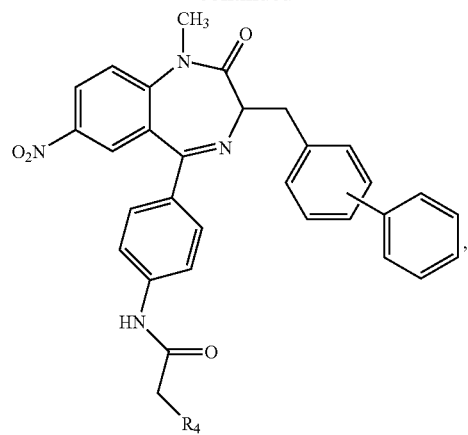
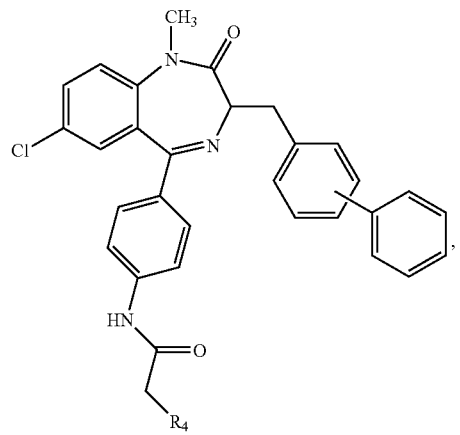
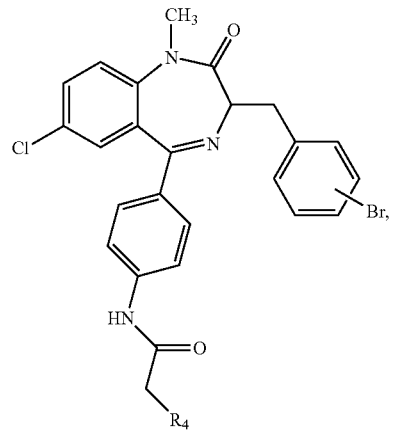
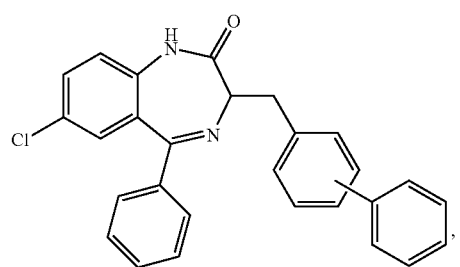
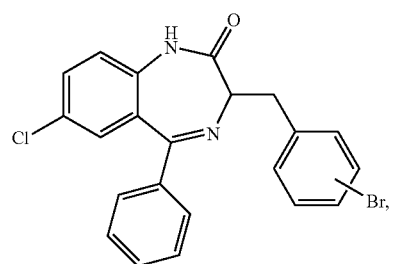

21
-continued
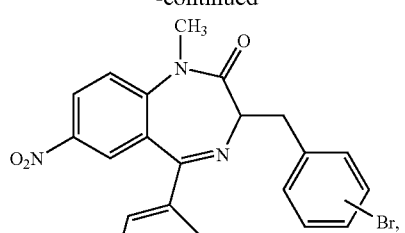
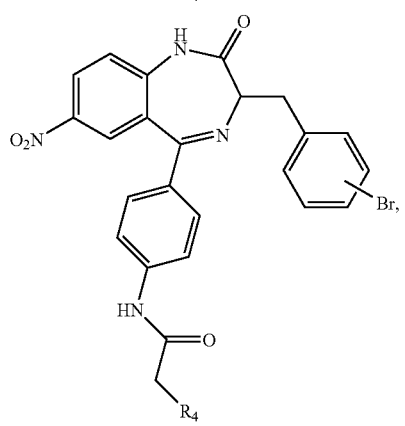
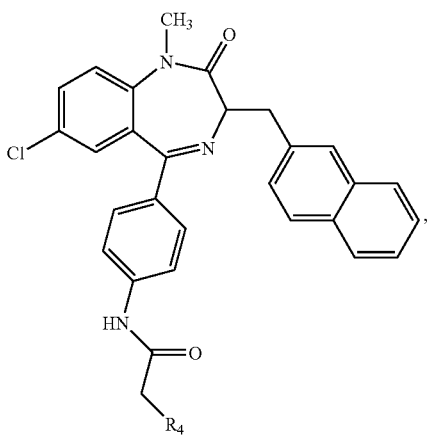
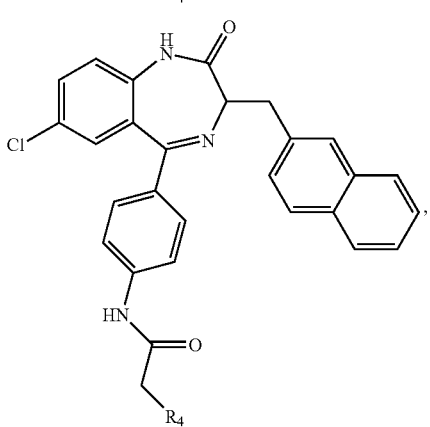
22
-continued
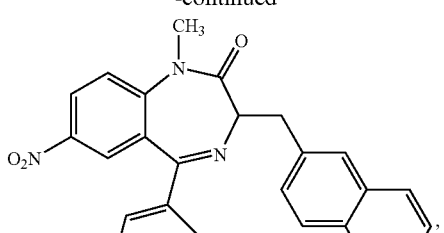
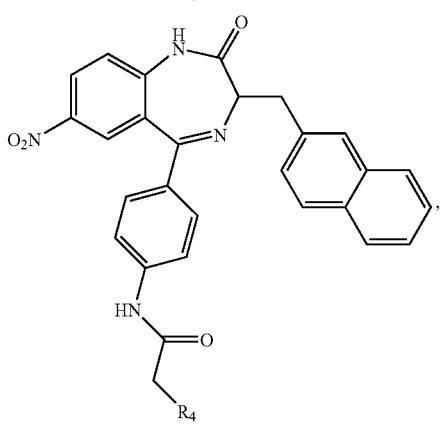
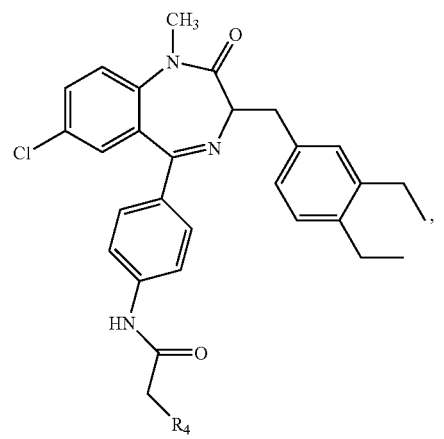
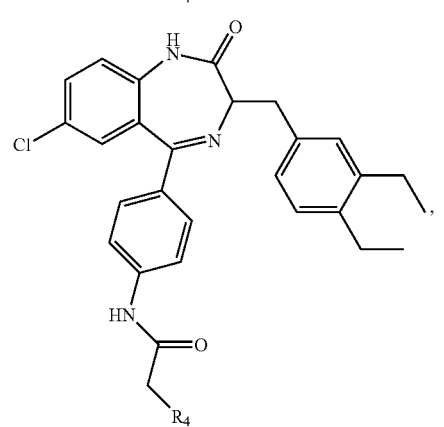

23
-continued
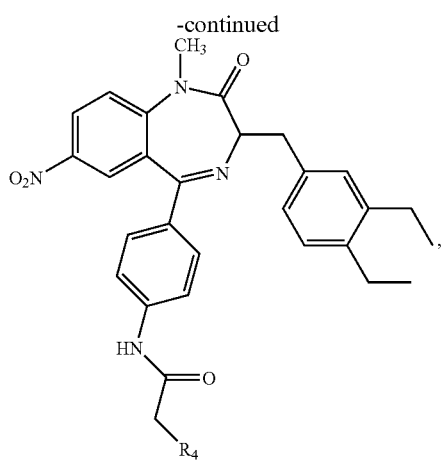
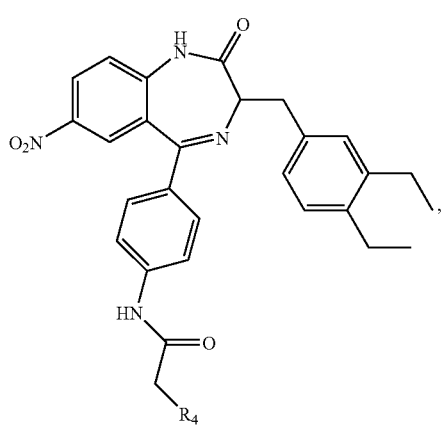
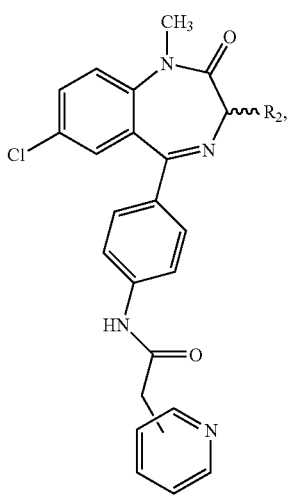
24
-continued
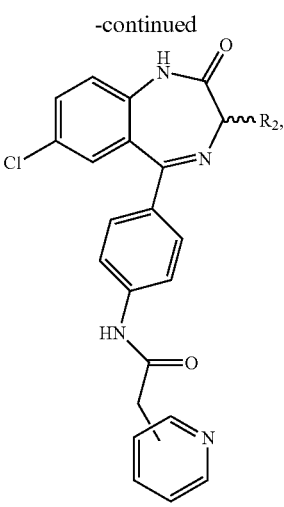
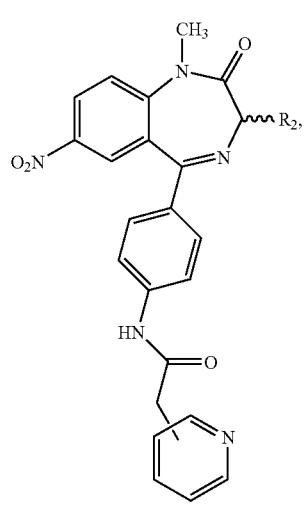
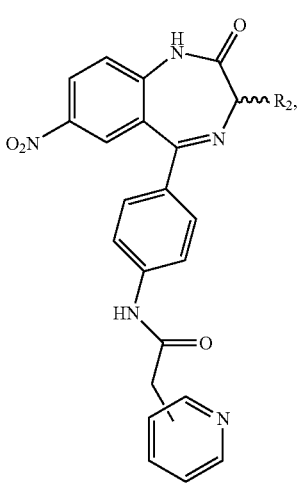

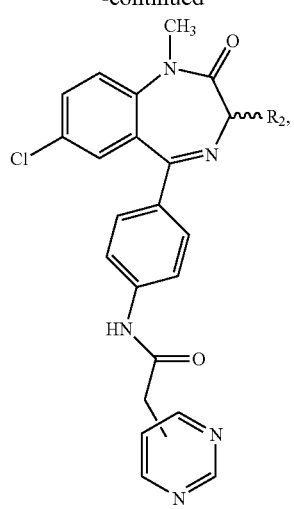
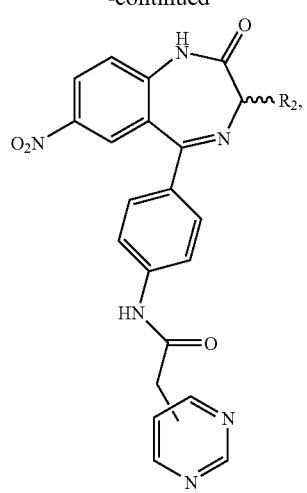
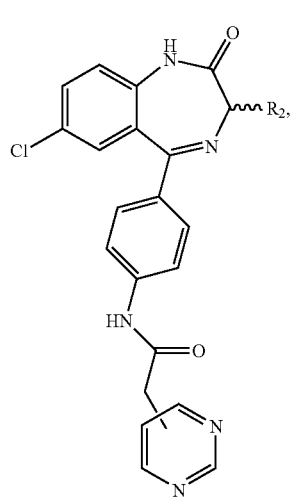
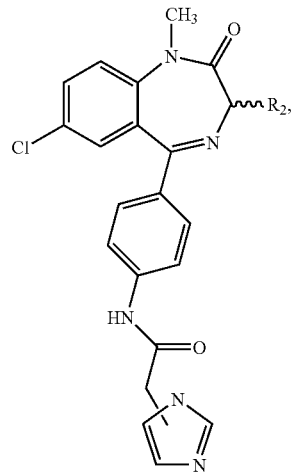
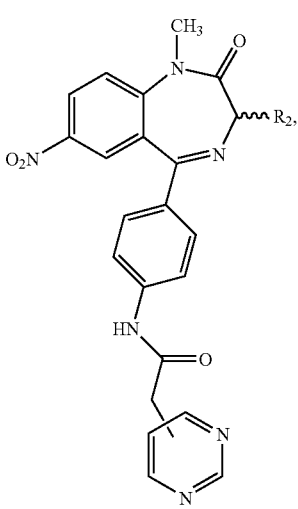
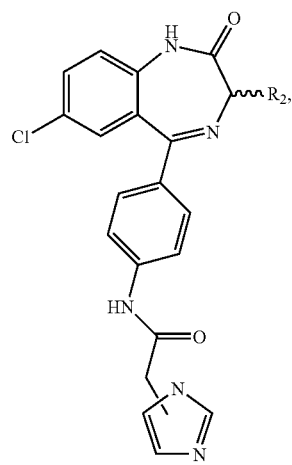

27
-continued
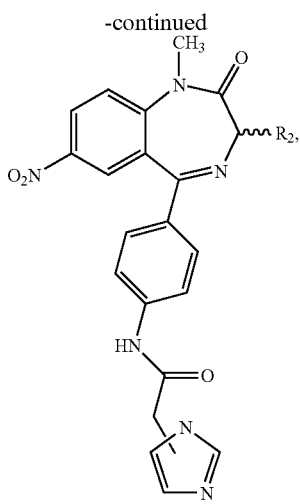
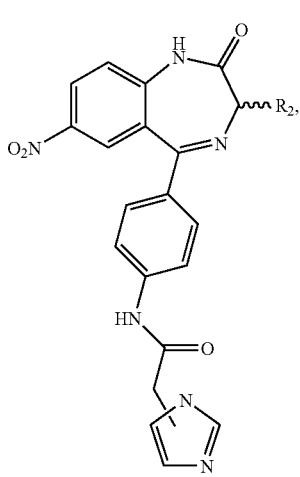
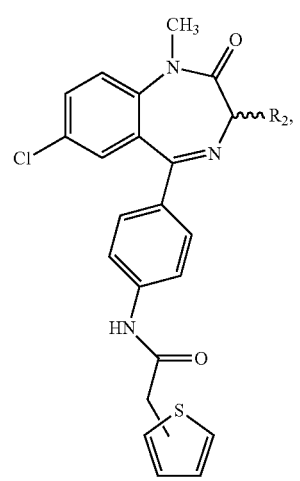
28
-continued
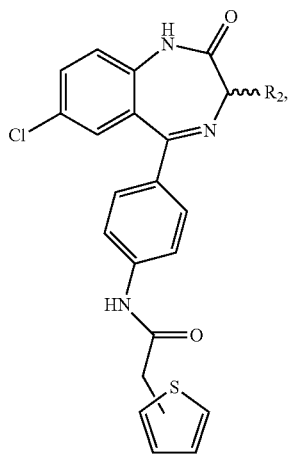
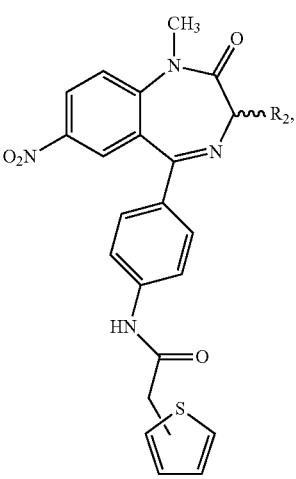
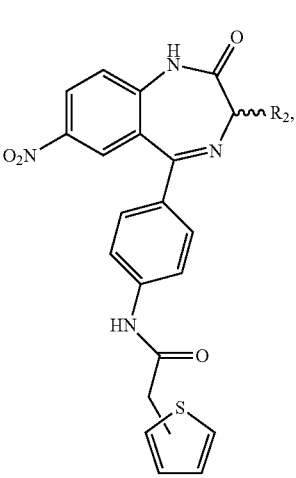

-continued
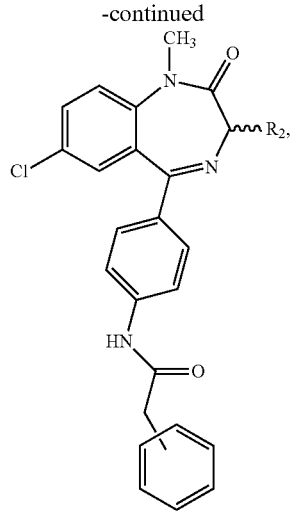
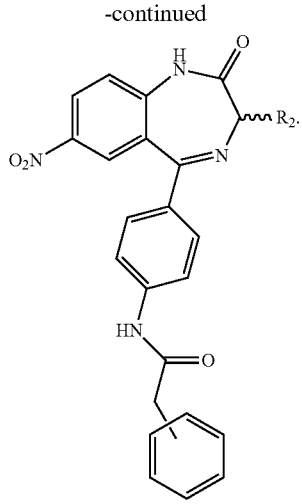
In certain other embodiments, the compound is selected from the group consisting of:
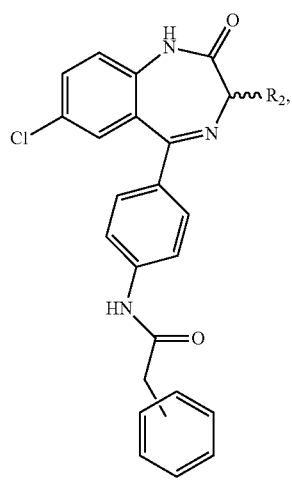
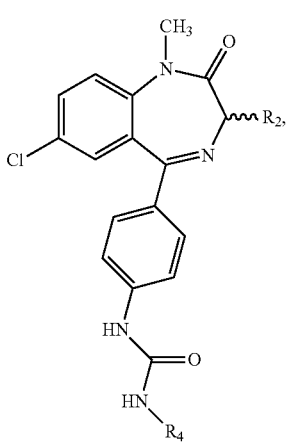
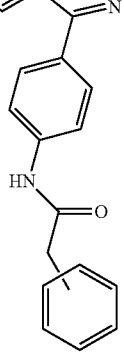
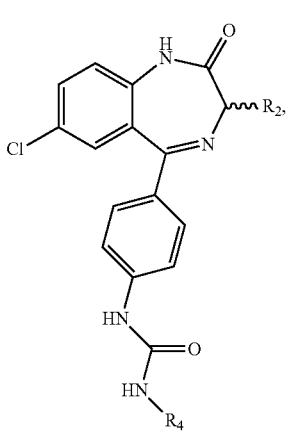

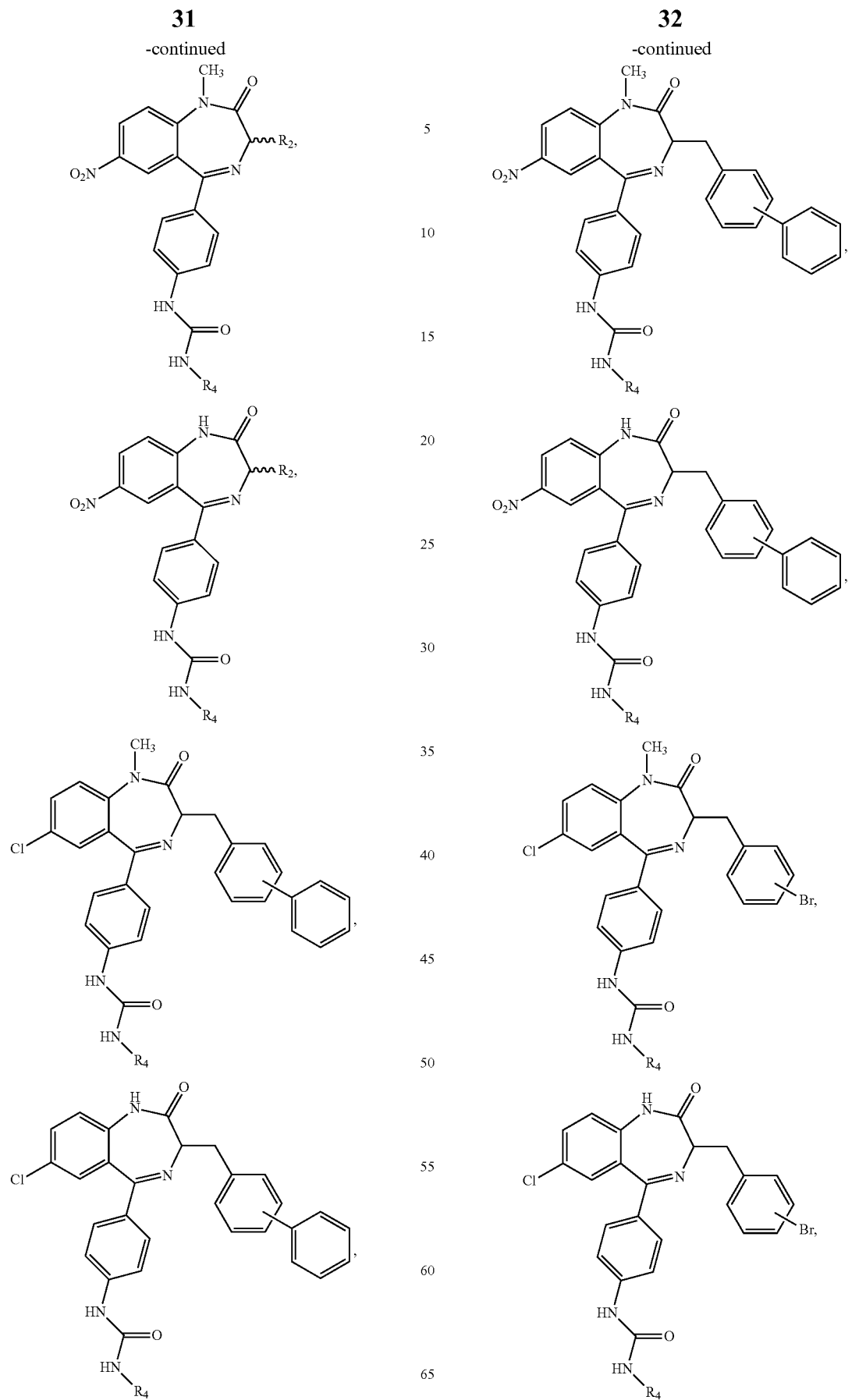

33
-continued
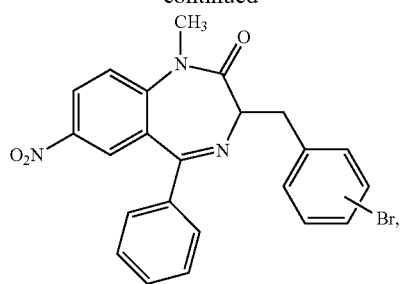
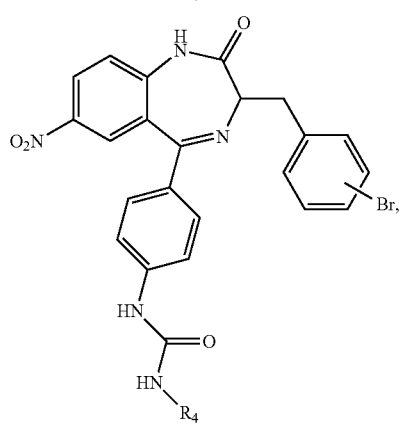
34
-continued
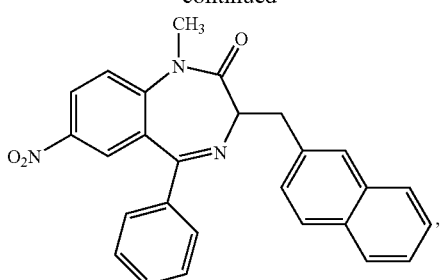
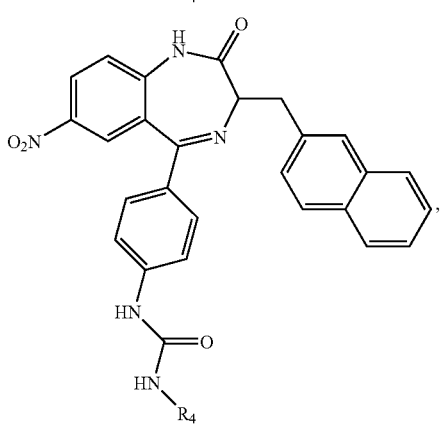
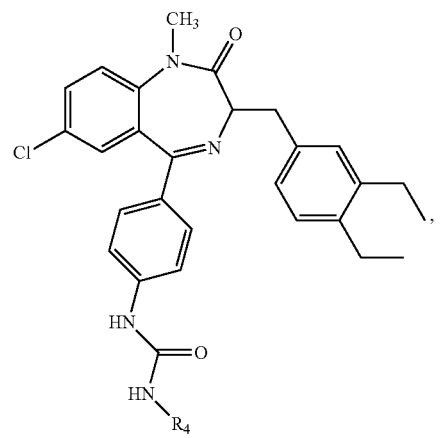
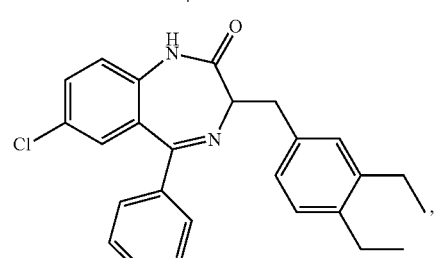

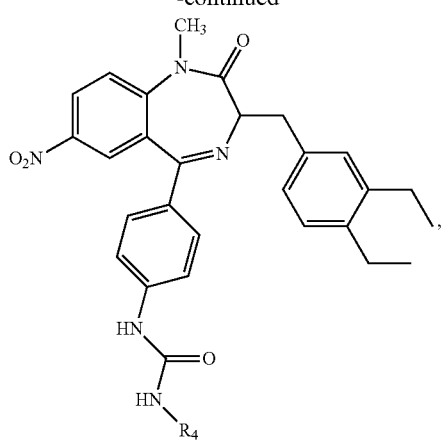
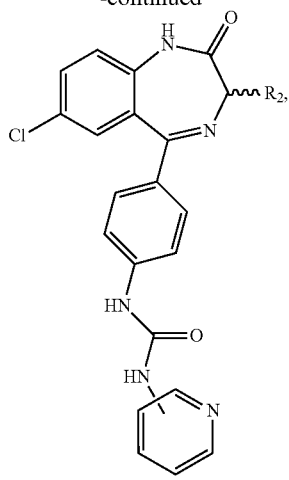
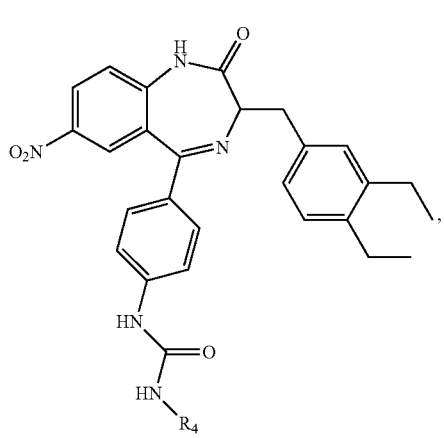
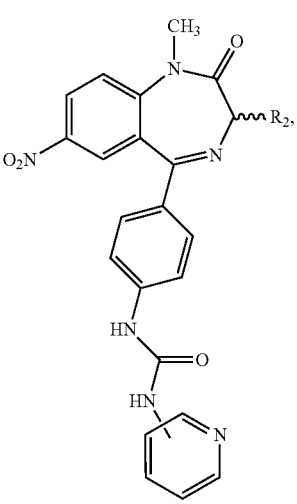
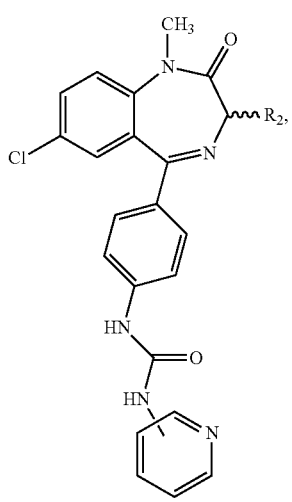
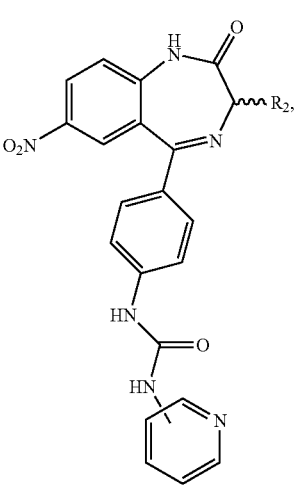

37
-continued
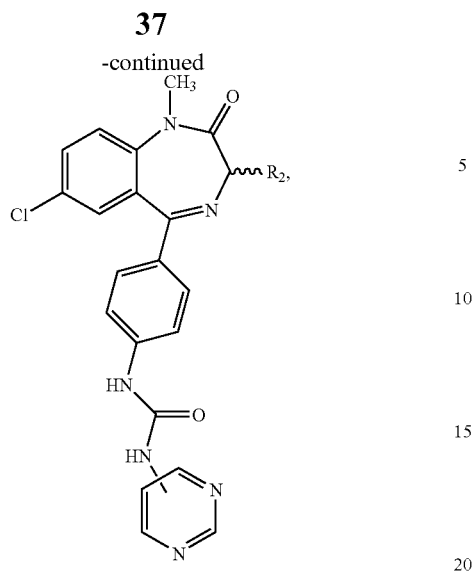
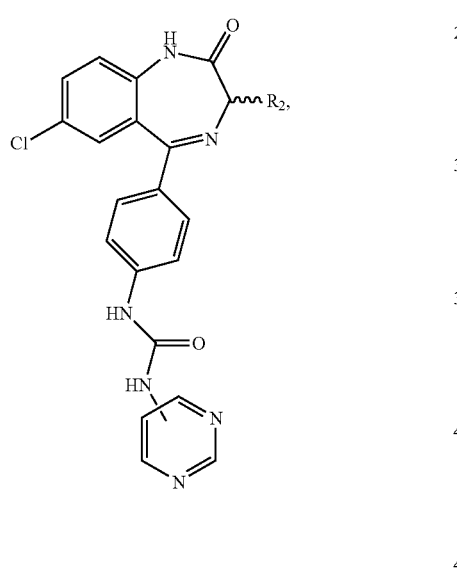
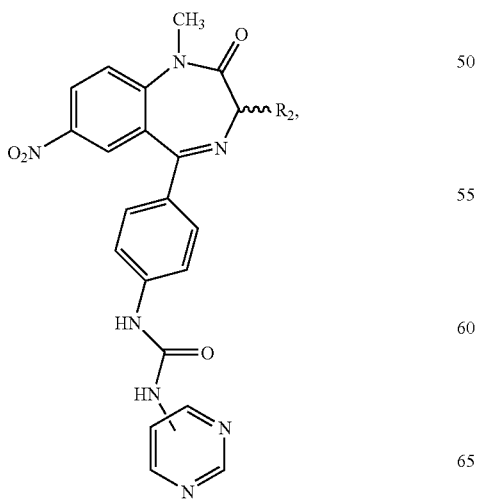
38
-continued
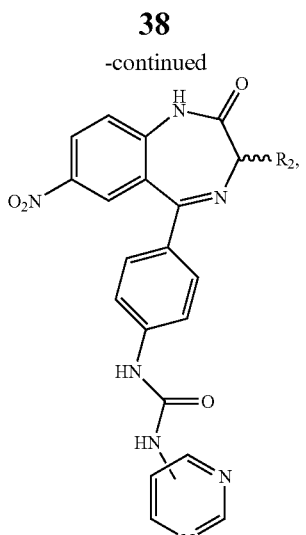
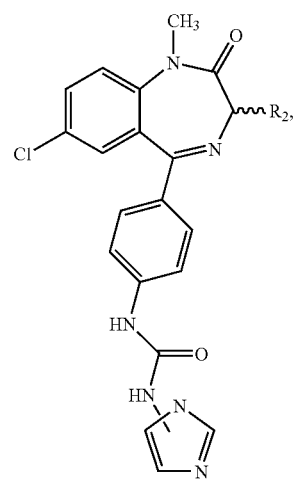
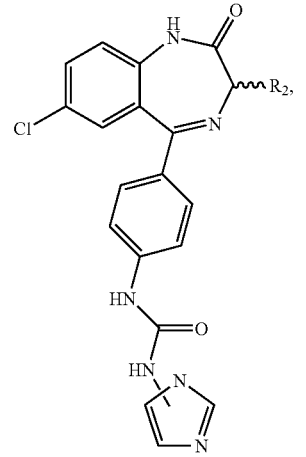

39
-continued
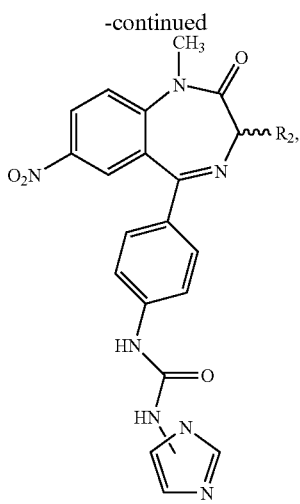
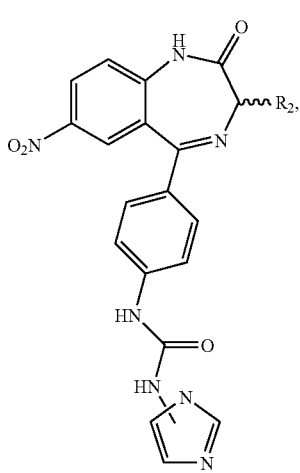
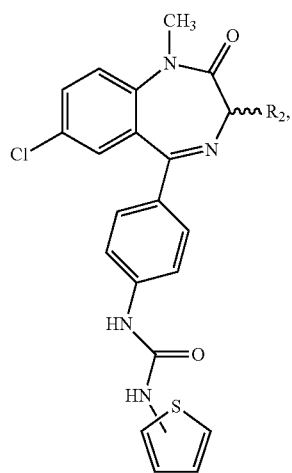
40
-continued
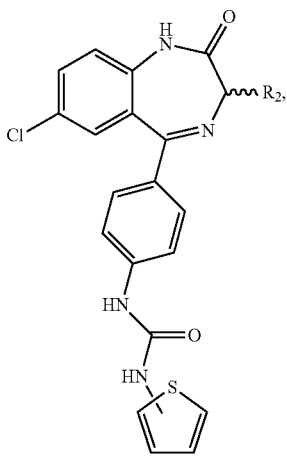
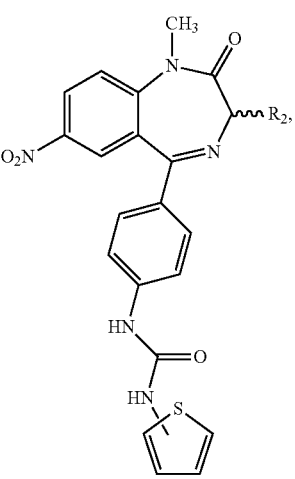
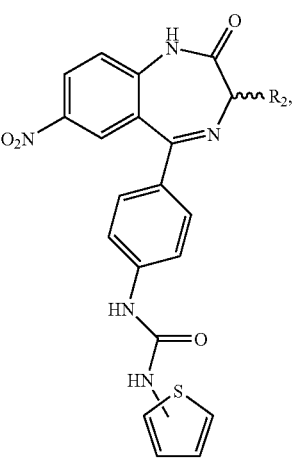

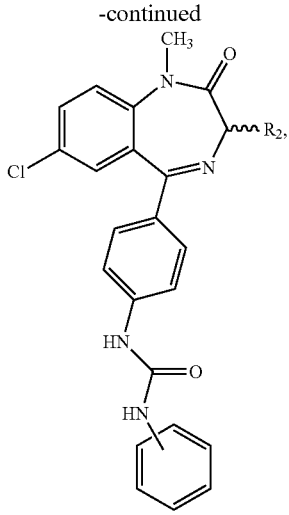
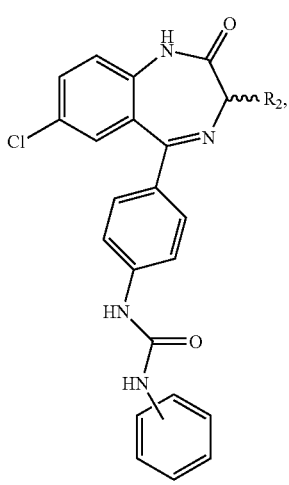
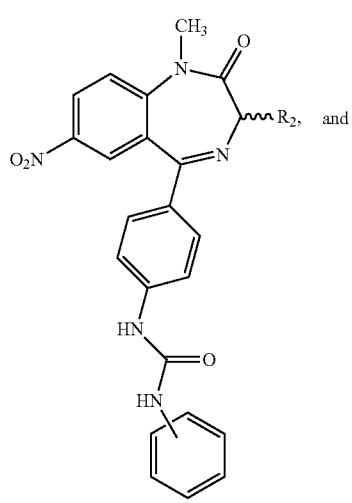
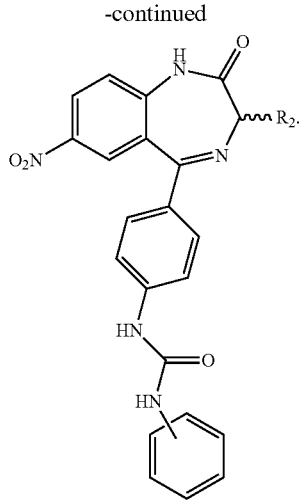
In another embodiment, the invention provides a compound listed in any one of Tables 1, 2, 3, or 4 presented herein.
In another aspect, the invention provides a compound represented by the following formula:
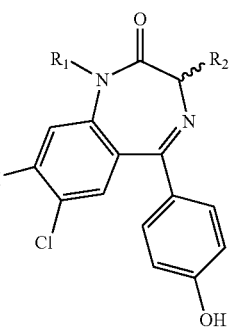
including salts and both R and S enantiomeric forms and racemic mixtures thereof;
wherein
R₁ is CH₃ or H;
R₂ is
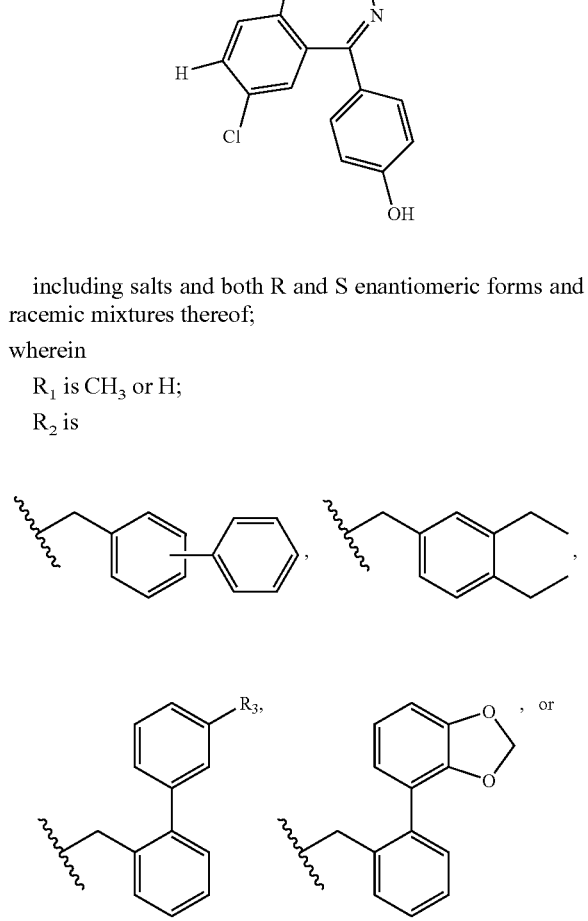

-continued
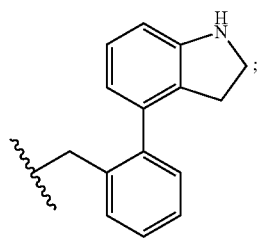
$R_3$ is Br, Cl, F, —OCH$_3$, or —OCH(CH$_3$)$_2$.
In certain embodiments, $R_2$ is
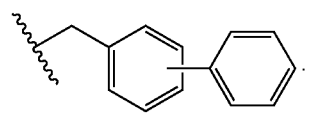
In certain embodiments, the compound is selected from the group consisting of:
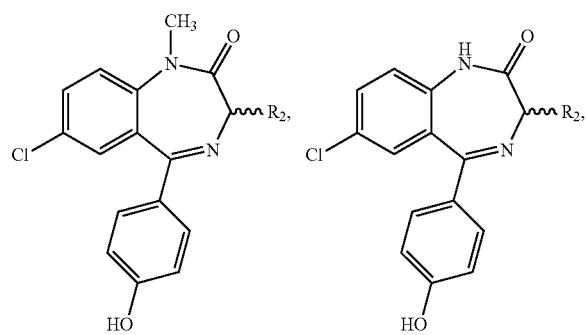
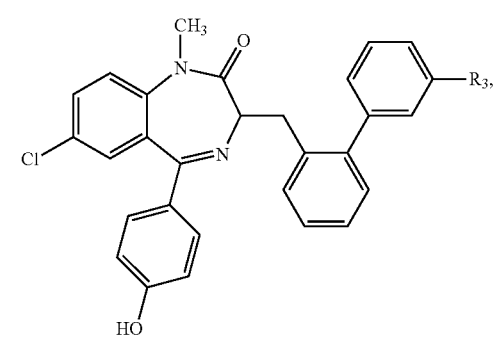
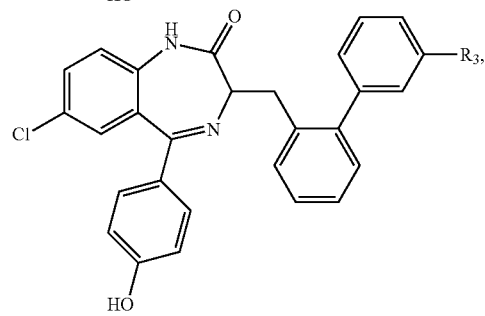
-continued
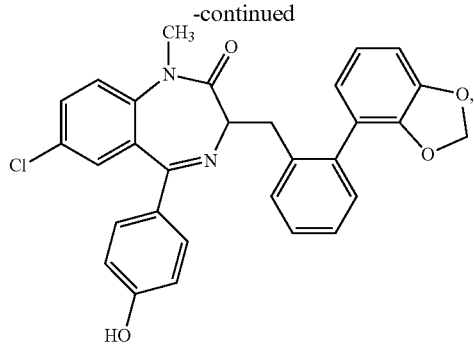
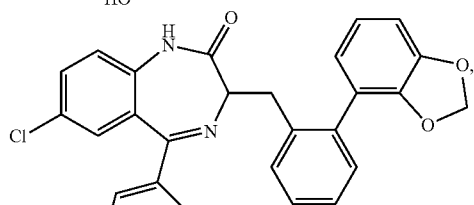
and
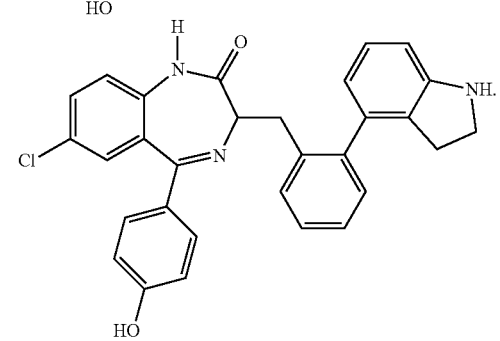
In another aspect, the invention provides a compound represented by the following formula:
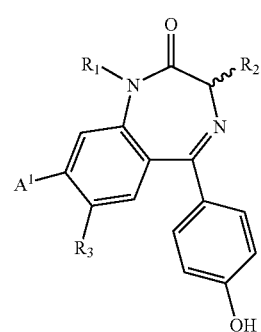

including salts and both R and S enantiomeric forms and racemic mixtures thereof;

wherein

A$^1$ is H or Cl;

R$_1$ is H or CH$_3$;

R$_2$ is

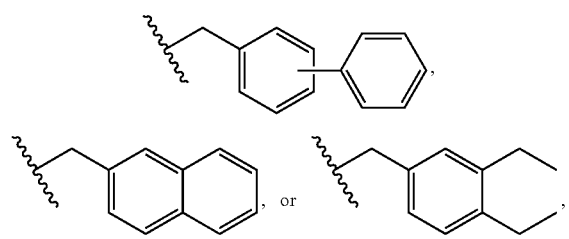

R$_3$ is H or Br; and provided that at least one of A$^1$ and R$_3$ is not H.

In certain embodiments, A$^1$ is H, and R$_3$ is Br.

In certain embodiments, the compound is selected from the group consisting of:

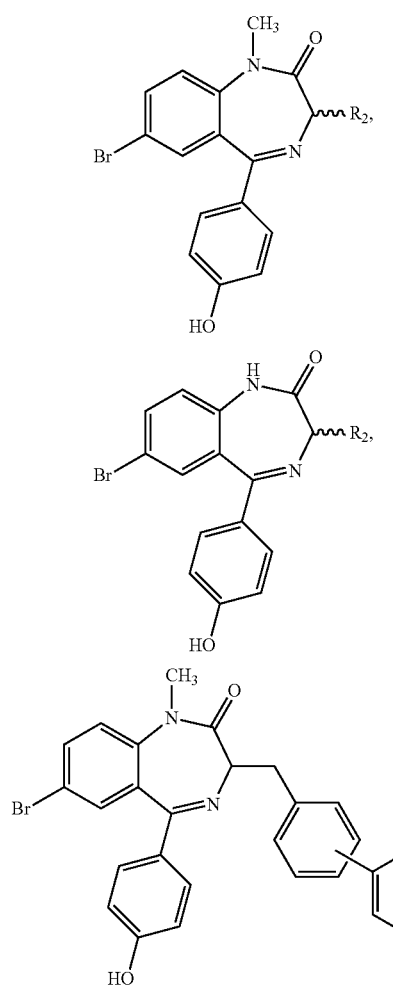

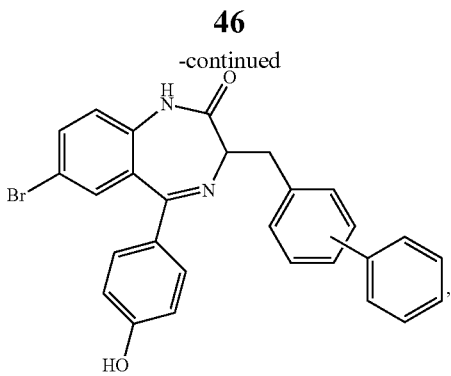

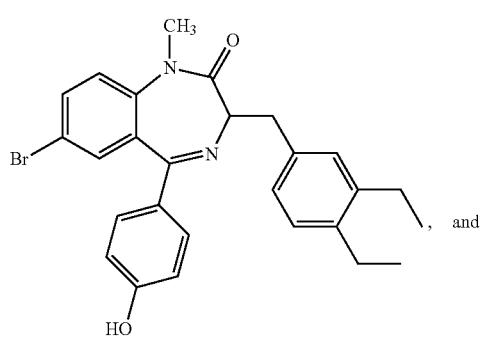

In another aspect, the invention provides a compound represented by the following formula:

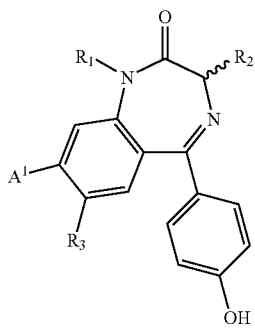

including salts and both R and S enantiomeric forms and racemic mixtures thereof;

wherein
A¹ is H or —NO₂;
R₁ is H or CH₃;
R₂ is
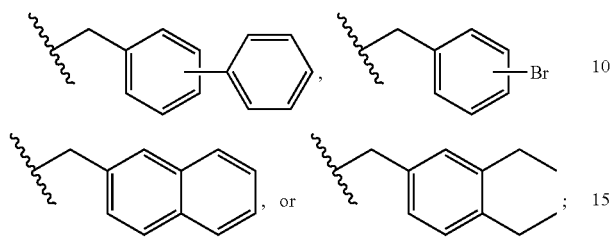
R₃ is H, —NO₂, or CF₃; and
provided that at least one of A¹ and R₃ is not H.
In certain embodiments, A¹ is H; and R₃ is —NO₂, or CF₃.
In certain embodiments, the compound is selected from the group consisting of:
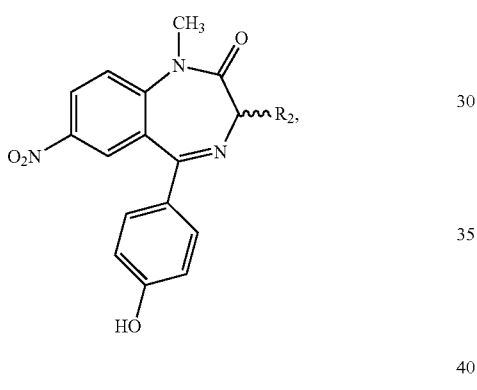
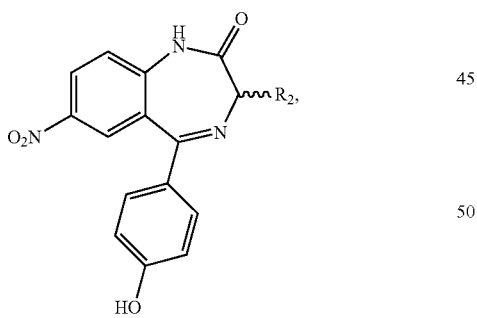
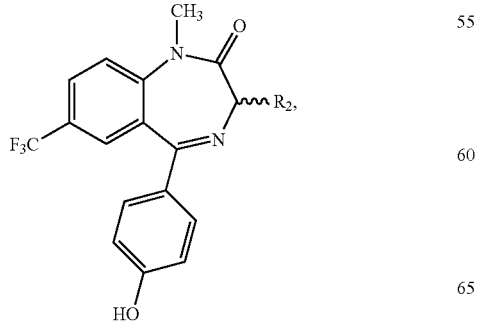
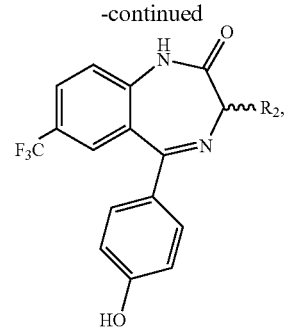
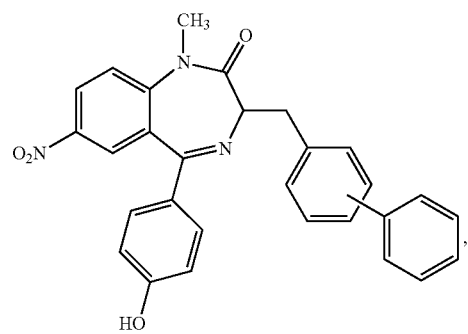
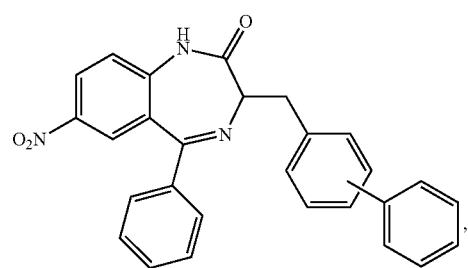
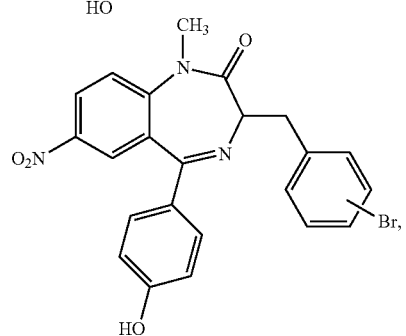
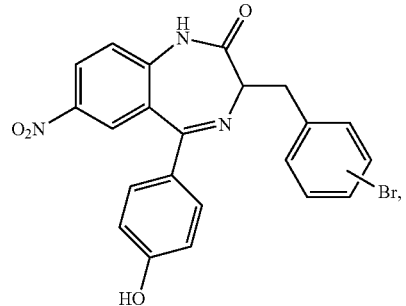

-continued
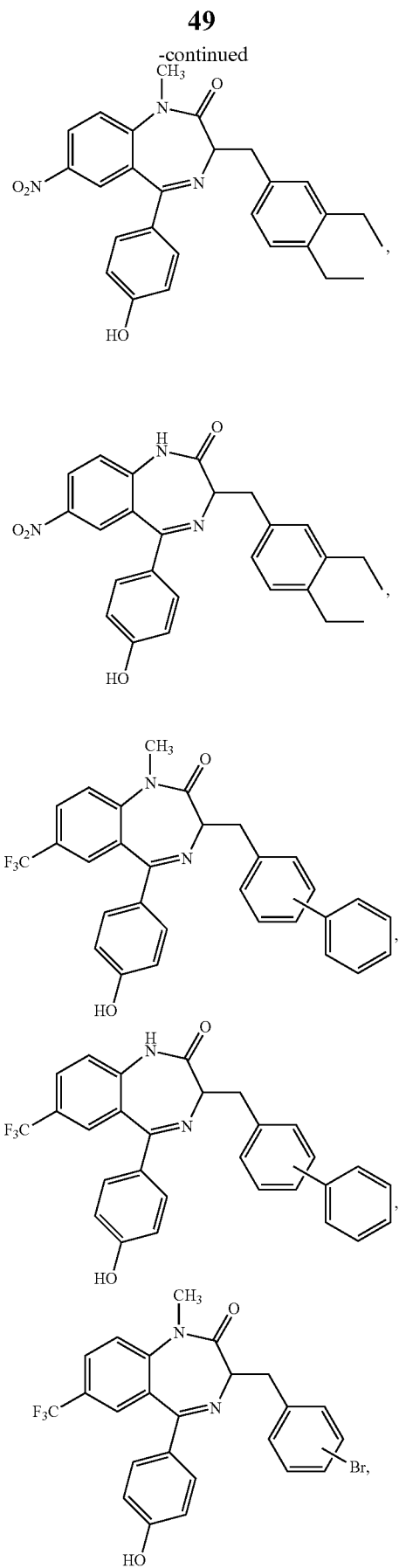
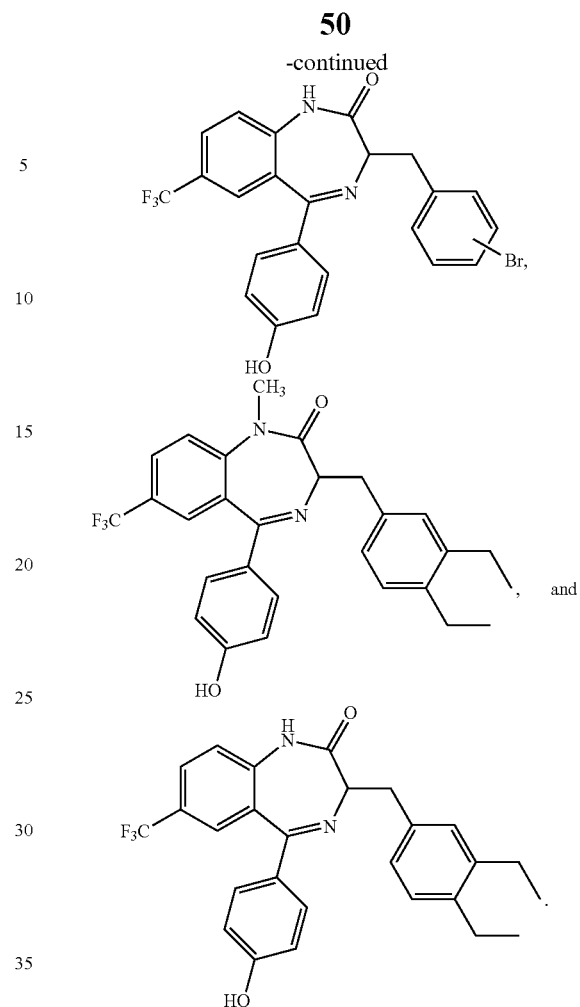
In certain embodiments, the compounds are as described in the following tables.
TABLE 1
| Compound No. | $R^1$ | $R^2$ | $R^3$ | $R^4$ |
|---|---|---|---|---|
| 1 | Cl | H | optionally substituted aryl | aryl or heteroaryl |
| 2 | —NO$_2$ | H | optionally substituted aryl | aryl or heteroaryl |
| 3 | Cl | alkyl | optionally substituted aryl | aryl or heteroaryl |
| 4 | —NO$_2$ | alkyl | optionally substituted aryl | aryl or heteroaryl |

TABLE 1-continued

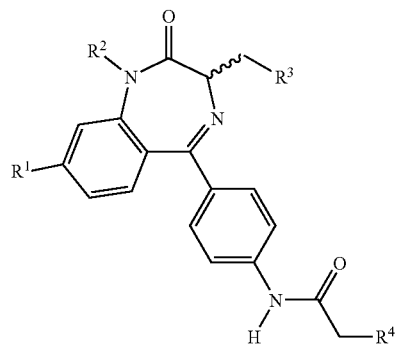

| Compound No. | R¹ | R² | R³ | R⁴ |
|---|---|---|---|---|
| 5 | Cl | H | 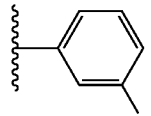 | phenyl |
| 6 | Cl | H |  | phenyl |
| 7 | Cl | H | 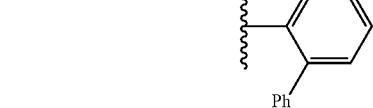 | phenyl |
| 8 | Cl | H | ortho-bromo phenyl | phenyl |
| 9 | Cl | H | meta-bromo phenyl | phenyl |
| 10 | Cl | H | para-bromo phenyl | phenyl |
| 11 | Cl | H | naphthyl | phenyl |
| 12 | Cl | H | 3,4-diethylphenyl | phenyl |
| 13 | Cl | H | 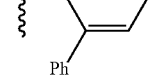 | 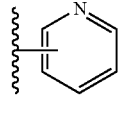 |
| 14 | Cl | H | 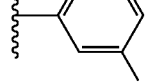 | 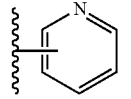 |
| 15 | Cl | H |  | 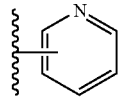 |
| 16 | Cl | H | ortho-bromo phenyl |  |
| 17 | Cl | H | meta-bromo phenyl |  |

TABLE 1-continued

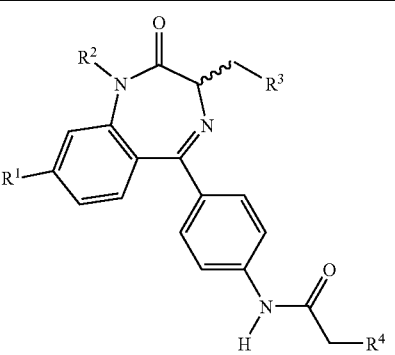

| Compound No. | R¹ | R² | R³ | R⁴ |
|---|---|---|---|---|
| 18 | Cl | H | para-bromo phenyl | 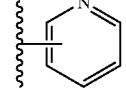 |
| 19 | Cl | H | naphthyl | 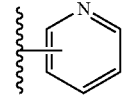 |
| 20 | Cl | H | 3,4-diethylphenyl | 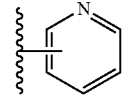 |
| 21 | Cl | H | 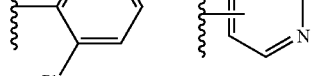 | |
| 22 | Cl | H |  | |
| 23 | Cl | H | 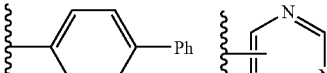 | |
| 24 | Cl | H | ortho-bromo phenyl | 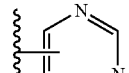 |
| 25 | Cl | H | meta-bromo phenyl | 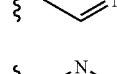 |
| 26 | Cl | H | para-bromo phenyl | 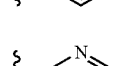 |

TABLE 1-continued

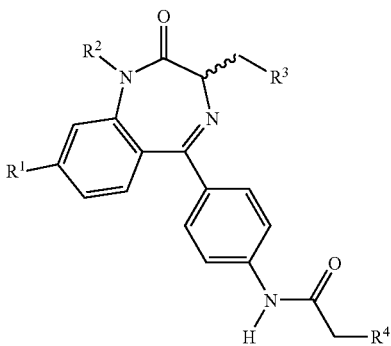

| Compound No. | R¹ | R² | R³ | R⁴ |
|---|---|---|---|---|
| 27 | Cl | H | naphthyl | pyrimidinyl |
| 28 | Cl | H | 3,4-diethylphenyl | pyrimidinyl |
| 29 | Cl | H | 2-Ph-phenyl | imidazolyl |
| 30 | Cl | H | 3-Ph-phenyl | imidazolyl |
| 31 | Cl | H | 4-Ph-phenyl | imidazolyl |
| 32 | Cl | H | ortho-bromo phenyl | imidazolyl |
| 33 | Cl | H | meta-bromo phenyl | imidazolyl |
| 34 | Cl | H | para-bromo phenyl | imidazolyl |

TABLE 1-continued

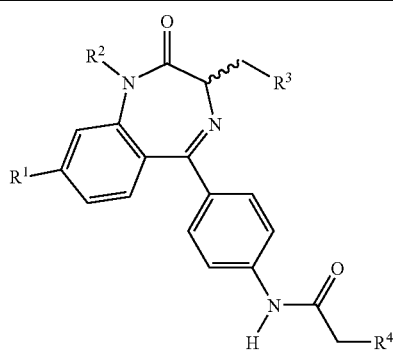

| Compound No. | R¹ | R² | R³ | R⁴ |
|---|---|---|---|---|
| 35 | Cl | H | naphthyl | imidazolyl |
| 36 | Cl | H | 3,4-diethylphenyl | imidazolyl |
| 37 | Cl | H | 2-Ph-phenyl | thienyl |
| 38 | Cl | H | 3-Ph-phenyl | thienyl |
| 39 | Cl | H | 4-Ph-phenyl | thienyl |
| 40 | Cl | H | ortho-bromo phenyl | thienyl |
| 41 | Cl | H | meta-bromo phenyl | thienyl |
| 42 | Cl | H | para-bromo phenyl | thienyl |

TABLE 1-continued

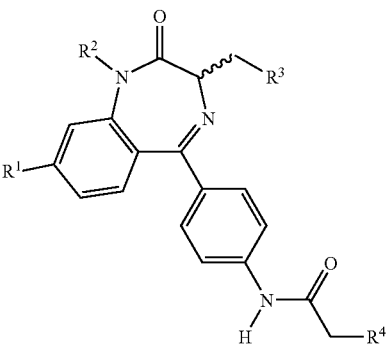

| Compound No. | R¹ | R² | R³ | R⁴ |
|---|---|---|---|---|
| 43 | Cl | H | naphthyl |  |
| 44 | Cl | H | 3,4-diethylphenyl |  |
| 45 | —NO₂ | H | 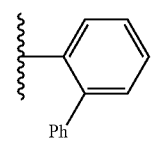 | phenyl |
| 46 | —NO₂ | H | 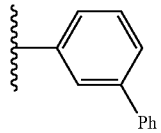 | phenyl |
| 47 | —NO₂ | H | 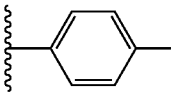 | phenyl |
| 48 | —NO₂ | H | ortho-bromo phenyl | phenyl |
| 49 | —NO₂ | H | meta-bromo phenyl | phenyl |
| 50 | —NO₂ | H | para-bromo phenyl | phenyl |
| 51 | —NO₂ | H | naphthyl | phenyl |
| 52 | —NO₂ | H | 3,4-diethylphenyl | phenyl |
| 53 | —NO₂ | H | 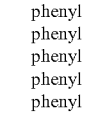 | 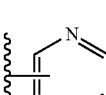 |
| 54 | —NO₂ | H | 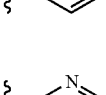 | 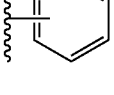 |
| 55 | —NO₂ | H | 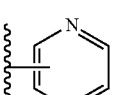 | 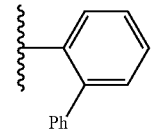 |

TABLE 1-continued

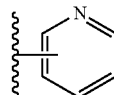

| Compound No. | R¹ | R² | R³ | R⁴ |
|---|---|---|---|---|
| 56 | —NO₂ | H | ortho-bromo phenyl | 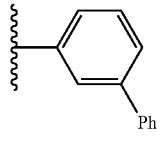 |
| 57 | —NO₂ | H | meta-bromo phenyl | 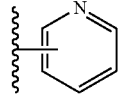 |
| 58 | —NO₂ | H | para-bromo phenyl | 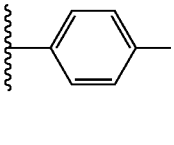 |
| 59 | —NO₂ | H | naphthyl | 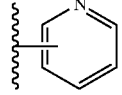 |
| 60 | —NO₂ | H | 3,4-diethylphenyl | 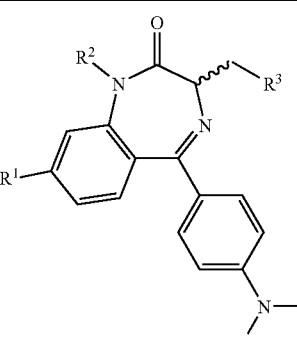 |
| 61 | —NO₂ | H | 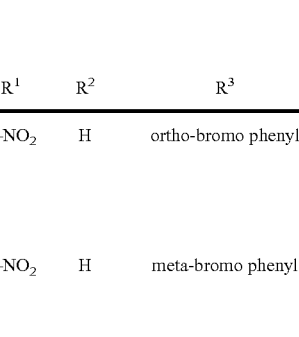 | 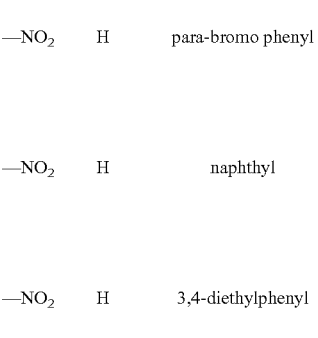 |
| 62 | —NO₂ | H | 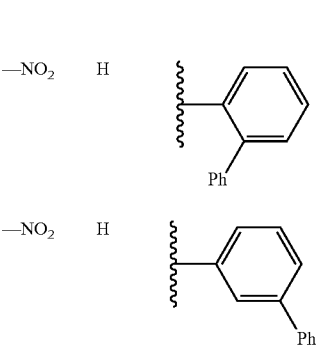 | 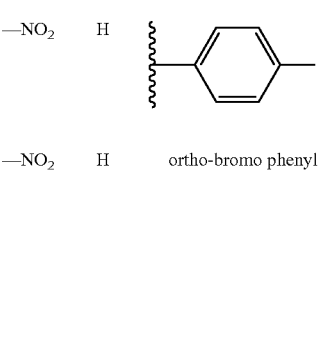 |
| 63 | —NO₂ | H |  |  |
| 64 | —NO₂ | H | ortho-bromo phenyl |  |

TABLE 1-continued

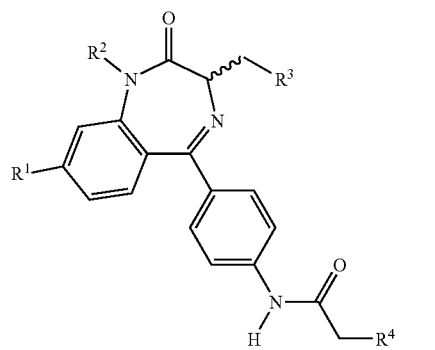

| Compound No. | R¹ | R² | R³ | R⁴ |
|---|---|---|---|---|
| 65 | —NO$_2$ | H | meta-bromo phenyl | pyrimidinyl |
| 66 | —NO$_2$ | H | para-bromo phenyl | pyrimidinyl |
| 67 | —NO$_2$ | H | naphthyl | pyrimidinyl |
| 68 | —NO$_2$ | H | 3,4-diethylphenyl | pyrimidinyl |
| 69 | —NO$_2$ | H | ortho-Ph-phenyl | imidazolyl |
| 70 | —NO$_2$ | H | meta-Ph-phenyl | imidazolyl |
| 71 | —NO$_2$ | H | para-Ph-phenyl | imidazolyl |
| 72 | —NO$_2$ | H | ortho-bromo phenyl | imidazolyl |

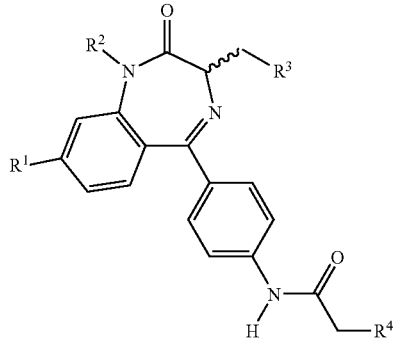

| Compound No. | R¹ | R² | R³ | R⁴ |
|---|---|---|---|---|
| 73 | —NO$_2$ | H | meta-bromo phenyl | imidazolyl |
| 74 | —NO$_2$ | H | para-bromo phenyl | imidazolyl |
| 75 | —NO$_2$ | H | naphthyl | imidazolyl |
| 76 | —NO$_2$ | H | 3,4-diethylphenyl | imidazolyl |
| 77 | —NO$_2$ | H | ortho-Ph-phenyl | thienyl |
| 78 | —NO$_2$ | H | meta-Ph-phenyl | thienyl |
| 79 | —NO$_2$ | H | para-Ph-phenyl | thienyl |
| 80 | —NO$_2$ | H | ortho-bromo phenyl | thienyl |

TABLE 1-continued

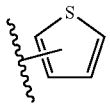

| Compound No. | R¹ | R² | R³ | R⁴ |
|---|---|---|---|---|
| 81 | —NO₂ | H | meta-bromo phenyl | 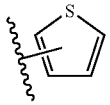 thienyl |
| 82 | —NO₂ | H | para-bromo phenyl |  thienyl |
| 83 | —NO₂ | H | naphthyl |  thienyl |
| 84 | —NO₂ | H | 3,4-diethylphenyl | 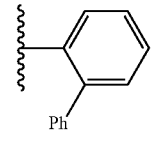 thienyl |
| 85 | Cl | methyl | 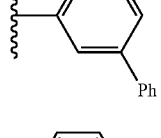 ortho-Ph-phenyl | phenyl |
| 86 | Cl | methyl | 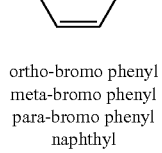 meta-Ph-phenyl | phenyl |
| 87 | Cl | methyl | 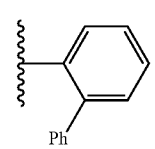 para-Ph-phenyl | phenyl |
| 88 | Cl | methyl | ortho-bromo phenyl | phenyl |
| 89 | Cl | methyl | meta-bromo phenyl | phenyl |
| 90 | Cl | methyl | para-bromo phenyl | phenyl |
| 91 | Cl | methyl | naphthyl | phenyl |
| 92 | Cl | methyl | 3,4-diethylphenyl | phenyl |
| 93 | Cl | methyl | 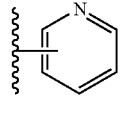 ortho-Ph-phenyl | 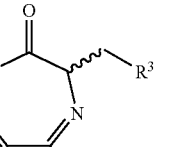 pyridyl |
| 94 | Cl | methyl |  meta-Ph-phenyl | 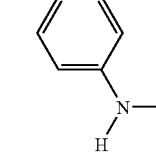 pyridyl |
| 95 | Cl | methyl |  para-Ph-phenyl | 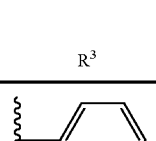 pyridyl |
| 96 | Cl | methyl | ortho-bromo phenyl | 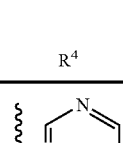 pyridyl |
| 97 | Cl | methyl | meta-bromo phenyl | 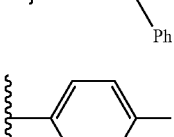 pyridyl |
| 98 | Cl | methyl | para-bromo phenyl | 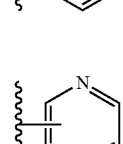 pyridyl |
| 99 | Cl | methyl | naphthyl | 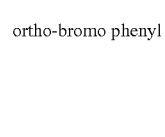 pyridyl |
| 100 | Cl | methyl | 3,4-diethylphenyl | 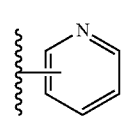 pyridyl |
| 101 | Cl | methyl | 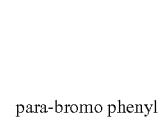 ortho-Ph-phenyl | 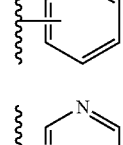 pyrimidyl |
| 102 | Cl | methyl | 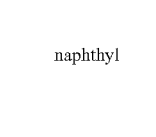 meta-Ph-phenyl | 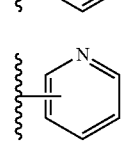 pyrimidyl |

TABLE 1-continued

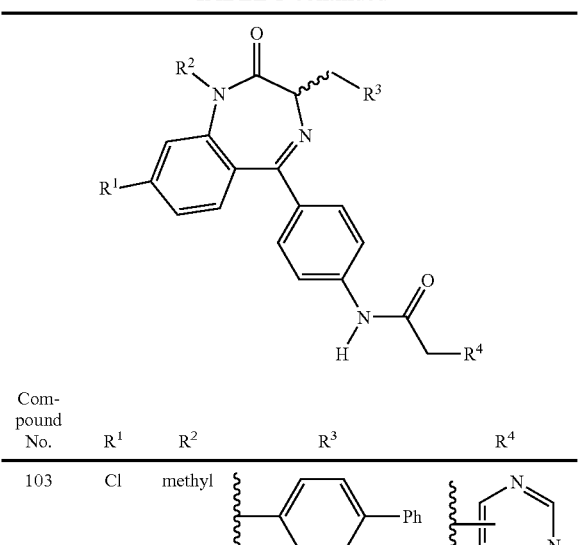

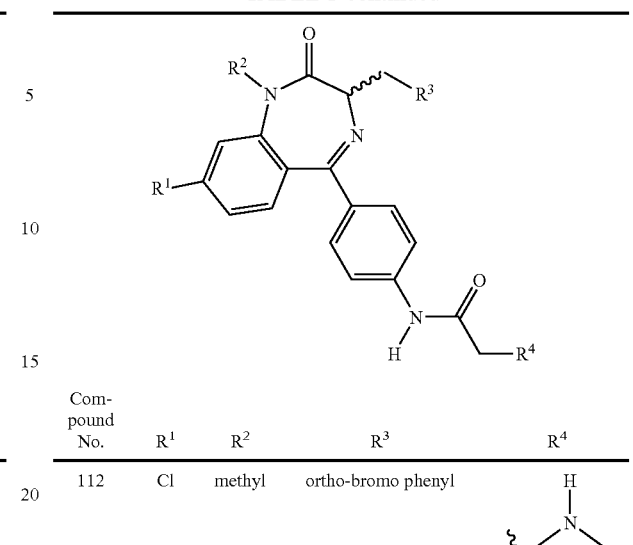

| Compound No. | R¹ | R² | R³ | R⁴ |
|---|---|---|---|---|
| 103 | Cl | methyl | 4-phenylphenyl | pyrimidinyl |
| 104 | Cl | methyl | ortho-bromo phenyl | pyrimidinyl |
| 105 | Cl | methyl | meta-bromo phenyl | pyrimidinyl |
| 106 | Cl | methyl | para-bromo phenyl | pyrimidinyl |
| 107 | Cl | methyl | naphthyl | pyrimidinyl |
| 108 | Cl | methyl | 3,4-diethylphenyl | pyrimidinyl |
| 109 | Cl | methyl | 2-phenylphenyl | imidazolyl |
| 110 | Cl | methyl | 3-phenylphenyl | imidazolyl |
| 111 | Cl | methyl | 4-phenylphenyl | imidazolyl |

| Compound No. | R¹ | R² | R³ | R⁴ |
|---|---|---|---|---|
| 112 | Cl | methyl | ortho-bromo phenyl | imidazolyl |
| 113 | Cl | methyl | meta-bromo phenyl | imidazolyl |
| 114 | Cl | methyl | para-bromo phenyl | imidazolyl |
| 115 | Cl | methyl | naphthyl | imidazolyl |
| 116 | Cl | methyl | 3,4-diethylphenyl | imidazolyl |
| 117 | Cl | methyl | 2-phenylphenyl | thienyl |
| 118 | Cl | methyl | 3-phenylphenyl | thienyl |
| 119 | Cl | methyl | 4-phenylphenyl | thienyl |

TABLE 1-continued

[Structure: benzodiazepinone with R¹, R², R³ substituents and a 4-(NHC(O)CH₂R⁴)phenyl group]

| Compound No. | R¹ | R² | R³ | R⁴ |
|---|---|---|---|---|
| 120 | Cl | methyl | ortho-bromo phenyl | thienyl |
| 121 | Cl | methyl | meta-bromo phenyl | thienyl |
| 122 | Cl | methyl | para-bromo phenyl | thienyl |
| 123 | Cl | methyl | naphthyl | thienyl |
| 124 | Cl | methyl | 3,4-diethylphenyl | thienyl |
| 125 | —NO₂ | methyl | ortho-Ph-phenyl | phenyl |
| 126 | —NO₂ | methyl | meta-Ph-phenyl | phenyl |
| 127 | —NO₂ | methyl | para-Ph-phenyl | phenyl |
| 128 | —NO₂ | methyl | ortho-bromo phenyl | phenyl |
| 129 | —NO₂ | methyl | meta-bromo phenyl | phenyl |
| 130 | —NO₂ | methyl | para-bromo phenyl | phenyl |
| 131 | —NO₂ | methyl | naphthyl | phenyl |
| 132 | —NO₂ | methyl | 3,4-diethylphenyl | phenyl |
| 133 | —NO₂ | methyl | ortho-Ph-phenyl | pyridyl |
| 134 | —NO₂ | methyl | meta-Ph-phenyl | pyridyl |
| 135 | —NO₂ | methyl | para-Ph-phenyl | pyridyl |
| 136 | —NO₂ | methyl | ortho-bromo phenyl | pyridyl |
| 137 | —NO₂ | methyl | meta-bromo phenyl | pyridyl |
| 138 | —NO₂ | methyl | para-bromo phenyl | pyridyl |
| 139 | —NO₂ | methyl | naphthyl | pyridyl |
| 140 | —NO₂ | methyl | 3,4-diethylphenyl | pyridyl |
| 141 | —NO₂ | methyl | ortho-Ph-phenyl | pyrimidinyl |

TABLE 1-continued

| Compound No. | R¹ | R² | R³ | R⁴ |
|---|---|---|---|---|
| 142 | —NO$_2$ | methyl | meta-phenyl-phenyl | pyrimidinyl |
| 143 | —NO$_2$ | methyl | para-phenyl-phenyl | pyrimidinyl |
| 144 | —NO$_2$ | methyl | ortho-bromo phenyl | pyrimidinyl |
| 145 | —NO$_2$ | methyl | meta-bromo phenyl | pyrimidinyl |
| 146 | —NO$_2$ | methyl | para-bromo phenyl | pyrimidinyl |
| 147 | —NO$_2$ | methyl | naphthyl | pyrimidinyl |
| 148 | —NO$_2$ | methyl | 3,4-diethylphenyl | pyrimidinyl |
| 149 | —NO$_2$ | methyl | ortho-phenyl-phenyl | imidazolyl |
| 150 | —NO$_2$ | methyl | meta-phenyl-phenyl | imidazolyl |
| 151 | —NO$_2$ | methyl | para-phenyl-phenyl | imidazolyl |
| 152 | —NO$_2$ | methyl | ortho-bromo phenyl | imidazolyl |
| 153 | —NO$_2$ | methyl | meta-bromo phenyl | imidazolyl |
| 154 | —NO$_2$ | methyl | para-bromo phenyl | imidazolyl |
| 155 | —NO$_2$ | methyl | naphthyl | imidazolyl |
| 156 | —NO$_2$ | methyl | 3,4-diethylphenyl | imidazolyl |
| 157 | —NO$_2$ | methyl | ortho-phenyl-phenyl | thienyl |

TABLE 1-continued

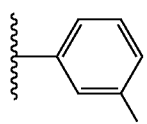

| Compound No. | R¹ | R² | R³ | R⁴ |
|---|---|---|---|---|
| 158 | —NO₂ | methyl | meta-phenyl-phenyl | thienyl |
| 159 | —NO₂ | methyl | para-phenyl-phenyl | thienyl |
| 160 | —NO₂ | methyl | ortho-bromo phenyl | thienyl |
| 161 | —NO₂ | methyl | meta-bromo phenyl | thienyl |
| 162 | —NO₂ | methyl | para-bromo phenyl | thienyl |
| 163 | —NO₂ | methyl | naphthyl | thienyl |
| 164 | —NO₂ | methyl | 3,4-diethylphenyl | thienyl |

TABLE 2

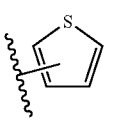

| Compound No. | R¹ | R² | R³ | R⁴ |
|---|---|---|---|---|
| 1 | Cl | H | optionally substituted aryl | aryl or heteroaryl |
| 2 | —NO₂ | H | optionally substituted aryl | aryl or heteroaryl |
| 3 | Cl | alkyl | optionally substituted aryl | aryl or heteroaryl |
| 4 | —NO₂ | alkyl | optionally substituted aryl | aryl or heteroaryl |
| 5 | Cl | H | ortho-phenyl-phenyl | phenyl |
| 6 | Cl | H | meta-phenyl-phenyl | phenyl |
| 7 | Cl | H | para-phenyl-phenyl | phenyl |
| 8 | Cl | H | ortho-bromo phenyl | phenyl |
| 9 | Cl | H | meta-bromo phenyl | phenyl |
| 10 | Cl | H | para-bromo phenyl | phenyl |
| 11 | Cl | H | naphthyl | phenyl |
| 12 | Cl | H | 3,4-diethylphenyl | phenyl |
| 13 | Cl | H | ortho-phenyl-phenyl | pyridyl |
| 14 | Cl | H | meta-phenyl-phenyl | pyridyl |
| 15 | Cl | H | para-phenyl-phenyl | pyridyl |

TABLE 2-continued

[Structure: benzodiazepinone core with R¹, R², R³, R⁴ substituents and para-acetamido phenyl group]

| Compound No. | R¹ | R² | R³ | R⁴ |
|---|---|---|---|---|
| 16 | Cl | H | ortho-bromo phenyl | pyridyl |
| 17 | Cl | H | meta-bromo phenyl | pyridyl |
| 18 | Cl | H | para-bromo phenyl | pyridyl |
| 19 | Cl | H | naphthyl | pyridyl |
| 20 | Cl | H | 3,4-diethylphenyl | pyridyl |
| 21 | Cl | H | ortho-Ph-phenyl | pyrimidinyl |
| 22 | Cl | H | meta-Ph-phenyl | pyrimidinyl |
| 23 | Cl | H | para-Ph-phenyl | pyrimidinyl |
| 24 | Cl | H | ortho-bromo phenyl | pyrimidinyl |
| 25 | Cl | H | meta-bromo phenyl | pyrimidinyl |
| 26 | Cl | H | para-bromo phenyl | pyrimidinyl |
| 27 | Cl | H | naphthyl | pyrimidinyl |
| 28 | Cl | H | 3,4-diethylphenyl | pyrimidinyl |
| 29 | Cl | H | ortho-Ph-phenyl | imidazolyl |
| 30 | Cl | H | meta-Ph-phenyl | imidazolyl |
| 31 | Cl | H | para-Ph-phenyl | imidazolyl |
| 32 | Cl | H | ortho-bromo phenyl | imidazolyl |

TABLE 2-continued

[Structure: benzodiazepinone core with R¹ on fused benzene, R² on N, R³ on alpha carbon, and a para-phenyl substituent bearing -NH-C(=O)-CH₂-R⁴]

| Compound No. | R¹ | R² | R³ | R⁴ |
|---|---|---|---|---|
| 33 | Cl | H | meta-bromo phenyl | 1H-imidazolyl |
| 34 | Cl | H | para-bromo phenyl | 1H-imidazolyl |
| 35 | Cl | H | naphthyl | 1H-imidazolyl |
| 36 | Cl | H | 3,4-diethylphenyl | 1H-imidazolyl |
| 37 | Cl | H | ortho-Ph-phenyl | thienyl |
| 38 | Cl | H | meta-Ph-phenyl | thienyl |
| 39 | Cl | H | para-Ph-phenyl | thienyl |
| 40 | Cl | H | ortho-bromo phenyl | thienyl |
| 41 | Cl | H | meta-bromo phenyl | thienyl |
| 42 | Cl | H | para-bromo phenyl | thienyl |
| 43 | Cl | H | naphthyl | thienyl |
| 44 | Cl | H | 3,4-diethylphenyl | thienyl |
| 45 | —NO₂ | H | ortho-Ph-phenyl | phenyl |
| 46 | —NO₂ | H | meta-Ph-phenyl | phenyl |
| 47 | —NO₂ | H | para-Ph-phenyl | phenyl |
| 48 | —NO₂ | H | ortho-bromo phenyl | phenyl |
| 49 | —NO₂ | H | meta-bromo phenyl | phenyl |
| 50 | —NO₂ | H | para-bromo phenyl | phenyl |
| 51 | —NO₂ | H | naphthyl | phenyl |
| 52 | —NO₂ | H | 3,4-diethylphenyl | phenyl |
| 53 | —NO₂ | H | ortho-Ph-phenyl | pyridyl |

TABLE 2-continued

| Compound No. | R¹ | R² | R³ | R⁴ |
|---|---|---|---|---|
| 54 | —NO₂ | H | meta-phenyl-phenyl | pyridine |
| 55 | —NO₂ | H | para-phenyl-phenyl | pyridine |
| 56 | —NO₂ | H | ortho-bromo phenyl | pyridine |
| 57 | —NO₂ | H | meta-bromo phenyl | pyridine |
| 58 | —NO₂ | H | para-bromo phenyl | pyridine |
| 59 | —NO₂ | H | naphthyl | pyridine |
| 60 | —NO₂ | H | 3,4-diethylpheriyl | pyridine |
| 61 | —NO₂ | H | ortho-phenyl-phenyl | pyrimidine |
| 62 | —NO₂ | H | meta-phenyl-phenyl | pyrimidine |
| 63 | —NO₂ | H | para-phenyl-phenyl | pyrimidine |
| 64 | —NO₂ | H | ortho-bromo phenyl | pyrimidine |
| 65 | —NO₂ | H | meta-bromo phenyl | pyrimidine |
| 66 | —NO₂ | H | para-bromo phenyl | pyrimidine |
| 67 | —NO₂ | H | naphthyl | pyrimidine |
| 68 | —NO₂ | H | 3,4-diethylphenyl | pyrimidine |
| 69 | —NO₂ | H | ortho-phenyl-phenyl | imidazole |
| 70 | —NO₂ | H | meta-phenyl-phenyl | imidazole |
| 71 | —NO₂ | H | para-phenyl-phenyl | imidazole |

TABLE 2-continued

| Compound No. | R¹ | R² | R³ | R⁴ |
|---|---|---|---|---|
| 72 | —NO₂ | H | ortho-bromo phenyl | imidazolyl |
| 73 | —NO₂ | H | meta-bromo phenyl | imidazolyl |
| 74 | —NO₂ | H | para-bromo phenyl | imidazolyl |
| 75 | —NO₂ | H | naphthyl | imidazolyl |
| 76 | —NO₂ | H | 3,4-diethylphenyl | imidazolyl |
| 77 | —NO₂ | H | 2-biphenyl | thienyl |
| 78 | —NO₂ | H | 3-biphenyl | thienyl |
| 79 | —NO₂ | H | 4-biphenyl | thienyl |
| 80 | —NO₂ | H | ortho-bromo phenyl | thienyl |
| 81 | —NO₂ | H | meta-bromo phenyl | thienyl |
| 82 | —NO₂ | H | para-bromo phenyl | thienyl |
| 83 | —NO₂ | H | naphthyl | thienyl |
| 84 | —NO₂ | H | 3,4-diethylphenyl | thienyl |
| 85 | Cl | methyl | 2-biphenyl | phenyl |
| 86 | Cl | methyl | 3-biphenyl | phenyl |
| 87 | Cl | methyl | 4-biphenyl | phenyl |
| 88 | Cl | methyl | ortho-bromo phenyl | phenyl |
| 89 | Cl | methyl | meta-bromo phenyl | phenyl |
| 90 | Cl | methyl | para-bromo phenyl | phenyl |

TABLE 2-continued

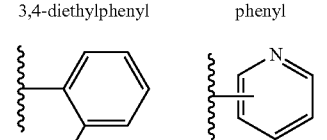

| Compound No. | R¹ | R² | R³ | R⁴ |
|---|---|---|---|---|
| 91 | Cl | methyl | naphthyl | phenyl |
| 92 | Cl | methyl | 3,4-diethylphenyl | phenyl |
| 93 | Cl | methyl | 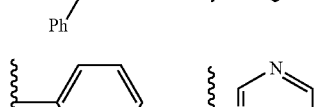 | 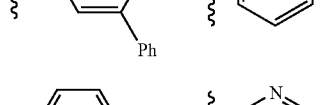 |
| 94 | Cl | methyl | 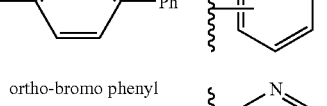 | 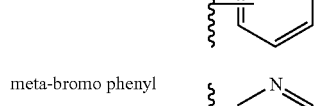 |
| 95 | Cl | methyl | 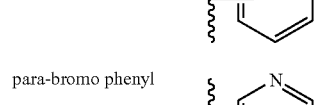 | 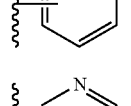 |
| 96 | Cl | methyl | ortho-bromo phenyl | 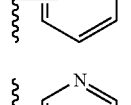 |
| 97 | Cl | methyl | meta-bromo phenyl | 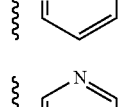 |
| 98 | Cl | methyl | para-bromo phenyl | 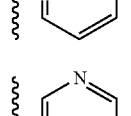 |
| 99 | Cl | methyl | naphthyl | 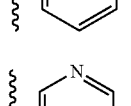 |
| 100 | Cl | methyl | 3,4-diethylphenyl | 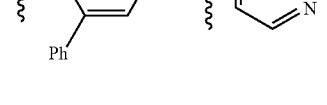 |
| 101 | Cl | methyl |  | 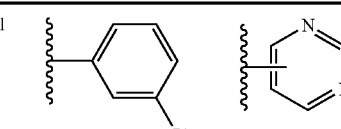 |

TABLE 2-continued

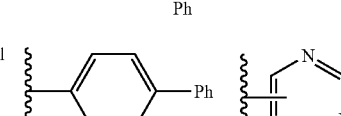

| Compound No. | R¹ | R² | R³ | R⁴ |
|---|---|---|---|---|
| 102 | Cl | methyl | 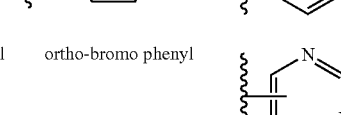 | 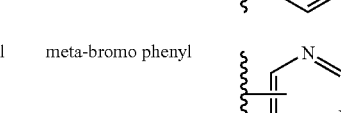 |
| 103 | Cl | methyl | 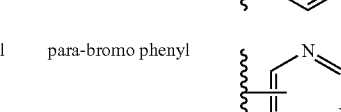 | 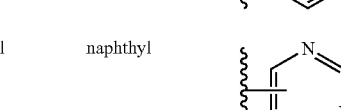 |
| 104 | Cl | methyl | ortho-bromo phenyl | 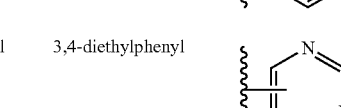 |
| 105 | Cl | methyl | meta-bromo phenyl | 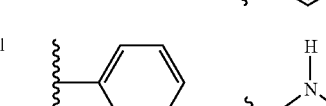 |
| 106 | Cl | methyl | para-bromo phenyl | 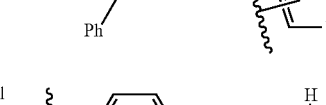 |
| 107 | Cl | methyl | naphthyl | 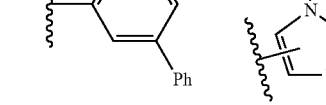 |
| 108 | Cl | methyl | 3,4-diethylphenyl |  |
| 109 | Cl | methyl |  |  |
| 110 | Cl | methyl |  |  |

TABLE 2-continued

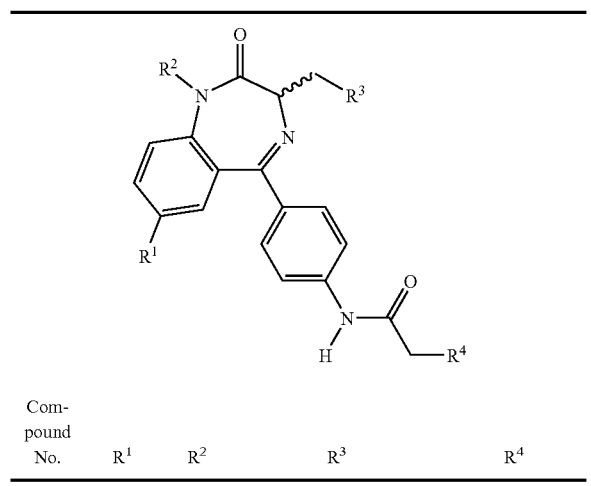

| Compound No. | R¹ | R² | R³ | R⁴ |
|---|---|---|---|---|
| 111 | Cl | methyl | | |
| 112 | Cl | methyl | ortho-bromo phenyl | |
| 113 | Cl | methyl | meta-bromo phenyl | |
| 114 | Cl | methyl | para-bromo phenyl | |
| 115 | Cl | methyl | naphthyl | |
| 116 | Cl | methyl | 3,4-diethylphenyl | |
| 117 | Cl | methyl | | |

TABLE 2-continued

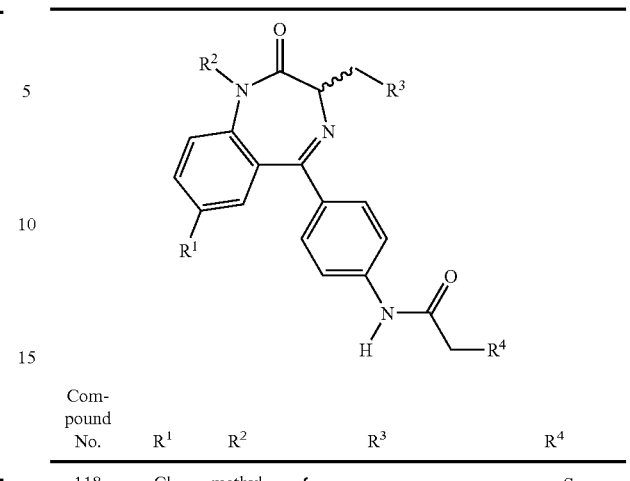

| Compound No. | R¹ | R² | R³ | R⁴ |
|---|---|---|---|---|
| 118 | Cl | methyl | | |
| 119 | Cl | methyl | | |
| 120 | Cl | methyl | ortho-bromo phenyl | |
| 121 | Cl | methyl | meta-bromo phenyl | |
| 122 | Cl | methyl | para-bromo phenyl | |
| 123 | Cl | methyl | naphthyl | |
| 124 | Cl | methyl | 3,4-diethylphenyl | |
| 125 | —NO₂ | methyl | | phenyl |
| 126 | —NO₂ | methyl | | phenyl |

TABLE 2-continued

[Structure: benzodiazepinone with R¹ on fused benzene, R² on ring N, R³ on CH, and a 4-(NHC(O)CH₂R⁴)phenyl group at the imine carbon]

| Compound No. | R¹ | R² | R³ | R⁴ |
|---|---|---|---|---|
| 127 | —NO₂ | methyl | para-Ph-phenyl | phenyl |
| 128 | —NO₂ | methyl | ortho-bromo phenyl | phenyl |
| 129 | —NO₂ | methyl | meta-bromo phenyl | phenyl |
| 130 | —NO₂ | methyl | para-bromo phenyl | phenyl |
| 131 | —NO₂ | methyl | naphthyl | phenyl |
| 132 | —NO₂ | methyl | 3,4-diethylphenyl | phenyl |
| 133 | —NO₂ | methyl | ortho-Ph-phenyl | pyridyl |
| 134 | —NO₂ | methyl | meta-Ph-phenyl | pyridyl |
| 135 | —NO₂ | methyl | para-Ph-phenyl | pyridyl |
| 136 | —NO₂ | methyl | ortho-bromo phenyl | pyridyl |
| 137 | —NO₂ | methyl | meta-bromo phenyl | pyridyl |
| 138 | —NO₂ | methyl | para-bromo phenyl | pyridyl |
| 139 | —NO₂ | methyl | naphthyl | pyridyl |
| 140 | —NO₂ | methyl | 3,4-diethylphenyl | pyrimidinyl |
| 141 | —NO₂ | methyl | ortho-Ph-phenyl | pyrimidinyl |
| 142 | —NO₂ | methyl | meta-Ph-phenyl | pyrimidinyl |
| 143 | —NO₂ | methyl | para-Ph-phenyl | pyrimidinyl |
| 144 | —NO₂ | methyl | ortho-bromo phenyl | pyrimidinyl |
| 145 | —NO₂ | methyl | meta-bromo phenyl | pyrimidinyl |
| 146 | —NO₂ | methyl | para-bromo phenyl | pyrimidinyl |
| 147 | —NO₂ | methyl | naphthyl | pyrimidinyl |
| 148 | —NO₂ | methyl | 3,4-diethylphenyl | pyrimidinyl |

TABLE 2-continued

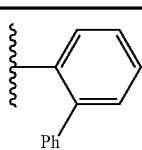

| Compound No. | R¹ | R² | R³ | R⁴ |
|---|---|---|---|---|
| 149 | —NO₂ | methyl | 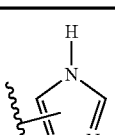 ortho-Ph phenyl | 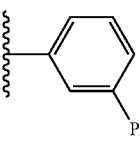 imidazole |
| 150 | —NO₂ | methyl | 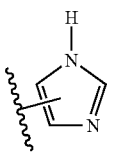 meta-Ph phenyl | 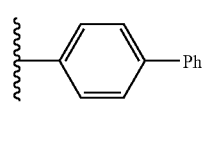 imidazole |
| 151 | —NO₂ | methyl | 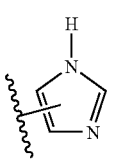 para-Ph phenyl | 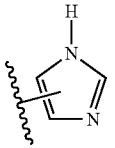 imidazole |
| 152 | —NO₂ | methyl | ortho-bromo phenyl | 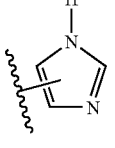 imidazole |
| 153 | —NO₂ | methyl | meta-bromo phenyl | 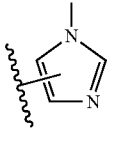 imidazole |
| 154 | —NO₂ | methyl | para-bromo phenyl | 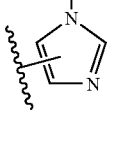 imidazole |
| 155 | —NO₂ | methyl | naphthyl | 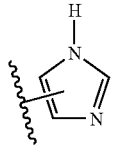 imidazole |

TABLE 2-continued

| Compound No. | R¹ | R² | R³ | R⁴ |
|---|---|---|---|---|
| 156 | —NO₂ | methyl | 3,4-diethylphenyl | 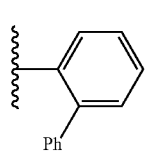 imidazole |
| 157 | —NO₂ | methyl | 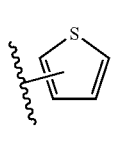 ortho-Ph phenyl | 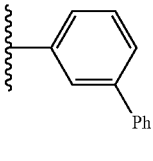 thienyl |
| 158 | —NO₂ | methyl | 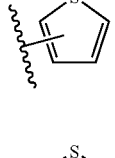 meta-Ph phenyl | 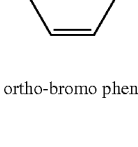 thienyl |
| 159 | —NO₂ | methyl | 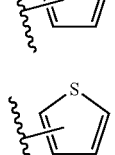 para-Ph phenyl | 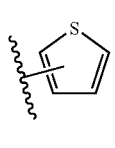 thienyl |
| 160 | —NO₂ | methyl | ortho-bromo phenyl | thienyl |
| 161 | —NO₂ | methyl | meta-bromo phenyl | thienyl |
| 162 | —NO₂ | methyl | para-bromo phenyl | thienyl |
| 163 | —NO₂ | methyl | naphthyl | 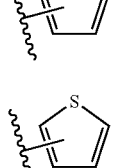 thienyl |
| 164 | —NO₂ | methyl | 3,4-diethylphenyl | 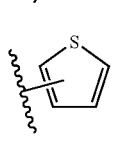 thienyl |

TABLE 3

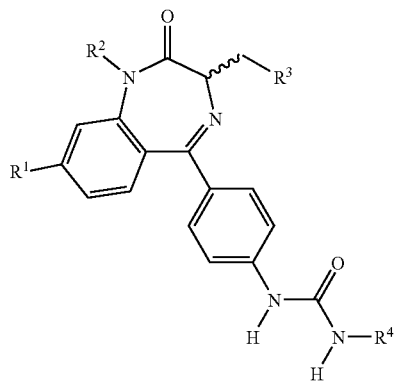

| Compound No. | R¹ | R² | R³ | R⁴ |
|---|---|---|---|---|
| 1 | Cl | H | optionally substituted aryl | aryl or heteroaryl |
| 2 | —NO₂ | H | optionally substituted aryl | aryl or heteroaryl |
| 3 | Cl | alkyl | optionally substituted aryl | aryl or heteroaryl |
| 4 | —NO₂ | alkyl | optionally substituted aryl | aryl or heteroaryl |
| 5 | Cl | H | ortho-phenyl phenyl | phenyl |
| 6 | Cl | H | meta-phenyl phenyl | phenyl |
| 7 | Cl | H | para-phenyl phenyl | phenyl |
| 8 | Cl | H | ortho-bromo phenyl | phenyl |
| 9 | Cl | H | meta-bromo phenyl | phenyl |
| 10 | Cl | H | para-bromo phenyl | phenyl |
| 11 | Cl | H | naphthyl | phenyl |
| 12 | Cl | H | 3,4-diethylphenyl | phenyl |
| 13 | Cl | H | ortho-phenyl phenyl | pyrimidinyl |
| 14 | Cl | H | meta-phenyl phenyl | pyrimidinyl |
| 15 | Cl | H | para-phenyl phenyl | pyrimidinyl |

TABLE 3-continued

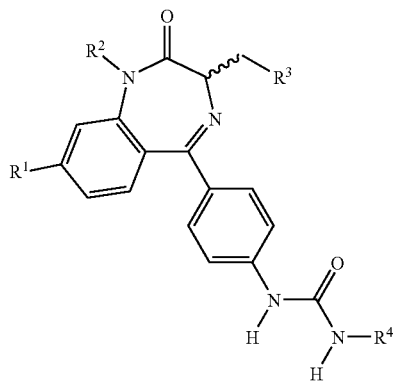

| Compound No. | R¹ | R² | R³ | R⁴ |
|---|---|---|---|---|
| 16 | Cl | H | ortho-bromo phenyl | pyrimidinyl |
| 17 | Cl | H | meta-bromo phenyl | pyrimidinyl |
| 18 | Cl | H | para-bromo phenyl | pyrimidinyl |
| 19 | Cl | H | naphthyl | pyrimidinyl |
| 20 | Cl | H | 3,4-diethylphenyl | pyrimidinyl |
| 21 | Cl | H | ortho-phenyl phenyl | imidazolyl |
| 22 | Cl | H | meta-phenyl phenyl | imidazolyl |
| 23 | Cl | H | para-phenyl phenyl | imidazolyl |

TABLE 3-continued

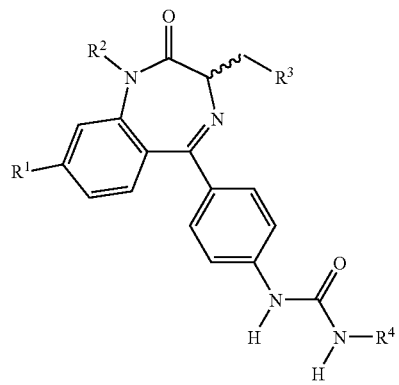

| Compound No. | R¹ | R² | R³ | R⁴ |
|---|---|---|---|---|
| 24 | Cl | H | ortho-bromo phenyl | imidazolyl (NH) |
| 25 | Cl | H | meta-bromo phenyl | imidazolyl (NH) |
| 26 | Cl | H | para-bromo phenyl | imidazolyl (NH) |
| 27 | Cl | H | naphthyl | imidazolyl (NH) |
| 28 | Cl | H | 3,4-diethylphenyl | imidazolyl (NH) |
| 29 | —NO₂ | H | ortho-Ph phenyl | phenyl |
| 30 | —NO₂ | H | meta-Ph phenyl | phenyl |

TABLE 3-continued

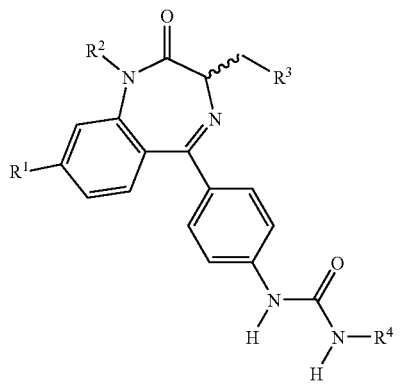

| Compound No. | R¹ | R² | R³ | R⁴ |
|---|---|---|---|---|
| 31 | —NO₂ | H | para-Ph phenyl | phenyl |
| 32 | —NO₂ | H | ortho-bromo phenyl | phenyl |
| 33 | —NO₂ | H | meta-bromo phenyl | phenyl |
| 34 | —NO₂ | H | para-bromo phenyl | phenyl |
| 35 | —NO₂ | H | naphthyl | phenyl |
| 36 | —NO₂ | H | 3,4-diethylphenyl | phenyl |
| 37 | —NO₂ | H | ortho-Ph phenyl | pyrimidinyl |
| 38 | —NO₂ | H | meta-Ph phenyl | pyrimidinyl |
| 39 | —NO₂ | H | para-Ph phenyl | pyrimidinyl |
| 40 | —NO₂ | H | ortho-bromo phenyl | pyrimidinyl |
| 41 | —NO₂ | H | meta-bromo phenyl | pyrimidinyl |
| 42 | —NO₂ | H | para-bromo phenyl | pyrimidinyl |
| 43 | —NO₂ | H | naphthyl | pyrimidinyl |

TABLE 3-continued

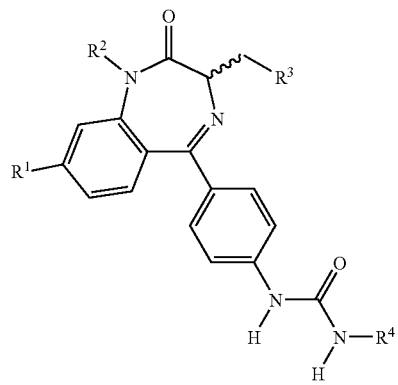

| Compound No. | R¹ | R² | R³ | R⁴ |
|---|---|---|---|---|
| 44 | —NO₂ | H | 3,4-diethylphenyl | 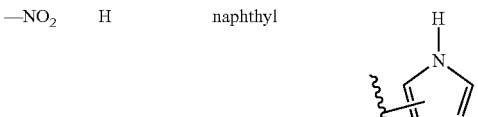 |
| 45 | —NO₂ | H | 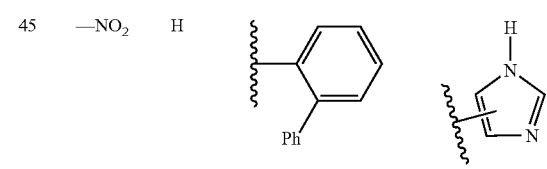 | 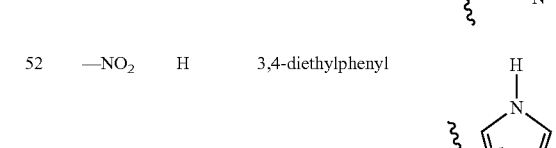 |
| 46 | —NO₂ | H | 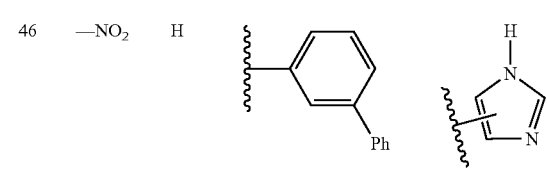 | 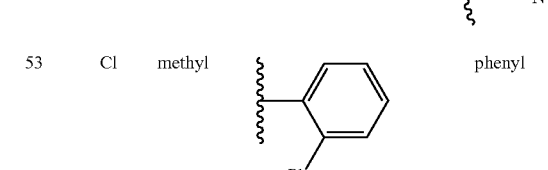 |
| 47 | —NO₂ | H | 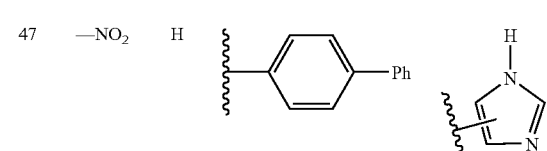 | 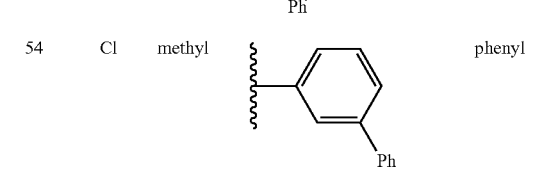 |
| 48 | —NO₂ | H | ortho-bromo phenyl | 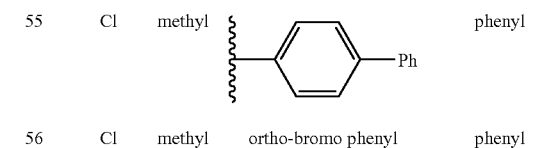 |
| 49 | —NO₂ | H | meta-bromo phenyl | 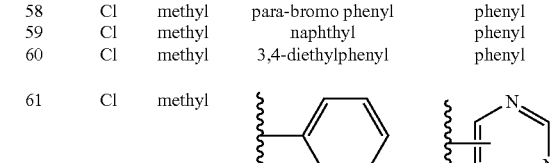 |
| 50 | —NO₂ | H | para-bromo phenyl | 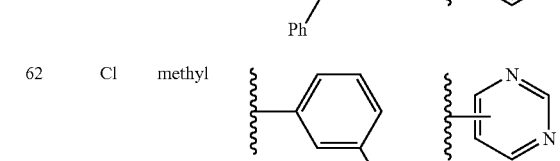 |

TABLE 3-continued

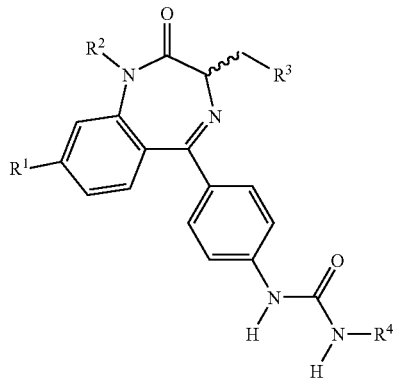

| Compound No. | R¹ | R² | R³ | R⁴ |
|---|---|---|---|---|
| 51 | —NO₂ | H | naphthyl | 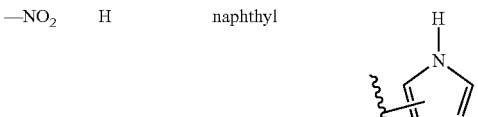 |
| 52 | —NO₂ | H | 3,4-diethylphenyl | 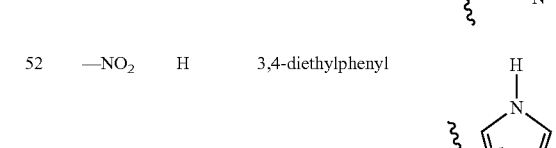 |
| 53 | Cl | methyl | 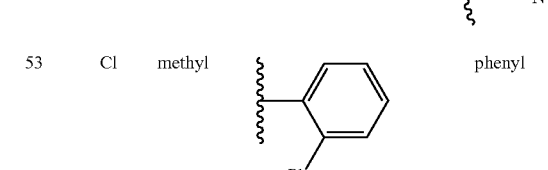 | phenyl |
| 54 | Cl | methyl | 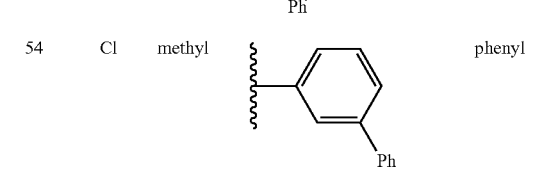 | phenyl |
| 55 | Cl | methyl | 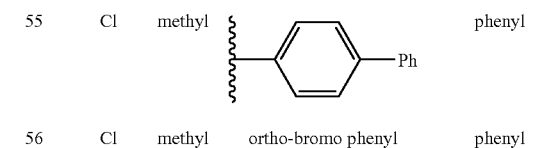 | phenyl |
| 56 | Cl | methyl | ortho-bromo phenyl | phenyl |
| 57 | Cl | methyl | meta-bromo phenyl | phenyl |
| 58 | Cl | methyl | para-bromo phenyl | phenyl |
| 59 | Cl | methyl | naphthyl | phenyl |
| 60 | Cl | methyl | 3,4-diethylphenyl | phenyl |
| 61 | Cl | methyl | 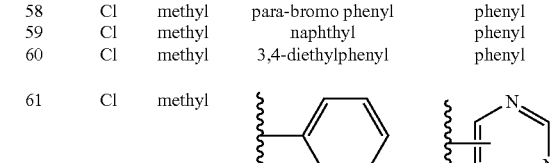 |  |
| 62 | Cl | methyl | 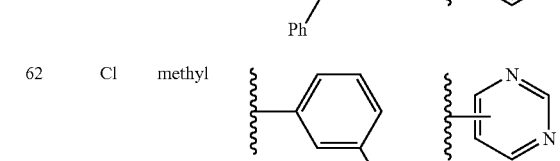 |  |

TABLE 3-continued

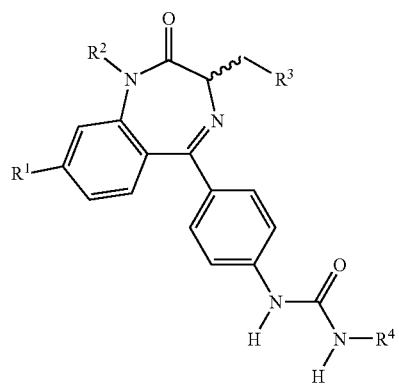

| Compound No. | R¹ | R² | R³ | R⁴ |
|---|---|---|---|---|
| 63 | Cl | methyl | 4-phenylphenyl | pyrimidinyl |
| 64 | Cl | methyl | ortho-bromo phenyl | pyrimidinyl |
| 65 | Cl | methyl | meta-bromo phenyl | pyrimidinyl |
| 66 | Cl | methyl | para-bromo phenyl | pyrimidinyl |
| 67 | Cl | methyl | naphthyl | pyrimidinyl |
| 68 | Cl | methyl | 3,4-diethylphenyl | pyrimidinyl |
| 69 | Cl | methyl | 2-phenylphenyl | imidazolyl |
| 70 | Cl | methyl | 3-phenylphenyl | imidazolyl |
| 71 | Cl | methyl | 4-phenylphenyl | imidazolyl |
| 72 | Cl | methyl | ortho-bromo phenyl | imidazolyl |
| 73 | Cl | methyl | meta-bromo phenyl | imidazolyl |
| 74 | Cl | methyl | para-bromo phenyl | imidazolyl |
| 75 | Cl | methyl | naphthyl | imidazolyl |
| 76 | Cl | methyl | 3,4-diethylphenyl | imidazolyl |
| 77 | —NO₂ | methyl | 2-phenylphenyl | phenyl |

TABLE 3-continued

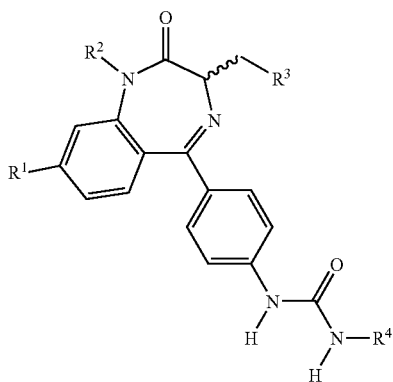

| Compound No. | R¹ | R² | R³ | R⁴ |
|---|---|---|---|---|
| 78 | —NO$_2$ | methyl | meta-phenyl-phenyl | phenyl |
| 79 | —NO$_2$ | methyl | para-phenyl-phenyl | phenyl |
| 80 | —NO$_2$ | methyl | ortho-bromo phenyl | phenyl |
| 81 | —NO$_2$ | methyl | meta-bromo phenyl | phenyl |
| 82 | —NO$_2$ | methyl | para-bromo phenyl | phenyl |
| 83 | —NO$_2$ | methyl | naphthyl | phenyl |
| 84 | —NO$_2$ | methyl | 3,4-diethylphenyl | phenyl |
| 85 | —NO$_2$ | methyl | ortho-phenyl-phenyl | pyrimidinyl |
| 86 | —NO$_2$ | methyl | meta-phenyl-phenyl | pyrimidinyl |
| 87 | —NO$_2$ | methyl | para-phenyl-phenyl | pyrimidinyl |
| 88 | —NO$_2$ | methyl | ortho-bromo phenyl | pyrimidinyl |
| 89 | —NO$_2$ | methyl | meta-bromo phenyl | pyrimidinyl |
| 90 | —NO$_2$ | methyl | para-bromo phenyl | pyrimidinyl |
| 91 | —NO$_2$ | methyl | naphthyl | pyrimidinyl |
| 92 | —NO$_2$ | methyl | 3,4-diethylphenyl | pyrimidinyl |
| 93 | —NO$_2$ | methyl | meta-phenyl-phenyl | imidazolyl |
| 94 | —NO$_2$ | methyl | para-phenyl-phenyl | imidazolyl |
| 95 | —NO$_2$ | methyl | pyrimidinyl | imidazolyl |
| 96 | —NO$_2$ | methyl | ortho-bromo phenyl | imidazolyl |
| 97 | —NO$_2$ | methyl | meta-bromo phenyl | imidazolyl |

TABLE 3-continued

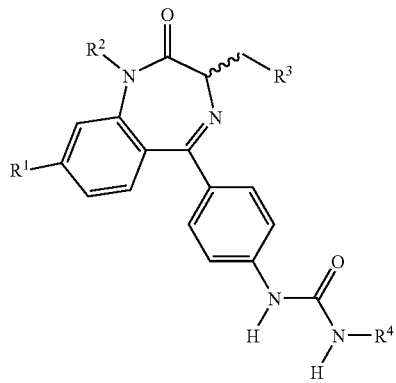

| Compound No. | R¹ | R² | R³ | R⁴ |
|---|---|---|---|---|
| 98 | —NO₂ | methyl | para-bromo phenyl | imidazolyl |
| 99 | —NO₂ | methyl | naphthyl | imidazolyl |
| 100 | —NO₂ | methyl | 3,4-diethylphenyl | imidazolyl |

TABLE 4

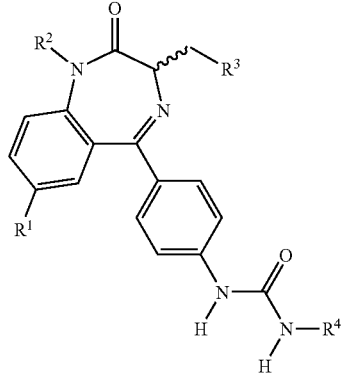

| Compound No. | R¹ | R² | R³ | R⁴ |
|---|---|---|---|---|
| 1 | Cl | H | optionally substituted aryl | aryl or heteroaryl |
| 2 | —NO₂ | H | optionally substituted aryl | aryl or heteroaryl |
| 3 | Cl | alkyl | optionally substituted aryl | aryl or heteroaryl |
| 4 | —NO₂ | alkyl | optionally substituted aryl | aryl or heteroaryl |
| 5 | Cl | H | ortho-Ph phenyl | phenyl |
| 6 | Cl | H | meta-Ph phenyl | phenyl |
| 7 | Cl | H | para-Ph phenyl | phenyl |
| 8 | Cl | H | ortho-bromo phenyl | phenyl |
| 9 | Cl | H | meta-bromo phenyl | phenyl |
| 10 | Cl | H | para-bromo phenyl | phenyl |
| 11 | Cl | H | naphthyl | phenyl |
| 12 | Cl | H | 3,4-diethylphenyl | phenyl |
| 13 | Cl | H | ortho-Ph phenyl | pyrimidinyl |
| 14 | Cl | H | meta-Ph phenyl | pyrimidinyl |
| 15 | Cl | H | para-Ph phenyl | pyrimidinyl |
| 16 | Cl | H | ortho-bromo phenyl | pyrimidinyl |

TABLE 4-continued

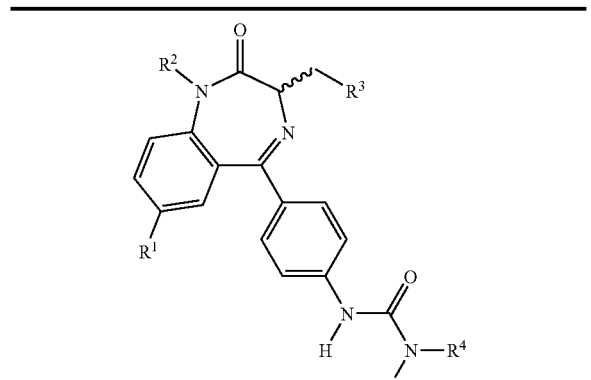

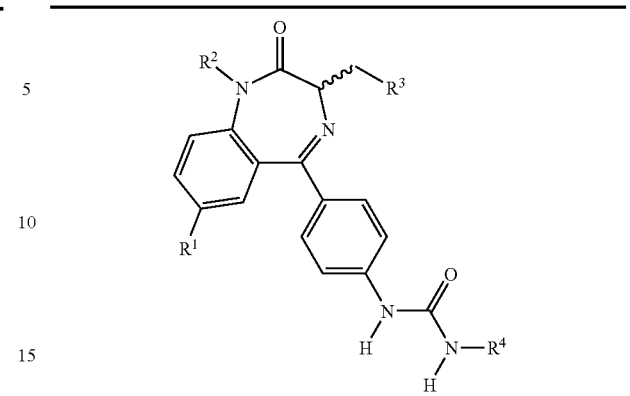

| Compound No. | R¹ | R² | R³ | R⁴ |
|---|---|---|---|---|
| 17 | Cl | H | meta-bromo phenyl | pyrimidinyl |
| 18 | Cl | H | para-bromo phenyl | pyrimidinyl |
| 19 | Cl | H | naphthyl | pyrimidinyl |
| 20 | Cl | H | 3,4-diethylphenyl | pyrimidinyl |
| 21 | Cl | H | 2-Ph-phenyl | imidazolyl |
| 22 | Cl | H | 3-Ph-phenyl | imidazolyl |
| 23 | Cl | H | 4-Ph-phenyl | imidazolyl |
| 24 | Cl | H | ortho-bromo phenyl | imidazolyl |
| 25 | Cl | H | meta-bromo phenyl | imidazolyl |
| 26 | Cl | H | para-bromo phenyl | imidazolyl |
| 27 | Cl | H | naphthyl | imidazolyl |
| 28 | Cl | H | 3,4-diethylphenyl | imidazolyl |
| 29 | —NO₂ | H | 2-Ph-phenyl | phenyl |
| 30 | —NO₂ | H | 3-Ph-phenyl | phenyl |
| 31 | —NO₂ | H | 4-Ph-phenyl | phenyl |
| 32 | —NO₂ | H | ortho-bromo phenyl | phenyl |
| 33 | —NO₂ | H | meta-bromo phenyl | phenyl |
| 34 | —NO₂ | H | para-bromo phenyl | phenyl |

TABLE 4-continued
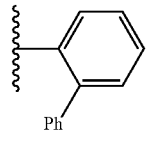
| Compound No. | R¹ | R² | R³ | R⁴ |
|---|---|---|---|---|
| 35 | —NO₂ | H | naphthyl | phenyl |
| 36 | —NO₂ | H | 3,4-diethylphenyl | phenyl |
| 37 | —NO₂ | H | 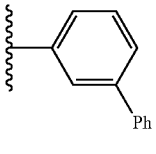 | 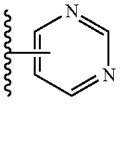 |
| 38 | —NO₂ | H | 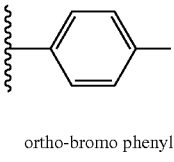 | 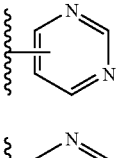 |
| 39 | —NO₂ | H | 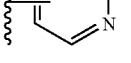 | 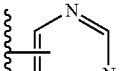 |
| 40 | —NO₂ | H | ortho-bromo phenyl | 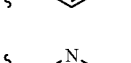 |
| 41 | —NO₂ | H | meta-bromo phenyl | 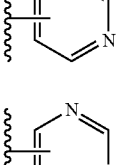 |
| 42 | —NO₂ | H | para-bromo phenyl | 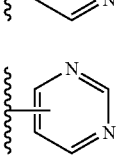 |
| 43 | —NO₂ | H | naphthyl | 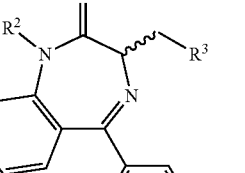 |
| 44 | —NO₂ | H | 3,4-diethylphenyl | 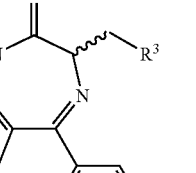 |
TABLE 4-continued
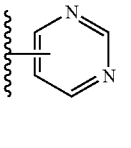
| Compound No. | R¹ | R² | R³ | R⁴ |
|---|---|---|---|---|
| 45 | —NO₂ | H | 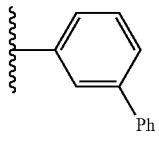 | 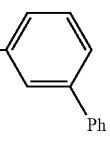 |
| 46 | —NO₂ | H | 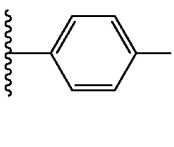 | 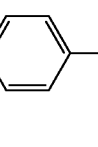 |
| 47 | —NO₂ | H | 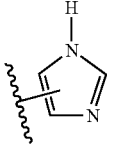 | 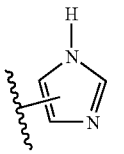 |
| 48 | —NO₂ | H | ortho-bromo phenyl | 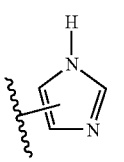 |
| 49 | —NO₂ | H | meta-bromo phenyl | |
| 50 | —NO₂ | H | para-bromo phenyl | |
| 51 | —NO₂ | H | naphthyl | |

TABLE 4-continued

| Compound No. | R¹ | R² | R³ | R⁴ |
|---|---|---|---|---|
| 52 | —NO₂ | H | 3,4-diethylphenyl | 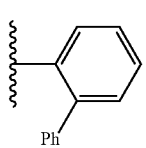 (1H-imidazolyl) |
| 53 | Cl | methyl | 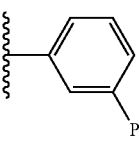 (ortho-Ph-phenyl) | phenyl |
| 54 | Cl | methyl | 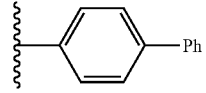 (meta-Ph-phenyl) | phenyl |
| 55 | Cl | methyl | 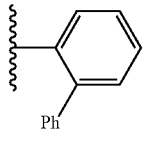 (para-Ph-phenyl) | phenyl |
| 56 | Cl | methyl | ortho-bromo phenyl | phenyl |
| 57 | Cl | methyl | meta-bromo phenyl | phenyl |
| 58 | Cl | methyl | para-bromo phenyl | phenyl |
| 59 | Cl | methyl | naphthyl | phenyl |
| 60 | Cl | methyl | 3,4-diethylphenyl | phenyl |
| 61 | Cl | methyl | 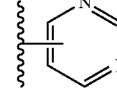 (ortho-Ph-phenyl) | 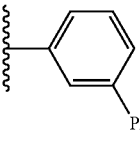 (pyrimidinyl) |
| 62 | Cl | methyl | 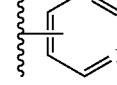 (meta-Ph-phenyl) | 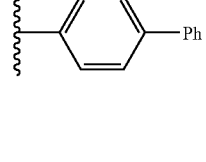 (pyrimidinyl) |
| 63 | Cl | methyl | 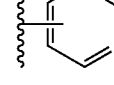 (para-Ph-phenyl) | 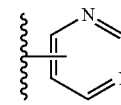 (pyrimidinyl) |
| 64 | Cl | methyl | ortho-bromo phenyl | 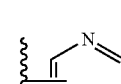 (pyrimidinyl) |
| 65 | Cl | methyl | meta-bromo phenyl | 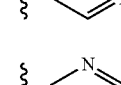 (pyrimidinyl) |
| 66 | Cl | methyl | para-bromo phenyl | 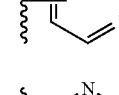 (pyrimidinyl) |
| 67 | Cl | methyl | naphthyl | 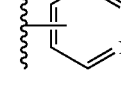 (pyrimidinyl) |
| 68 | Cl | methyl | 3,4-diethylphenyl | 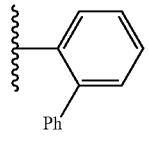 (pyrimidinyl) |
| 69 | Cl | methyl | 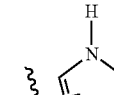 (ortho-Ph-phenyl) | 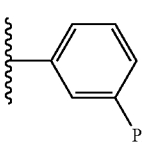 (1H-imidazolyl) |
| 70 | Cl | methyl | 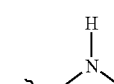 (meta-Ph-phenyl) | 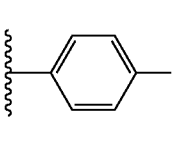 (1H-imidazolyl) |
| 71 | Cl | methyl |  (para-Ph-phenyl) |  (1H-imidazolyl) |

TABLE 4-continued

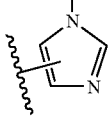

| Compound No. | R¹ | R² | R³ | R⁴ |
|---|---|---|---|---|
| 72 | Cl | methyl | ortho-bromo phenyl | 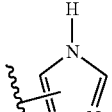 |
| 73 | Cl | methyl | meta-bromo phenyl | 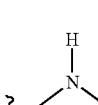 |
| 74 | Cl | methyl | para-bromo phenyl | 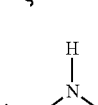 |
| 75 | Cl | methyl | naphthyl | 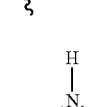 |
| 76 | Cl | methyl | 3,4-diethylphenyl | 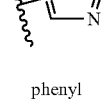 |
| 77 | —NO₂ | methyl | 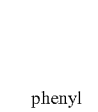 | phenyl |
| 78 | —NO₂ | methyl | 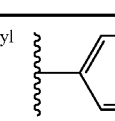 | phenyl |

TABLE 4-continued

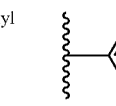

| Compound No. | R¹ | R² | R³ | R⁴ |
|---|---|---|---|---|
| 79 | —NO₂ | methyl | 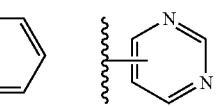 | phenyl |
| 80 | —NO₂ | methyl | ortho-bromo phenyl | phenyl |
| 81 | —NO₂ | methyl | meta-bromo phenyl | phenyl |
| 82 | —NO₂ | methyl | para-bromo phenyl | phenyl |
| 83 | —NO₂ | methyl | naphthyl | phenyl |
| 84 | —NO₂ | methyl | 3,4-diethylphenyl | phenyl |
| 85 | —NO₂ | methyl | 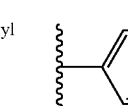 | 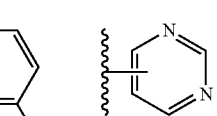 |
| 86 | —NO₂ | methyl | 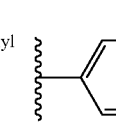 | 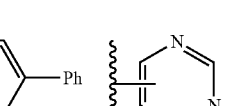 |
| 87 | —NO₂ | methyl | 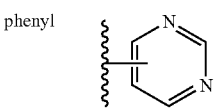 | 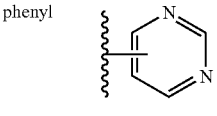 |
| 88 | —NO₂ | methyl | ortho-bromo phenyl | 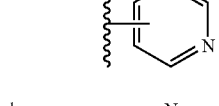 |
| 89 | —NO₂ | methyl | meta-bromo phenyl |  |
| 90 | —NO₂ | methyl | para-bromo phenyl |  |
| 91 | —NO₂ | methyl | naphthyl |  |

TABLE 4-continued

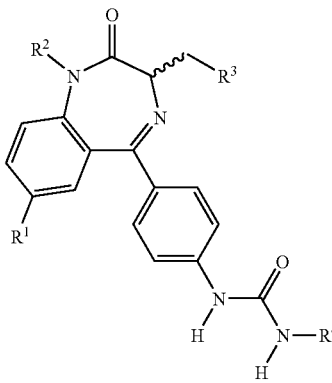

| Compound No. | R¹ | R² | R³ | R⁴ |
|---|---|---|---|---|
| 92 | —NO₂ | methyl | 3,4-diethylphenyl | pyrimidinyl |
| 93 | —NO₂ | methyl | 2-phenylphenyl | imidazolyl |
| 94 | —NO₂ | methyl | 3-phenylphenyl | imidazolyl |
| 95 | —NO₂ | methyl | 4-phenylphenyl | imidazolyl |
| 96 | —NO₂ | methyl | ortho-bromo phenyl | imidazolyl |
| 97 | —NO₂ | methyl | meta-bromo phenyl | imidazolyl |
| 98 | —NO₂ | methyl | para-bromo phenyl | imidazolyl |

TABLE 4-continued

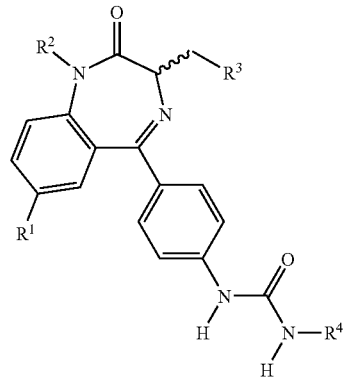

| Compound No. | R¹ | R² | R³ | R⁴ |
|---|---|---|---|---|
| 99 | —NO₂ | methyl | naphthyl | imidazolyl |
| 100 | —NO₂ | methyl | 3,4-diethylphenyl | imidazolyl |

In summary, a large number of compounds are presented herein. It is understood, however, that any one or more of these compounds can be used to treat a variety of dysregulatory disorders related to cellular death as described elsewhere herein. Additionally, any one or more of these compounds can be used to inhibit ATP Hydrolysis while not affecting cell synthesis or cell viability. Additionally, any one or more of these compounds can be used in combination with at least one other therapeutic agent (see, e.g., potassium channel openers, calcium channel blockers, sodium hydrogen exchanger inhibitors, antiarrhythmic agents (e.g., sotalol, dofetilide, amiodarone, azimilide, ibutilide, ditiazem, verapamil), antiatherosclerotic agents, anticoagulants, antithrombotic agents, prothrombolytic agents, fibrinogen antagonists, diuretics, antihypertensive agents (e.g., captopril, lisinopril, zofenopril, ramipril, fosinopril, enalapril, ceranopril, cilazopril, delapril, pentopril, quinapril, omapatrilat, gemopatrilat, losartan, irbesartan, valsartan, sitaxsentan, atrsentan), ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents including, but not limited to, ACE inhibitors, AT-1 receptor antagonists, ET receptor antagonists, dual ET/AII receptor antagonists, and vasopepsidase inhibitors, or an antiplatelet agent (platelet inhibitor) comprising GPIIb/IIIa blockers, P2Y$_1$ and P2Y$_{12}$ antagonists, thromboxane receptor antagonists, abciximab, eptifibatide, tirofiban, clopidogrel, toclopidine, CS-747, ifetroban, and aspirin) (see, e.g., propafenone, propranolol; sotalol, dofetilide, amiodarone, azimilide, ibutilide, ditiazem, verapamil, captopril, lisinopril, zofenopril, ramipril, fosinopril, enalapril, cilazopril, delapril, pentopril, quinapril, omapatrilat, gemopatrilat, losartan, irbesartan, valsartan, sitaxsentan, atrsentan; verapamil, nifedipine, diltiazem, amlodipine and mybefradil, digitalis, ouabain, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, burnetanide, triamtrenene, amiloride, spironolatone, aplirinone, dipyridamole, cilostazol, sildenafil, ifetroban, picotamide, ketanserin, clopidogrel, picotamide, rosuvastaitin, atavastatin visastatin, questran, CP-529414, lovenox, enoxaparain dalteparinnadolol, carvedilol, albuterol, terbutaline, formoterol, salmeterol, bitolterol, pilbuterol, fenoterol, ipratropium bromide, metformin, acarbose, repaglinide, glimpepiride, glyburide, glyburide, glipizide, glucovance, troglitazone, rosiglitazone, pioglitazone, GLP-1, nefazodone, sertraline, diazepam, lorazepam, buspirone, hydroxyzine pamoate, acarbose, endostatin, probucol, BO-653, Vitamin A, Vitamin E, AGI-1067, alendronate, raloxifene, orlistate, cyclosperine A, paclitaxel, FK506, adriamycin, famotidine, rapitidine, ompeprazole, estrogen, estradiol, dipyridamole, cilostazol, sildenafil, ketanserin, taxol, cisplatin, paclitaxel, adriamycin, epothilones, carboplatin, cromolyn, nedocromil, theophylline, zileuton, zafirlukast, monteleukast, pranleukast, beclomethasone, triamcinolone, budesonide, fluticasone, flunisolidem prednisone; dexamethasone, etanercept, aspirin, indomethacin, pravastatin, simvastatin, atorvastatin, fluvastatin, cerivastatin, AZ4522, itavastatin, ZD-4522, rosuvastatin, atavastatin, visastatin, abciximab, eptifibatide, tirofiban, clopidogrel, ticlopidine, CS-747, ifetroban, aspirin; cariporide, streptokinase, reteplase, activase, lanoteplase, urokinase, prourokinse, tenecteplase, lanoteplase, anistreplase, eminase, lepirudin, argatroban, XR-330, T686, anti-α-2-antiplasmin antibody, and doesdipyridanmol), sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents selected from ACE inhibitors, AT-1 receptor antagonists, ET receptor antagonists, dual ET/AII receptor antagonists, and vasopepsidase inhibitors, or an antiplatelet agent selected from GPIIb/IIIa blockers, P2Y$_1$ and P2Y$_{12}$ antagonists, thromboxane receptor antagonists, and aspirin) Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate;

Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabinofluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda). Other anti-cancer agents include, but are not limited to, Antiproliferative agents (e.g., Piritrexim Isothionate), Antiprostatic hypertrophy agent (e.g., Sitogluside), Benign prostatic hyperplasia therapy agents (e.g., Tamsulosin Hydrochloride), Prostate growth inhibitor agents (e.g., Pentomone), and Radioactive agents: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; and Triolein I 131) in along with a pharmaceutically-acceptable carrier or diluent in a pharmaceutical composition.

Additional anti-cancer agents include, but are not limited to anti-cancer Supplementary Potentiating Agents: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. Still other anticancer agents include, but are not limited to, annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodertnolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-C1-2'deoxyadenosine; Fludarabine-$PO_4$; mitoxantrone; mitozolomide; Pentostatin; and Tomudex. One particularly preferred class of anticancer agents are taxanes (e.g., paclitaxel and docetaxel). Another important category of anticancer agent is annonaceous acetogenin. Additionally, any one or more of these compounds can be used to treat a $F_1F_0$ ATP hydrolase associated disorder (e.g., myocardial infarction, ventricular hypertrophy, coronary artery disease, non-Q wave MI, congestive heart failure, cardiac arrhythmias, unstable angina, chronic stable angina, Prinzmetal's angina, high blood pressure, intermittent claudication, peripheral occlusive arterial disease, thrombotic or thromboembolic symptoms of thromboembolic stroke, venous thrombosis, arterial thrombosis, cerebral thrombosis, pulmonary embolism, cerebral embolism, thrombophilia, disseminated intravascular coagulation, restenosis, atrial fibrillation, ventricular enlargement, atherosclerotic vascular disease, atherosclerotic plaque rupture, atherosclerotic plaque formation, transplant atherosclerosis, vascular remodeling atherosclerosis, cancer, surgery, inflammation, systematic infection, artificial surfaces, interventional cardiology, immobility, medication, pregnancy and fetal loss, and diabetic complications comprising retinopathy, nephropathy and neuropathy) in a patient.

III. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present invention are useful in the preparation of medicaments to treat a variety of conditions associated with dysregulation of cell death, aberrant cell growth and hyperproliferation.

In addition, the compounds are also useful for preparing medicaments for treating other disorders wherein the effectiveness of the compounds are known or predicted. Such disorders include, but are not limited to, autoimmune disorders disorders. The methods and techniques for preparing medicaments of a compound of the present invention are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents (e.g., a benzodiazepine compound as described in U.S. Pat. Nos. 7,220,739, 7,144,880 and 7,125,866, U.S. patent application Ser. Nos. 11/796,039, 11/662,103, 11/591,324, 11/586,097, 11/585,492, 11/445,010, 11/324,419, 11/176, 719, 11/110,228, 10/935,333, 10/886,450, 10/795,535, 10/634,114, 10/427, 211, 10/217,878, and 09/767,283, and U.S. Provisional Patent Nos. 60/906,167, 60/906,016, 60/878,519, 60/812,270, 60/802,394, 60/732,045, 60/730, 711, 60/704,102, 60/686,348, 60/641,040, 60/607,599, 60/565,788, and related patent applications. Each carrier should be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In preferred embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents. In preferred embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent. Formulations for rectal administration may be presented as a suppository with suitable base comprising, for example, cocoa butter or a salicylate. Formulations suitable for vaginal administration may be presented as pessaries, creams, gels, pastes, foams or spray formulations containing in addition to the agent, such carriers as are known in the art to be appropriate. Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoleic acid), extenders, and stabilizers, etc.

In some embodiments, the compounds of the present invention are provided in unsolvated form or are in non-aqueous solutions (e.g., ethanol). Compositions and methods for similar benzodiazepine compounds are described in U.S. patent application Ser. No. 11/445,010, herein incorporated by reference in its entirety.

C. Exemplary Administration Routes and Dosing Considerations

Various delivery systems are known and can be used to administer therapeutic agents (e.g., exemplary compounds as described in Section II above) of the present invention, e.g., encapsulation in liposomes, microparticles, microcapsules, receptor-mediated endocytosis, and the like. Methods of delivery include, but are not limited to, intra-arterial, intramuscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified can be administered to subjects or individuals susceptible to or at risk of developing pathological growth of target cells and correlated conditions. When the agent is administered to a subject such as a mouse, a rat or a human patient, the agent can be added to a pharmaceutically acceptable carrier and systemically or topically administered to the subject. To identify patients that can be beneficially treated, a tissue sample is removed from the patient and the cells are assayed for sensitivity to the agent. Therapeutic amounts are empirically determined and vary with the pathology being treated, the subject being treated and the efficacy and toxicity of the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is cancer, the additional agent can be a chemotherapeutic agent or radiation. When the condition being treated is an autoimmune disorder, the additional agent can be an immunosuppressant or an anti-inflammatory agent. When the condition being treated is chronic inflammation, the additional agent can be an anti-inflammatory agent. The additional agents to be co-administered, such as anticancer, immunosuppressant, anti-inflammatory, and can be any of the well-known agents in the art, including, but not limited to, those that are currently in clinical use. The determination of appropriate type and dosage of radiation treatment is also within the skill in the art or can be determined with relative ease.

Treatment of the various conditions associated with abnormal apoptosis is generally limited by the following two major factors: (1) the development of drug resistance and (2) the toxicity of known therapeutic agents. In certain cancers, for example, resistance to chemicals and radiation therapy has been shown to be associated with inhibition of apoptosis. Some therapeutic agents have deleterious side effects, including non-specific lymphotoxicity, renal and bone marrow toxicity.

The methods described herein address both these problems. Drug resistance, where increasing dosages are required to achieve therapeutic benefit, is overcome by co-administering the compounds described herein with the known agent. The compounds described herein sensitize target cells to known agents (and vice versa) and, accordingly, less of these agents are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases were drug resistance has increased the requisite dosage. When the claimed compounds are co-administered with the known agent, they reduce the dosage required which, in turn, reduces the deleterious effects. Further, because the claimed compounds are themselves both effective and non-toxic in large doses, co-administration of proportionally more of these compounds than known toxic therapeutics will achieve the desired effects while minimizing toxic effects.

IV. Drug Screens

In preferred embodiments of the present invention, the compounds of the present invention, and other potentially useful compounds, are screened for their binding affinity to the oligomycin sensitivity conferring protein (OSCP) portion of the ATP synthase complex. In particularly preferred embodiments, compounds are selected for use in the methods of the present invention by measuring their biding affinity to recombinant OSCP protein. A number of suitable screens for measuring the binding affinity of drugs and other small molecules to receptors are known in the art. In some embodiments, binding affinity screens are conducted in in vitro systems. In other embodiments, these screens are conducted in in vivo or ex vivo systems. While in some embodiments quantifying the intracellular level of ATP following administration of the compounds of the present invention provides an indication of the efficacy of the methods, preferred embodiments of the present invention do not require intracellular ATP or pH level quantification.

Additional embodiments are directed to measuring levels (e.g., intracellular) of superoxide in cells and/or tissues to measure the effectiveness of particular contemplated methods and compounds of the present invention. In this regard, those skilled in the art will appreciate and be able to provide a number of assays and methods useful for measuring superoxide levels in cells and/or tissues.

In some embodiments, structure-based virtual screening methodologies are contemplated for predicting the binding affinity of compounds of the present invention with OSCP.

Any suitable assay that allows for a measurement of the rate of binding or the affinity of a benzodiazepine or other compound to the OSCP may be utilized. Examples include, but are not limited to, competition binding using Bz-423, surface plasma resonace (SPR) and radio-immunopreciptiation assays (Lowman et al., J. Biol. Chem. 266:10982 [1991]). Surface Plasmon Resonance techniques involve a surface coated with a thin film of a conductive metal, such as gold, silver, chrome or aluminum, in which electromagnetic waves, called Surface Plasmons, can be induced by a beam of light incident on the metal glass interface at a specific angle called the Surface Plasmon Resonance angle. Modulation of the refractive index of the interfacial region between the solution and the metal surface following binding of the captured macromolecules causes a change in the SPR angle which can either be measured directly or which causes the amount of light reflected from the underside of the metal surface to change. Such changes can be directly related to the mass and other optical properties of the molecules binding to the SPR device surface. Several biosensor systems based on such principles have been disclosed (See e.g., WO 90/05305). There are also several commercially available SPR biosensors (e.g., BiaCore, Uppsala, Sweden).

In some embodiments, compounds are screened in cell culture or in vivo (e.g., non-human or human mammals) for their ability to modulate ATP synthase activity. Any suitable assay may be utilized, including, but not limited to, cell proliferation assays (Commercially available from, e.g., Promega, Madison, Wis. and Stratagene, La Jolla, Calif.) and cell based dimerization assays. (See e.g., Fuh et al., Science, 256:1677 [1992]; Colosi et al., J. Biol. Chem., 268:12617 [1993]). Additional assay formats that find use with the present invention include, but are not limited to, assays for measuring cellular ATP levels, and cellular superoxide levels.

The present invention also provides methods of modifying and derivatizing the compositions of the present invention to increase desirable properties (e.g., binding affinity, activity, and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In other embodiments, rational design methods are used to predict and model in silico ligand-receptor interactions prior to confirming results by routine experimentation.

V. Therapeutic Application

In certain embodiments, the present invention provides methods (e.g., therapeutic applications) for regulating cell death comprising: a) providing: i. target cells having mitochondria; and ii. a composition (e.g., exemplary compounds as described in Section III above); and b) exposing the target cells to the composition under conditions such that the exposure results in cell death. In some embodiments, the composition binds to the mitochondria so as to increase superoxide levels or alter cellular ATP levels in the target cells. Method of the present invention are not limited to particular target cells. In some embodiments, the target cells are selected from the group consisting of in vitro cells, in vivo cells, ex vivo cells, cancer cells, B cells, T cells, and granulocytes. The present invention is not limited to a particular therapeutic application. Non-limiting examples of therapeutic applications for the present invention are described in the following subsections.

A. General Therapeutic Application

In particularly preferred embodiments, the compositions of the present invention are contemplated to provide therapeutic benefits to patients suffering from any one or more of a number of conditions (e.g., diseases characterized by dysregulation of necrosis and/or apoptosis processes in a cell or tissue, disease characterized by aberrant cell growth and/or hyperproliferation, etc.) by modulating (e.g., inhibiting or promoting) the activity of the mitochondrial ATP synthase (as referred to as mitochondrial $F_0F_1$ ATPase) complexes in affected cells or tissues. In further preferred embodiments, it is contemplated that the compositions of the present invention are used to treat immune/chronic inflammatory conditions (e.g., psoriasis). In even further embodiments, it is contemplated that the compositions of the present invention are used in conjunction with stenosis therapy to treat compromised (e.g., occluded) vessels.

In particularly preferred embodiments, it is contemplated that the compositions of the present invention inhibit the activity of mitochondrial ATP synthase complex by binding to a specific subunit of this multi-subunit protein complex. While the present invention is not limited to any particular mechanism, nor to any understanding of the action of the agents being administered, in some embodiments, it is contemplated that the compositions of the present invention bind to the oligomycin sensitivity conferring protein (OSCP) portion of the mitochondrial ATP synthase complex, to the OSCP/F1 junction, or to the F1 subunit. Likewise, it is further contemplated that when the compositions of the present invention bind to the OSCP the initial affect is overall inhibition of the mitochondrial ATP synthase complex, and that the downstream consequence of binding is a change in ATP or pH level and the production of reactive oxygen species (e.g., $O_2$—). In still other preferred embodiments, while the present invention is not limited to any particular mechanism, nor to any understanding of the action of the agents being administered, it is contemplated that the generation of free radicals ultimately results in cell killing. In yet other embodiments, while the present invention is not limited to any particular mechanism, nor to any understanding of the action of the agents being administered, it is contemplated that the inhibiting mitochondrial ATP synthase complex using the compositions and methods of the present invention provides therapeutically useful inhibition of cell proliferation.

Accordingly, it is contemplated that preferred methods embodied in the present invention, provide therapeutic benefits to patients by providing compounds of the present invention that modulate (e.g., inhibiting or promoting) the activity of the mitochondrial ATP synthase complexes in affected cells or tissues via binding to the oligomycin sensitivity conferring protein (OSCP) portion of the mitochondrial ATP synthase complex. Importantly, by itself the OSCP, the OSCP/F1 junction, or the F1 subunit has no biological activity.

Thus, in one broad sense, it is contemplated that preferred embodiments of the present invention are directed to the discovery that many diseases characterized by dysregulation of necrosis and/or apoptosis processes in a cell or tissue, or diseases characterized by aberrant cell growth and/or hyperproliferation, etc., can be treated by modulating the activity of the mitochondrial ATP synthase complex including, but not limited to, by binding to the oligomycin sensitivity conferring protein (OSCP) component thereof. The present invention is not intended to be limited, however, to the practice of the compositions and methods explicitly described herein. Indeed, those skilled in the art will appreciate that a number of additional compounds not specifically recited herein are suitable for use in the methods disclosed herein of modulating the activity of mitochondrial ATP synthase.

The present invention thus specifically contemplates that any number of suitable compounds presently known in the art, or developed later, can optionally find use in the methods of the present invention. For example, compounds including, but not limited to, oligomycin, ossamycin, cytovaricin, apoptolidin, bafilomyxcin, resveratrol, piceatannol, and dicyclohexylcarbodiimide (DCCD), and the like, find use in the methods of the present invention. The present invention is not intended, however, to be limited to the methods or compounds specified above. In one embodiment, that compounds potentially useful in the methods of the present invention may be selected from those suitable as described in the scientific literature. (See e.g., K. B. Wallace and A. A. Starkov, Annu. Rev. Pharmacol. Toxicol., 40:353-388 [2000]; A. R. Solomon et al., Proc. Nat. Acad. Sci. U.S.A., 97(26):14766-14771 [2000]).

In some embodiments, compounds potentially useful in methods of the present invention are screened against the National Cancer Institute's (NCI-60) cancer cell lines for efficacy. (See e.g., A. Monks et al., J. Natl. Cancer Inst., 83:757-766 [1991]; and K. D. Paull et al., J. Natl. Cancer Inst., 81:1088-1092 [1989]). Additional screens suitable screens (e.g., autoimmunity disease models, etc.) are within the skill in the art.

Those skilled in the art of preparing pharmaceutical compounds and formulations will appreciate that when selecting optional compounds for use in the methods disclosed herein, that suitability considerations include, but are not limited to, the toxicity, safety, efficacy, availability, and cost of the particular compounds.

In some embodiments, pharmaceutical compositions comprise compounds of the invention and, for example, therapeutic agents (e.g., antiatherosclerotic agents, anticoagulants, antithrombotic agents, antihypertensive agents, potassium channel openers, calcium channel blockers, sodium hydrogen exchanger inhibitors, antiarrhythmic agents, prothrombolytic agents, fibrinogen antagonists, diuretics, ATPase inhibitors, mineralocorticoid receptor antagonists, phosphodiesterase inhibitors, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, and antidiabetic agents). Antihypertensive agents include, but are not limited to, ACE inhibitors, AT-1 receptor antagonists, ET receptor antagonists, dual ET/AII receptor antagonists, and vasopepsidase inhibitors, or an anti-platelet agent selected from GPIIb/IIIa blockers, $P2Y_1$ and $P2Y_{12}$ antagonists, thromboxane receptor antagonists, and aspirin.

In some embodiments, the compounds of the present invention are useful in treating a mitochondrial $F_1F_0$ ATP hydrolase associated disorder (e.g., myocardial infarction, ventricular hypertrophy, coronary artery disease, non-Q wave MI, congestive heart failure, cardiac arrhythmias, unstable angina, chronic stable angina, Prinzmetal's angina, high blood pressure, intermittent claudication, peripheral occlusive arterial disease, thrombotic or thromboembolic symptoms of thromboembolic stroke, venous thrombosis, arterial thrombosis, cerebral thrombosis, pulmonary embolism, cerebral embolism, thrombophilia, disseminated intravascular coagulation, restenosis, atrial fibrillation, ventricular enlargement, atherosclerotic vascular disease, atherosclerotic plaque rupture, atherosclerotic plaque formation, transplant atherosclerosis, vascular remodeling atherosclerosis, cancer, surgery, inflammation, systematic infection, artificial surfaces, interventional cardiology, immobility, medication, pregnancy and fetal loss, and diabetic complications comprising retinopathy, nephropathy and neuropathy) in a patient.

B. Immune Disorder, Autoimmune Disorder, and Chronic Inflammatory Disorder Therapeutic Application Immune disorders and chronic inflammatory disorders often result from dysfunctional cellular proliferation regulation and/or cellular apoptosis regulation. Mitochondria perform a key role in the control and execution of cellular apoptosis. The mitochondrial permeability transition pore (MPTP) is a pore that spans the inner and outer mitochondrial membranes and functions in the regulation of proapoptotic particles. Transient MPTP opening results in the release of cytochrome c and the apoptosis inducing factor from the mitochondrial intermembrane space, resulting in cellular apoptosis.

The oligomycin sensitivity conferring protein (OSCP) is a subunit of the $F_0F_1$ mitochondrial ATP synthase/ATPase and functions in the coupling of a proton gradient across the $F_0$ sector of the enzyme in the mitochondrial membrane. In some embodiments, it is contemplated that compounds of the present invention bind the OSCP, the OSCP/F1 junction, or the F1 subunit, increases superoxide and cytochrome c levels, increases cellular apoptosis, and inhibits cellular proliferation. The adenine nucleotide translocator (ANT) is a 30 kDa protein that spans the inner mitochondrial membrane and is central to the mitochondrial permeability transition pore (MPTP). Thiol oxidizing or alkylating agents are powerful activators of the MPTP that act by modifying one or more of three unpaired cysteines in the matrix side of the ANT. 4-(N—(S-glutathionylacetyl)amino) phenylarsenoxide, inhibits the ANT.

In certain embodiments, the present invention provides a method for treating an immune disorder (e.g., graph versus host disease, rheumatoid arthritis, or systemic lupus erythematosus), a hyperproliferative disorder (e.g., cancer), or a chronic inflammatory disease (e.g., asthma or psoriasis). In certain embodiments, the cancer is myeloma, bladder cancer, or renal cancer.

C. Treatment of Epidermal Hyperplasia

Epidermal hyperplasia (e.g., excessive keratinocyte proliferation) leading to a significant thickening of the epidermis in association with shedding of the thickened epidermis, is a feature of diseases such as psoriasis (see, e.g., Krueger G C, et al., (1984) J. Am. Acad. Dermatol. 11: 937-947; Fry L. (1988), Brit. J. Dermatol. 119:445-461; each herein incorporated by reference in their entireties) and also occurs under physiological conditions (e.g., during wound-healing).

Topical treatment of the skin with all-trans retinoic acid (RA) or its precursor, all-trans retinol (ROL) also results in epidermal hyperplasia (see, e.g., Varani J, et al., (2001) J. Invest. Dermatol, 117:1335-1341; herein incorporated by reference in its entirety). While the underlying etiologies are different, all of these hyperplasias have in common the activation of the epidermal growth factor (EGF) receptor in the proliferating keratinocytes (see, e.g., Varani J, et al., (2001) J. Invest. Dermatol 117:1335-1341; Baker B S, et al., (1992) Brit. J. Dermatol. 126:105-110; Gottlieb A B, et al., (1988) J. Exp. Med. 167:670-675; Elder J T, et al., (1989) Science 243:811-814; Piepkorn M, et al., (1998) J Invest Dermatol 111:715-721; Piepkorn M, et al., (2003) Arch Dermatol Res 27:27; Cook P W, et al., (1992) Cancer Res 52:3224-3227; each herein incorporated by reference in their entireties). Normal epidermal growth does not appear to be as dependent on EGF receptor function as hyperplastic growth (see, e.g., Varani J, et al., (2001) J. Invest. Dermatol 117:1335-1341; Varani J, et al., (1998) Pathobiology 66:253-259; each herein incorporated by reference in their entireties). Likewise, function of the dermis in intact skin does not depend on EGF receptor function (see, e.g., Varani J, et al., (2001) J. Invest. Dermatol 117:1335-1341; herein incorporated by reference in its entirety).

The central role of the EGF receptor in regulating hyperplastic epithelial growth makes the EGF receptor tyrosine kinase a target for antiproliferative agents. Likewise, the series of signaling molecules engaged downstream of this receptor are additional points at which keratinocyte growth can be interrupted. The mitogen activated protein kinase (MAPK) cascade is activated by the EGF receptor (see, e.g., Marques, S. A., et al., (2002) J Pharmacol Exp Ther 300, 1026-1035; herein incorporated by reference in its entirety). In hyperproliferative epidermis, but not in normal epidermis, extracellular signal-regulated kinases 1/2 (Erk 1/2) are activated in basal and suprabasal keratinocytes and contribute to epidermal hyperproliferation (see, e.g., Haase, I., et al., (2001) J Clin Invest 108, 527-536; Takahashi, H., et al., (2002) J Dermatol Sci 30, 94-99; each herein incorporated by reference in their entireties). In culture models, keratinocyte growth regulation through the EGF receptor results in increased MAPK activity. In keratinocytes, growth factor-stimulated MAPK activity is also dependent on integrin engagement and extracellular matrix molecules that bind integrins are capable of independently activating MAPKs and increasing keratinocyte proliferation (see, e.g., Haase, I., et al., (2001) J Clin Invest 108, 527-536; herein incorporated by reference in its entirety). The proliferation of other skin cells, including fibroblasts, is less dependent on Erk 1/2 activity, making Erk inhibition a potentially useful characteristic to evaluate lead compounds for potential utility against epidermal hyperplasia.

In some embodiments, it is contemplated that compounds of the present invention are useful for treating epidermal hyperplasias.

In some embodiments, it is contemplated that compounds of the present invention (e.g., Bz-423) are useful in treating psoriasis. Psoriasis is common and chronic epidermal hyperplasia. Plaque psoriasis is the most common type of psoriasis and is characterized by red skin covered with silvery scales and inflammation. Patches of circular to oval shaped red plaques that itch or burn are typical of plaque psoriasis. The patches are usually found on the arms, legs, trunk, or scalp but may be found on any part of the skin. The most typical areas are the knees and elbows. Psoriasis is not contagious and can be inherited. Environmental factors, such as smoking, sun exposure, alcoholism, and HIV infection, may affect how often the psoriasis occurs and how long the flares up last.

Treatment of psoriasis includes topical steroids, coal tar, keratolytic agents, vitamin D-3 analogs, and topical retinoids. Topical steroids are agents used to reduce plaque formation. Topical steroid agents have anti-inflammatory effects and may cause profound and varied metabolic activities. In addition, topical steroid agents modify the body's immune response to diverse stimuli. Examples of topical steroids include, but are not limited to, triamcinolone acetonide (Artistocort, Kenalog) 0.1% cream, and betamethasone diproprionate (Diprolene, Diprosone) 0.05% cream. Coal tar is an inexpensive treatment available over the counter in shampoos or lotions for use in widespread areas of involvement. Coal tar is particularly useful in hair-bearing areas. An example of coal tar is coal tar 2-10% (DHS Tar, Doctar, Theraplex T)—antipruitic. Keratolytic agents are used to remove scale, smooth the skin, and to treat hyperkeratosis. An example of a keratolytic agent is anthralin 0.1-1% (Drithocreme, Anthra-Derm). Vitamin D-3 analogs are used in patients with lesions resistant to older therapy or with lesions on the face or exposed areas where thinning of the skin would pose cosmetic problems. An example of a vitamin D-3 analog is calcipotriene (Dovonex). Topical retinoids are agents that decrease the cohesiveness of follicular epithelial cells and stimulate mitotic activity, resulting in an increase in turnover of follicular epithelial cells. Examples of topical retinoids include, but are not limited to, tretinoin (Retin-A, Avita), and tazarotene (Tazorac).

Approximately 1-2% of people in the United States, or about 5.5 million, have plaque psoriasis. Up to 30% of people with plaque psoriasis also have psoriatic arthritis. Individuals with psoriatic arthritis have inflammation in their joints and may have other arthritis symptoms. Sometimes plaque psoriasis can evolve into more severe disease, such as pustular psoriasis or erythrodermic psoriasis. In pustular psoriasis, the red areas on the skin contain blisters with pus. In erythrodermic psoriasis, a wide area of red and scaling skin is typical, and it may be itchy and painful. The present invention is useful in treating additional types of psoriasis, including but not limited to, guttate psoriasis, nail psoriasis, inverse psoriasis, and scalp psoriasis.

In some embodiments, the compounds of the present invention are useful in treating pigmentation disorders (e.g., albinism, melasma, and vitiligo). The present invention is not limited to a particular mechanism for treating pigment disorders. In some embodiments, pigment disorders are treated through targeting of the $F_1F_0$-ATPase by the compounds of the present invention. In further embodiments, pigment disorders are treated through the rerouting of tyrosinase by the compounds of the present invention. In further embodiments, pigment disorders are treated through targeting of prohibition by the compounds of the present invention.

D. Stenosis Therapy

In some embodiments, the compositions of the present invention are used in conjunction with stenosis therapy to treat compromised (e.g., occluded) vessels. In further embodiments, the compositions of the present invention are used in conjunction with stenosis therapy to treat compromised cardiac vessels.

Vessel stenosis is a condition that develops when a vessel (e.g., aortic valve) becomes narrowed. For example, aortic valve stenosis is a heart condition that develops when the valve between the lower left chamber (left ventricle) of the heart and the major blood vessel called the aorta becomes narrowed. This narrowing (e.g., stenosis) creates too small a space for the blood to flow to the body. Normally the left ventricle pumps oxygen-rich blood to the body through the aorta, which branches into a system of arteries throughout the body. When the heart pumps, the 3 flaps, or leaflets, of the aortic valve open one way to allow blood to flow from the ventricle into the aorta. Between heartbeats, the flaps close to form a tight seal so that blood does not leak backward through the valve. If the aortic valve is damaged, it may become narrowed (stenosed) and blood flow may be reduced to organs in the body, including the heart itself. The long-term outlook for people with aortic valve stenosis is poor once symptoms develop. People with untreated aortic valve stenosis who develop symptoms of heart failure usually have a life expectancy of 3 years or less.

Several types of treatment exist for treating compromised valves (e.g., balloon dilation, ablation, atherectomy or laser treatment). One type of treatment for compromised cardiac valves is angioplasty. Angioplasty involves inserting a balloon-tipped tube, or catheter, into a narrow or blocked artery in an attempt to open it. By inflating and deflating the balloon several times, physicians usually are able to widen the artery.

A common limitation of angioplasty or valve expansion procedures is restenosis. Restenosis is the reclosure of a peripheral or coronary artery following trauma to that artery caused by efforts to open a stenosed portion of the artery, such as, for example, by balloon dilation, ablation, atherectomy or laser treatment of the artery. For these angioplasty procedures, restenosis occurs at a rate of about 20-50% depending on the definition, vessel location, lesion length and a number of other morphological and clinical variables. Restenosis is believed to be a natural healing reaction to the injury of the arterial wall that is caused by angioplasty procedures. The healing reaction begins with the thrombotic mechanism at the site of the injury. The final result of the complex steps of the healing process can be intimal hyperplasia, the uncontrolled migration and proliferation of medial smooth muscle cells, combined with their extracellular matrix production, until the artery is again stenosed or occluded.

In an attempt to prevent restenosis, metallic intravascular stents have been permanently implanted in coronary or peripheral vessels. The stent is typically inserted by catheter into a vascular lumen told expanded into contact with the diseased portion of the arterial wall, thereby providing mechanical support for the lumen. However, it has been found that restenosis can still occur with such stents in place. Also, the stent itself can cause undesirable local thrombosis. To address the problem of thrombosis, persons receiving stents also receive extensive systemic treatment with anticoagulant and antiplatelet drugs.

To address the restenosis problem, it has been proposed to provide stents which are seeded with endothelial cells (Dichek, D. A. et al Seeding of Intravascular Stents With Genetically Engineered Endothelial Cells; Circulation 1989; 80: 1347-1353). In that experiment, sheep endothelial cells that had undergone retrovirus-mediated gene transfer for either bacterial beta-galactosidase or human tissue-type plasminogen activator were seeded onto stainless steel stents and grown until the stents were covered. The cells were therefore able to be delivered to the vascular wall where they could provide therapeutic proteins. Other methods of providing therapeutic substances to the vascular wall by means of stents have also been proposed such as in international patent application WO 91/12779 "Intraluminal Drug Eluting Prosthesis" and international patent application WO 90/13332 "Stent With Sustained Drug Delivery". In those applications, it is suggested that antiplatelet agents, anticoagulant agents, antimicrobial agents, anti-inflammatory agents, antimetabolic agents and other drugs could be supplied in stents to reduce the incidence of restenosis. Further, other vasoreactive agents such as nitric oxide releasing agents could also be used.

An additional cause of restenosis is the over-proliferation of treated tissue. In some embodiments, the anti-proliferative properties of the present invention inhibit restenosis. Drug-eluting stents are well known in the art (see, e.g., U.S. Pat. No. 5,697,967; U.S. Pat. No. 5,599,352; and U.S. Pat. No. 5,591,227; each of which are herein incorporated by reference). In some embodiments, the compositions of the present invention are eluted from drug-eluting stents in the treatment of compromised (e.g., occluded) vessels. In further embodiments, the compositions of the present invention are eluted from drug-eluting stents in the treatment of compromised cardiac vessels.

E. Treatment of Bacterial Infections

In some embodiments, benzodiazepine compounds and related compounds (see, e.g., Section III—Exemplary Compounds) are used to treat a subject suffering from a bacterial infection. In some embodiments, more than one of the compounds of the present invention are used to treat a subject suffering from a bacterial infection. In some embodiments, the compounds of the present invention treat bacterial infections through modulating (e.g., inhibiting or promoting) the activity of ATP synthase complexes (e.g., mitochondrial ATP synthase complexes or homolog in organisms that do not have mitochondria) in affected cells or tissues via binding to the oligomycin sensitivity conferring protein (OSCP) portion/F1 of the ATP synthase complex (e.g., mitochondrial ATP synthase complex). The present invention is not limited to particular types of bacterial infections. Examples of bacterial infections include, but are not limited to, Anthrax, Bacterial Meningitis, Brucellosis, Campylobacteriosis, Cat Scratch Disease, Cholera, Diphtheria, Epidemic Typhus, Gonorrhea, Impetigo—Legionellosis, Leprosy (Hansen's Disease), Leptospirosis, Listeriosis, Lyme Disease, Meloidosis, MRSA infection, Nocardiosis, Pertussis (Whooping Cough), Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Typhus; and Urinary Tract Infections. In some embodiments, the compounds of the present invention are co-administered with at least one additional agent for purposes of treating bacterial infections. Examples of addition agents for purposes of treating bacterial infections include, but are not limited to, Cephalosporins, Macrolides, Penicillins, Quinolones, Sulfonamides and Related Compounds, and Tetracyclines.

F. Treatment of Viral Infections

In some embodiments, benzodiazepine compounds and related compounds (see, e.g., Section III—Exemplary Compounds) are used to treat a subject suffering from a viral infection. In some embodiments, more than one of the compounds of the present invention are used to treat a subject suffering from a viral infection. In some embodiments, the compounds of the present invention treat viral infections through modulating (e.g., inhibiting or promoting) the activity of ATP synthase complexes (e.g., mitochondrial ATP synthase complexes or homolog in organisms that do not have mitochondria) in affected cells or tissues via binding to the oligomycin sensitivity conferring protein (OSCP) portion/F1 of the ATP synthase complex (e.g., mitochondrial ATP synthase complex). The present invention is not limited to particular types of viral infections. Examples of viral infections include, but are not limited to, AIDS, AIDS Related Complex, Chickenpox (Varicella), Common cold, Cytomegalovirus Infection, Colorado tick fever, Dengue fever, Ebola haemorrhagic fever, Epidemic parotitis, Hand, foot and mouth disease, Hepatitis, Herpes simplex, Herpes zoster, HPV, Influenza (Flu), Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease, and Yellow fever. In some embodiments, the compounds of the present invention are co-administered with at least one additional agent for purposes of treating viral infections. Examples of additional agents for purposes of treating viral infections include, but are not limited to, Ganciclovir, Interferon-alpha-2b, Acyclovir, Famciclovir, and Valaciclovir.

G. Treatment of Fungal Infections

In some embodiments, benzodiazepine compounds and related compounds (see, e.g., Section III—Exemplary Compounds) are used to treat a subject suffering from a fungal infection. In some embodiments, more than one of the compounds of the present invention are used to treat a subject suffering from a fungal infection. In some embodiments, the compounds of the present invention treat fungal infections through modulating (e.g., inhibiting or promoting) the activity of ATP synthase complexes (e.g., mitochondrial ATP synthase complexes or homolog in organisms that do not have mitochondria) in affected cells or tissues via binding to the oligomycin sensitivity conferring protein (OSCP) portion/F1 of the ATP synthase complex (e.g., mitochondrial ATP synthase complex). The present invention is not limited to particular types of fungal infections. Examples of fungal infections include, but are not limited to, Aspergillosis, Blastomycosis, Candidiasis, Coccidioidomycosis, Cryptococcosis, Histoplasmosis, Tinea pedis. In, some embodiments, the compounds of the present invention are co-administered with at least one additional agent for purposes of treating fungal infections. Examples of additional agents for purposes of treating fungal infections include, but are not limited to, betamethasone, butenafine, ciclopirox, clioquinol, hydrocortisone, clotrimazole, econazole, flucytosine, griseofulvin, haloprogin, itraconazole, ketoconazole, miconazole, naftifine, nystatin, triamcinolone, oxiconazole, sulcanazole, terbinafine, terconazole, tolnaftate, and voriconazole.

H. Treatment of Parasitic Infections

In some embodiments, benzodiazepine compounds and related compounds (see, e.g., Section III—Exemplary Compounds) are used to treat a subject suffering from a parasitic infection. In some embodiments, more than one of the compounds of the present invention are used to treat a subject suffering from a parasitic infection. In some embodiments, the compounds of the present invention treat parasitic infections through modulating (e.g., inhibiting or promoting) the activity of ATP synthase complexes (e.g., mitochondrial ATP synthase complexes or homolog in organisms that do not have mitochondria) in affected cells or tissues via binding to the oligomycin sensitivity conferring protein (OSCP) portion/F1 of the ATP synthase complex (e.g., mitochondrial ATP synthase complex). The present invention is not limited to particular types of parasitic infections. Examples of parasitic infections include, but are not limited to, African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, and Trypanosomiasis. In some embodiments, the compounds of the present invention are co-administered with at least one additional agent for purposes of treating parasitic infections.

Examples of additional agents for purposes of treating parasitic infections include, but are not limited to, antihelminthic agents (e.g., albendazole (Albenza), mebendazole (Vermox), niclosamide (Niclocide), oxamniquine (Vansil), praziquantel (Biltricide), pyrantel (Antiminth), pyantel pamoate (Antiminth), thiabendazole (Mintezol), bitional, ivermectin, and diethylcarbamazepine citrate.

I. Treatment of Prion Infectious Diseases

In some embodiments, benzodiazepine compounds and related compounds (see, e.g., Section III—Exemplary Compounds) are used to treat a subject suffering from a prion infectious disease. In some embodiments, more than one of the compounds of the present invention are used to treat a subject suffering from a prion infectious disease. In some embodiments, the compounds of the present invention treat prion infectious diseases through modulating (e.g., inhibiting or promoting) the activity of ATP synthase complexes (e.g., mitochondrial ATP synthase complexes or homolog in organisms that do not have mitochondria) in affected cells or tissues via binding to the oligomycin sensitivity conferring protein (OSCP) portion/F1 of the ATP synthase complex (e.g., mitochondrial ATP synthase complex). The present invention is not limited to particular types of prion infectious diseases. Examples of parasitic infectious diseases include, but are not limited to, transmissible spongiform encephalopathy, Bovine spongiform encephalopathy, Creutzfeldt-Jakob disease, and Kuru. In some embodiments, the compounds of the present invention are co-administered with at least one additional agent for purposes of treating prion infectious diseases. Examples of additional agents for purposes of treating prion infectious diseases include, but are not limited to, Congo red and its analogs, anthracyclines, amphotericin B and its analogs, sulfated polyanions, and tetrapyrroles.

J. Treatment of Diseases Involving Aberrant Angiogenesis

In some embodiments, benzodiazepine compounds and related compounds (see, e.g., Section III—Exemplary Compounds) are used to treat a subject suffering from a disease involving aberrant angiogenesis. In some embodiments, more than one of the compounds of the present invention are used to treat diseases involving aberrant angiogenesis through modulating (e.g., inhibiting or promoting) the activity of ATP synthase complexes (e.g., mitochondrial ATP synthase complexes) in affected cells or tissues undergoing aberrant angiogenesis via binding to the oligomycin sensitivity conferring protein (OSCP) portion/F1 of the ATP synthase complex (e.g., mitochondrial ATP synthase complex). The present invention is not limited to particular types of disease involving aberrant angiogenesis. Examples of diseases involving aberrant angiogenesis include, but are not limited to, cancers (e.g., cancers involving solid tumors), psoriasis, diabetic retinopathy, macular degeneration, atherosclerosis and rheumatoid arthritis.

Examples of additional agents for treating diseases involving aberrant angiogenesis include, but are not limited to, Dalteparin, ABT-510, CNGRC peptide TNF alpha conjugate (NGR-TNF), Combretastatin A4 Phosphate, Dimethylxanthenone Acetic Acide, Lenalidomide, LY317615, PPI-2458, Soy Isoflavone (Genistein; Soy Protein Isolate), Tamoxifen Citrate, Thalidomide, ADH-1, AG-013736, AMG-706, Anti-VEGF Antibody, AZD2171, Bay 43-9006, GW786034, CHIR-265, PI-88, PTK787/ZK 222584, RAD001, Suramin, SU11248, XL184, ZD6474, ATN-161, EMD 121974, and Celecoxib. Additional agents for treating diseases involving aberrant angiogenesis include anti-cancer drugs, such as the anticancer drugs described above in the Exemplary Compounds section.

K. Blood Pressure Regulation

In some embodiments, benzodiazepine compounds and related compounds (see, e.g., Section III—Exemplary Compounds) are used to regulate a subject's blood pressure. In some embodiments, more than one of the compounds of the present invention are used to treat regulate a subject's blood pressure (e.g., maintain a subject's blood pressure within a desired range). In some embodiments, the compounds of the present invention regulate blood pressure through modulating (e.g., inhibiting or promoting) the activity of ATP synthase complexes (e.g., mitochondrial ATP synthase complexes) in affected cells or tissues via binding to the oligomycin sensitivity conferring protein (OSCP) portion/F1 of the ATP synthase complex (e.g., mitochondrial ATP synthase complex). In some embodiments, the compounds of the present invention are co-administered with at least one additional agent for purposes of regulating a subject's blood pressure. Examples of additional agents for purposes of regulating a subject's blood pressure include, but are not limited to, thiazides and related diuretics (e.g., hydrochlorothiazide, chlorthalidone), alpha/beta-adrenergic blocking agents (e.g., carvedilol), beta-adrenergic blocking agents (e.g., bisoprolol, atenolol, metoprolol), angiotensin-converting enzyme inhibitors (e.g., captopril, fosinopril, benazepril, quinapril, ramipril), angiotensin II receptor antagonists (e.g., losartan, valsartan, candesartan, irbesartan, eprosartan, and olmesartan), calcium channel blockers—nondihydropyridines (e.g., diltiazem, and verapamil), calcium channel blockers—dihydropyridines (e.g., Amlodipine, nifedipine, felodipine), vasodilators—peripheral (e.g., hydralazine), aldosterone antagonists (e.g., spironolactone).

L. HDL/LDL Regulation

In some embodiments, benzodiazepine compounds and related compounds (see, e.g., Section III—Exemplary Compounds) are used to regulate a subject's HDL/LDL levels. In some embodiments, more than one of the compounds of the present invention are used to treat regulate a subject's HDL/LDL levels (e.g., lower a subject's LDL levels, raise a subject's HDL levels). In some embodiments, the compounds of the present invention regulate HDL/LDL levels through modulating (e.g., inhibiting or promoting) the activity of ATP synthase complexes (e.g., mitochondrial ATP synthase complexes) in affected cells or tissues via binding to the oligomycin sensitivity conferring protein (OSCP) portion/F1 of the ATP synthase complex (e.g., mitochondrial ATP synthase complex). In some embodiments, the compounds of the present invention are co-administered with at least one additional agent for purposes of regulating a subject's HDL/LDL levels. Examples of additional agents for purposes of regulating a subject's HDL/LDL levels include, but are not limited to, antilipemic agents (e.g., niacin, nicotinic acid, gemfibrozil, fenofibrate), and HMG-CoA reductase inhibitors (e.g., atorvastatin, simvastatin, pravastatin, lovastatin, fluvastatin, and rosuvastatin).

VI. ATPase Inhibitors and Methods for Identifying Therapeutic Inhibitors

The present invention provides compounds that target the $F_1F_o$-ATPase. In addition, the present invention provides compounds that target the $F_1F_o$-ATPase as a treatment for disorders (e.g., hyperproliferative disorders, autoimmune disorders), and in particular, compounds with low toxicity. The present invention further provides methods of identifying compounds that target the $F_1F_o$-ATPase. Additionally, the present invention provides therapeutic applications for compounds targeting the $F_1F_o$-ATPase.

A majority of ATP within eukaryotic cells is synthesized by the mitochondrial $F_1F_o$-ATPase (see, e.g., C. T. Gregory et al, J. Immunol., 139:313-318 [1987]; J. P. Portanova et al., Mol. Immunol., 32:117-135 [1987]; M. J. Shlomchik et al., Nat. Rev. Immunol., 1:147-153 [2001]; each herein incorporated by reference in their entireties). Although the $F_1F_o$-ATPase synthesizes and hydrolyzes ATP, during normal physiologic conditions, the $F_1F_o$-ATPase only synthesizes ATP (see, e.g., Nagyvary J, et al., Biochem. Educ. 1999; 27:193-99; herein incorporated by reference in its entirety). The mitochondrial $F_1F_o$-ATPase is composed of three major domains: $F_o$, $F_1$ and the peripheral stator. $F_1$ is the portion of the enzyme that contains the catalytic sites and it is located in the matrix (see, e.g., Boyer, P D, Annu Rev Biochem. 1997; 66:717-49; herein incorporated by reference in its entirety). This domain is highly conserved and has the subunit composition $\alpha_3\beta_3\gamma\delta\epsilon$. The landmark X-ray structure of bovine $F_1$ revealed that $\alpha_3\beta_3$ forms a hexagonal cylinder with the $\gamma$ subunit in the center of the cylinder. $F_o$ is located within the inner mitochondrial membrane and contains a proton channel. Translocation of protons from the inner-membrane space into the matrix provides the energy to drive ATP synthesis. The peripheral stator is composed of several proteins that physically and functionally link $F_o$ with $F_1$. The stator transmits conformational changes from $F_o$ into in the catalytic domain that regulate ATP synthesis (see, e.g., Cross R L, Biochim Biophys Acta 2000; 1458:270-75; herein incorporated by reference in its entirety).

$F_1F_o$-ATPase inhibitors are invaluable tools for mechanistic studies of the $F_1F_o$-ATPase (see, e.g., James A M, et al., J Biomed Sci 2002; 9:475-87; herein incorporated by reference in its entirety). Because $F_1F_o$-ATPase inhibitors are often cytotoxic, they have been explored as drugs for cancer and other hyperproliferative disorders. Macrolides (e.g., oligomycin and apoptolidin) are non-competitive inhibitors of the $F_1F_o$-ATPase (see, e.g., Salomon A R, et al., PNAS 2000; 97:14766-71; Salomon A R, et al., Chem Biol 2001; 8:71-80; herein incorporated by reference). Macrolides bind to $F_o$ which blocks proton flow through the channel resulting in inhibition of the $F_1F_o$-ATPase. Macrolides are potent (e.g., the $IC_{50}$ for oligomycin=10 nM) and lead to large decreases in [ATP]. As such, macrolides have an unacceptably narrow therapeutic index and are highly toxic (e.g., the $LD_{50}$ for oligomycin in rodents is two daily doses at 0.5 mg/kg) (see, e.g., Kramar R, et al., Agents & Actions 1984, 15:660-63; herein incorporated by reference in its entirety). Other inhibitors of $F_1F_o$-ATPase include Bz-423, which binds to the OSCP in $F_1$ (as described elsewhere herein). Bz-423 has an $K_i$~9 μM.

In cells that are actively respiring (known as state 3 respiration), inhibiting $F_1F_o$-ATPase blocks respiration and places the mitochondria in a resting state (known as state 4). In state 4, the MRC is reduced relative to state 3, which favors reduction of $O_2$ to $O_2^-$ at complex III (see, e.g., N. Zamzami et al., J. Exp. Med., 181:1661-1672 [1995]; herein incorporated by reference in its entirety). For example, treating cells with either oligomycin or Bz-423 leads to a rise of intracellular $O_2^-$ as a consequence of inhibiting complex V. In the case of oligomycin, supplementing cells with ATP protects against death whereas antioxidants do not, indicating that cell death results from the drop in ATP (see, e.g., Zhang J G, et al., Arch Biochem Biophys 2001; 393:87-96; McConkey D J, et al., The ATP switch in apoptosis. In: Nieminen La, ed. Mitochondria in pathogenesis. New York: Plenum, 2001:265-77; each herein incorporated by reference in their entireties). Bz-423-induced cell death is blocked by antioxidants and is not affected by supplementing cells with ATP, indicating that Bz-423 engages an ROS-dependent death response (see, e.g., N. B. Blatt, et al., J. Clin. Invest., 2002, 110, 1123; herein incorporated by reference in its entirety). As such, $F_1F_o$-ATPase inhibitors are either toxic (e.g., oligomycin) or therapeutic (e.g., Bz-423).

The present invention provides a method of distinguishing toxic $F_1F_o$-ATPase inhibitors from therapeutic $F_1F_o$-ATPase inhibitors. $F_1F_o$-ATPase inhibitors with therapeutic potential (e.g., Bz-423) present a novel mode of inhibition. Specifically, $F_1F_o$-ATPase inhibitors with beneficial properties like Bz-423 are uncompetitive inhibitors that only bind enzyme-substrate complexes at high substrate concentration, do not alter the $k_{cat}/K_m$ ratio, and dissociate from the enzyme-substrate complex at a dissociation rate of approximately $0.2$ s$^{-1}$ (e.g., $0.01$ s$^{-1}$; $0.05$ s$^{-1}$; $0.01$ s$^{-1}$; $0.15$ s$^{-1}$; $0.25$ s$^{-1}$; $0.3$ s$^{-1}$; $0.5$ s$^{-1}$).

The present invention provides compounds that target the $F_1F_o$-ATPase as a disorder (e.g., hyperproliferative disorder, autoimmune disorder) treatment. In particular, the present invention provides methods of identifying compounds that target the $F_1F_o$-ATPase while not altering the $k_{cat}/K_m$ ratio and dissociate from the enzyme-substrate complex at a dissociation rate of approximately $0.2$ s$^{-1}$ (e.g., $0.01$ s$^{-1}$; $0.05$ s$^{-1}$; $0.01$ s$^{-1}$; $0.15$ s$^{-1}$; $0.25$ s$^{-1}$; $0.3$ s$^{-1}$; $0.5$ s$^{-1}$). Additionally, the present invention provides therapeutic applications for compounds targeting the $F_1F_o$-ATPase.

A. ATPase Inhibiting Compounds

The present invention provides compounds that inhibit the $F_1F_o$-ATPase. In some embodiments, the compounds do not bind free $F_1F_o$-ATPase, but rather bind to an $F_1F_o$-ATPase-substrate complex. The compounds show maximum activity at high substrate concentration and minimal activity (e.g., $F_1F_o$-ATPase inhibiting) at low substrate concentration. In preferred embodiments, the compounds do not alter the $k_{cat}/K_m$ ratio of the $F_1F_o$-ATPase and dissociate from the enzyme-substrate complex at a dissociation rate of approximately $0.2$ s$^{-1}$ (e.g., $0.01$ s$^{-1}$; $0.05$ s$^{-1}$; $0.1$ s$^{-1}$; $0.15$ s'; $0.25$ s$^{-1}$; $0.3$ s$^{-1}$; $0.5$ s$^{-1}$). The properties of the $F_1F_o$-ATPase inhibitors of the present invention are in contrast with oligomycin, which is a $F_1F_o$-ATPase inhibitor that is acutely toxic and lethal. Oligomycin is a noncompetitive inhibitor, which binds to both free $F_1F_o$-ATPase and $F_1F_o$-ATPase-substrate complexes and alters the $k_{cat}/K_m$ ratio. The properties of the $F_1F_o$-ATPase inhibitors of the present invention dissociate from the enzyme-substrate complex at a faster rate than with oligomycin.

The compounds of the present invention that inhibit $F_1F_o$-ATPase while not altering the $k_{cat}/K_m$ ratio, in some embodiments, have the structure described elsewhere herein. However, compounds of other structures that are identified as therapeutic inhibitors by the methods of the present invention are also encompassed by the present invention.

B. Identifying ATPase Inhibitors

The present invention provides methods of identifying (e.g., screening) compounds useful in treating autoimmune disorders. The present invention is not limited to a particular type compound. In preferred embodiments, compounds of the present invention include, but are not limited to, pharmaceutical compositions, small molecules, antibodies, large molecules, synthetic molecules, synthetic polypeptides, synthetic polynucleotides, synthetic nucleic acids, aptamers, polypeptides, nucleic acids, and polynucleotides. The present invention is not limited to a particular method of identifying compounds useful in treating autoimmune disorders. In preferred embodiments, compounds useful in treating autoimmune disorders are identified as possessing an ability to inhibit an $F_1F_o$-ATPase while not altering the $k_{cat}/K_m$ ratio and dissociate from the enzyme-substrate complex at a dissociation rate of approximately 0.2 s$^{-1}$ (e.g., 0.01 s$^{-1}$; 0.05 s$^{-1}$; 0.1 s$^{-1}$; 0.15 s$^{-1}$; 0.25 s$^{-1}$; 0.3 s$^{-1}$; 0.5 s$^{-1}$).

C. Therapeutic Applications with $F_1F_o$-ATPase Inhibitors

In certain embodiments, the exemplary compounds of the present invention can be useful in treating certain $F_1F_0$ ATP hydrolase associated disorders. Examples of $F_1F_0$ ATP hydrolase associated disorders include, but are not limited to, myocardial infarction, ventricular hypertrophy, coronary artery disease, non-Q wave MI, congestive heart failure, cardiac arrhythmias, unstable angina, chronic stable angina, Prinzmetal's angina, high blood pressure, intermittent claudication, peripheral occlusive arterial disease, thrombotic or thromboembolic symptoms of thromboembolic stroke, venous thrombosis, arterial thrombosis, cerebral thrombosis, pulmonary embolism, cerebral embolism, thrombophilia, disseminated intravascular coagulation, restenosis, atrial fibrillation, ventricular enlargement, atherosclerotic vascular disease, atherosclerotic plaque rupture, atherosclerotic plaque formation, transplant atherosclerosis, vascular remodeling atherosclerosis, cancer, surgery, inflammation, systematic infection, artificial surfaces, interventional cardiology, immobility, pregnancy and fetal loss, and diabetic complications comprising retinopathy, nephropathy and neuropathy.

The present invention provides methods for treating disorders (e.g. neurodegenerative diseases, Alzheimers, ischemia reprofusion injury, neuromotor disorders, non-Hodgkin's lymphoma, lymphocytic leukemia, cutaneous T cell leukemia, an autoimmune disorder, cancer, solid tumors, lymphomas, and leukemias). The present invention is not limited to a particular form of treatment. In preferred embodiments, treatment includes, but is not limited to, symptom amelioration, symptom prevention, disorder prevention, and disorder amelioration. The present invention provides methods of treating autoimmune disorders applicable within in vivo, in vitro, and/or ex vivo settings.

In some embodiments, the present invention treats autoimmune disorders through inhibiting of target cells. The present invention is not limited to a particular form of cell inhibition. In preferred embodiments, cell inhibition includes, but is not limited to, cell growth prevention, cell proliferation prevention, and cell death. In preferred embodiments, inhibition of a target cell is accomplished through contacting a target cell with an $F_1F_o$-ATPase inhibitor of the present invention. In further embodiments, target cell inhibition is accomplished through targeting of the $F_1F_o$-ATPase with an $F_1F_o$-ATPase inhibitor of the present invention. The present invention is not limited to a particular $F_1F_o$-ATPase inhibitor. In preferred embodiments, the $F_1F_o$-ATPase inhibitor possesses the ability to inhibit an $F_1F_o$-ATPase while not altering the $k_{cat}/K_m$ ratio and dissociate from the enzyme-substrate complex at a dissociation rate of approximately 0.2 s$^{-1}$ (e.g., 0.01 s$^{-1}$; 0.05 s$^{-1}$; 0.01 s$^{-1}$; 0.15 s$^{-1}$; 0.25 s$^{-1}$; 0.3 s$^{-1}$; 0.5 s$^{-1}$). In further preferred embodiments, the $F_1F_o$-ATPase inhibitor is Bz-423 or other compounds described herein.

The present invention further provides methods for selectively inhibiting the pathology of target cells in a subject in need of therapy. The present invention is not limited to a particular method of inhibition target cell pathology. In preferred embodiments, target cell pathology is inhibited through administration of an effective amount of a compound of the invention. The present invention is not limited to a particular compound. In preferred embodiments, the compound is an $F_1F_o$-ATPase inhibitor. In further preferred embodiments, the compound inhibits the $F_1F_o$-ATPase while not altering the $k_{cat}/K_m$ ratio and dissociates from the enzyme-substrate complex at a dissociation rate of approximately 0.2 s$^{-1}$ (e.g., 0.01 s$^{-1}$; 0.05 s$^{-1}$; 0.01 s$^{-1}$; 0.15 s$^{-1}$; 0.25 s$^{-1}$; 0.3 s$^{-1}$; 0.5 s$^{-1}$).

The synthesis and biological activity of certain exemplary compounds is discussed in the following non-limiting examples.

Example 1

This Example shows the synthesis of the following compound

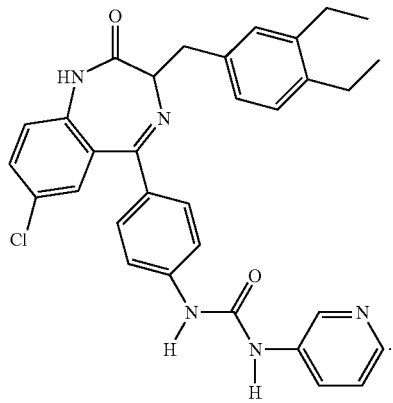

The compound was synthesized in accordance with the following reaction scheme.

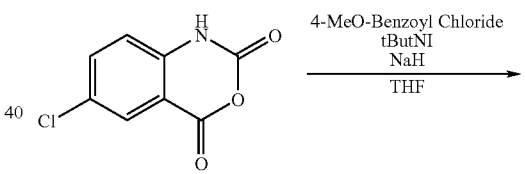

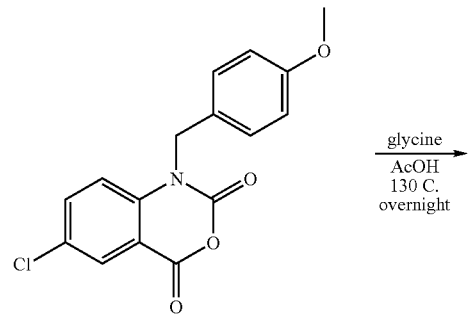

131
-continued
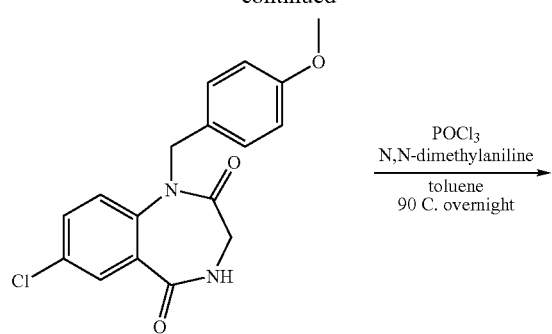
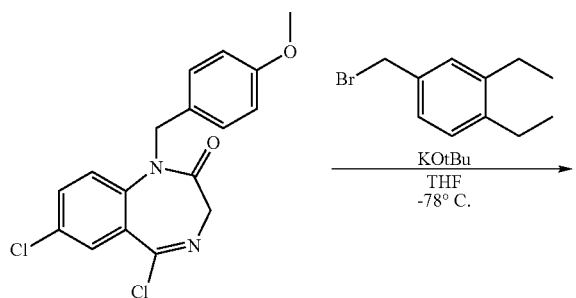
132
-continued
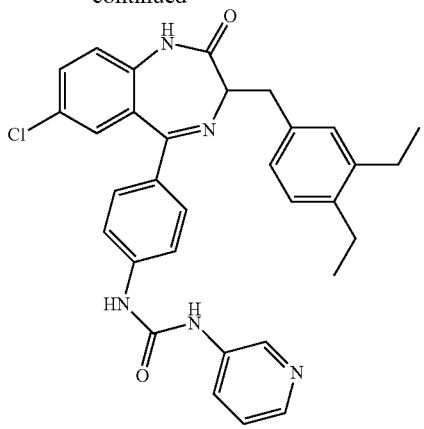
Example 2
It is contemplated that certain compounds of the invention could be made using the synthetic schemes shown below. Consistent with art-recognized terminology, the abbreviation "PMB-Cl" refers to 4-methoxybenzoyl chloride.
Scheme 1.
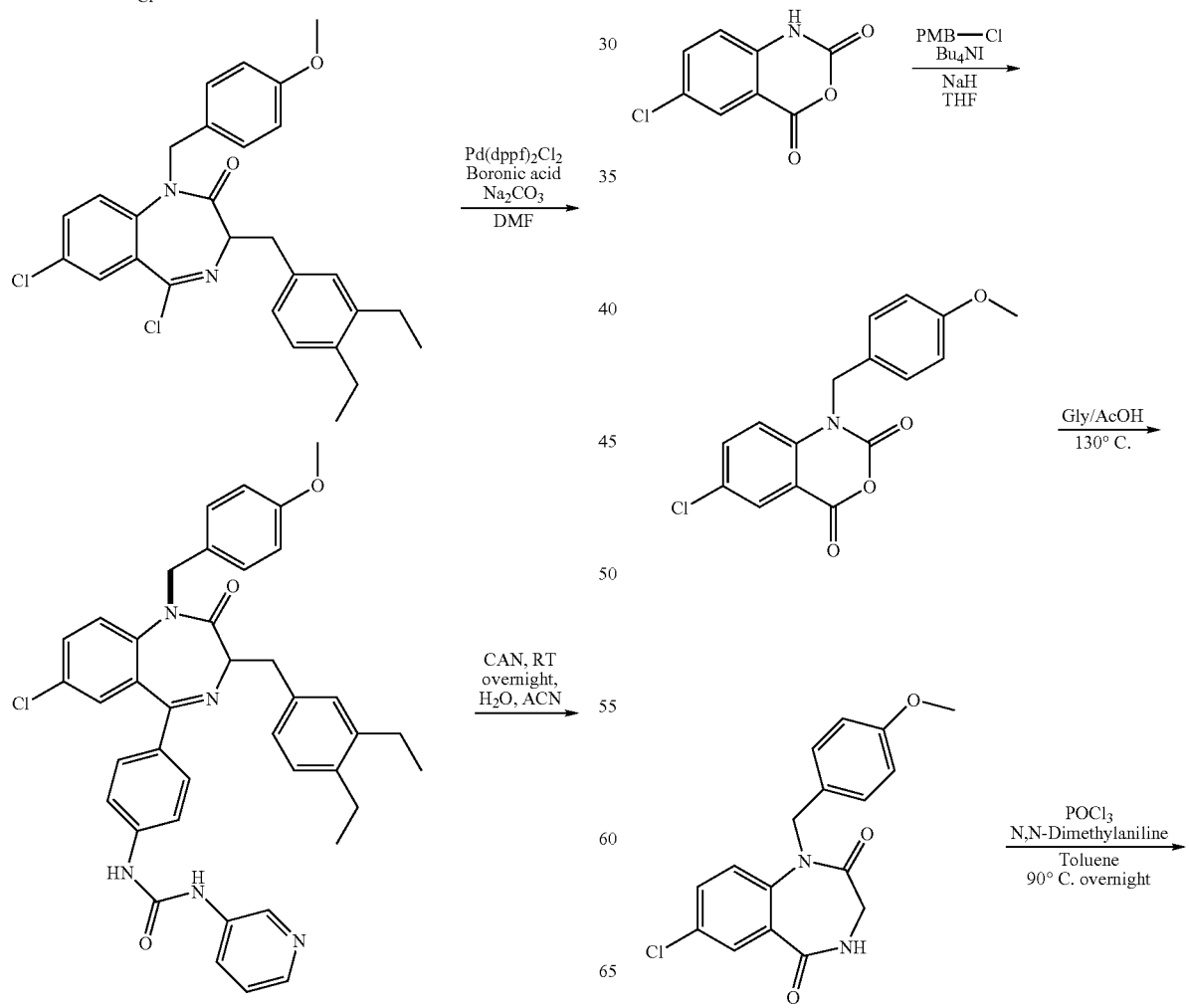

133 134
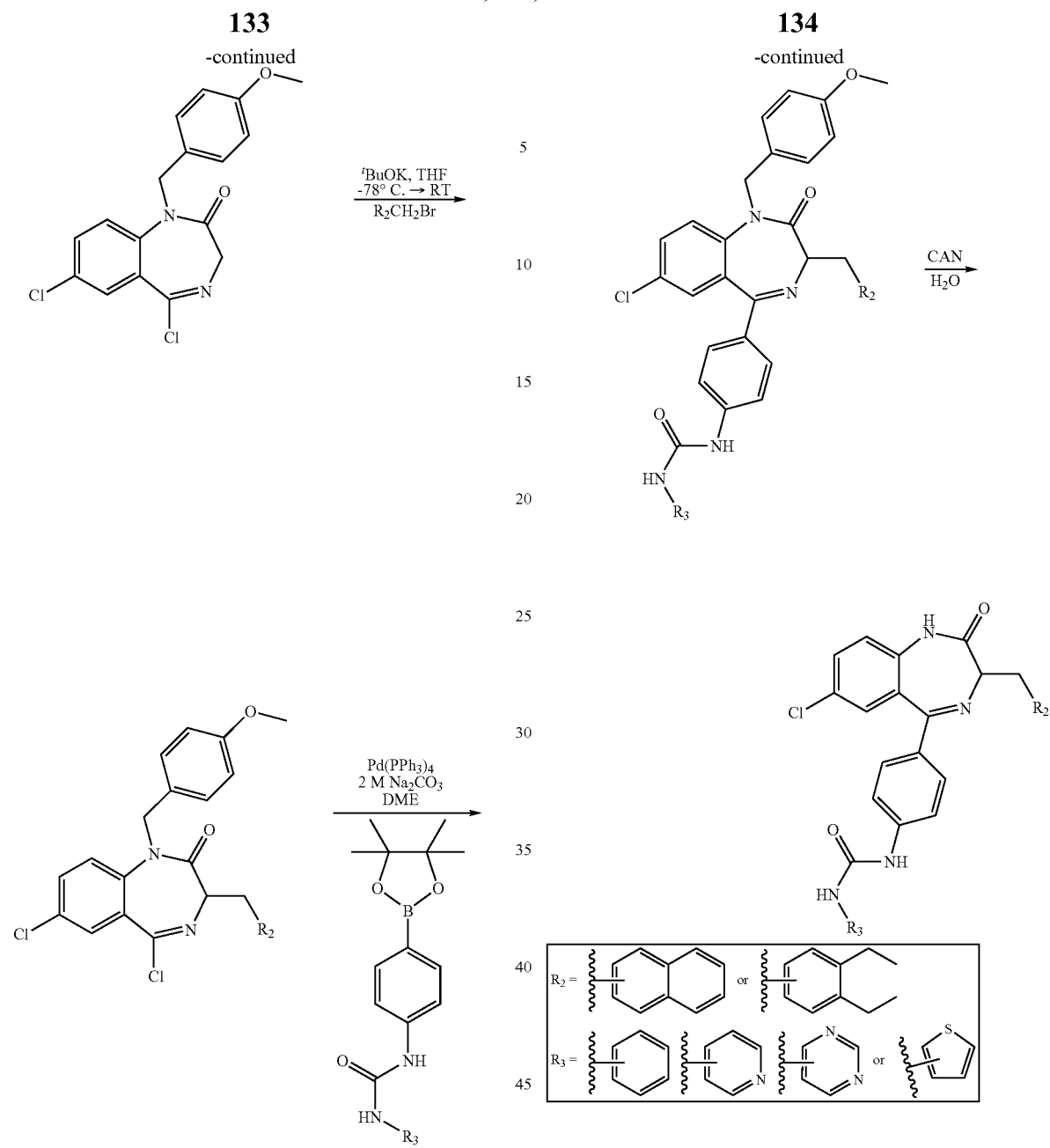
Scheme 2.
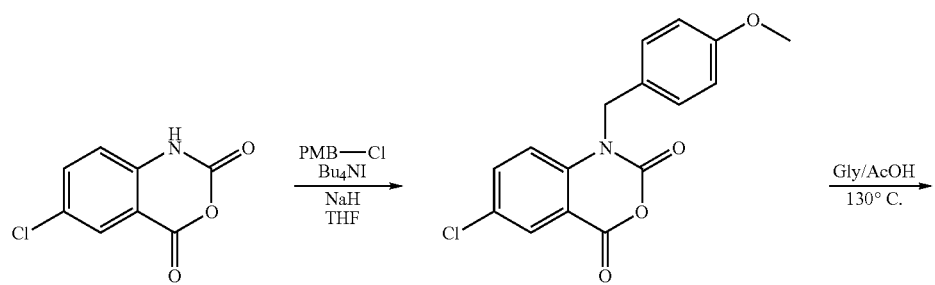

135
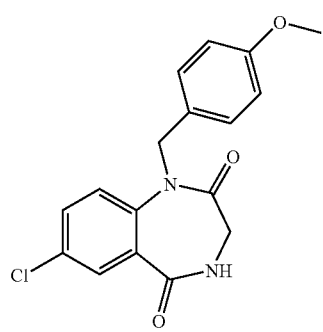
→ POCl₃
N,N-Dimethylaniline
Toluene
90° C. overnight
→
136
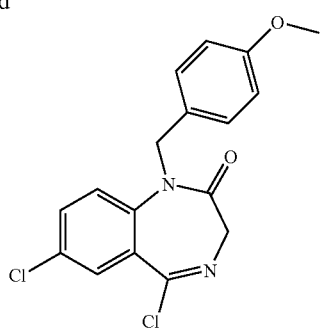
→ ᵗBuOK, THF
-78° C. → RT
R₂CH₂Br
→
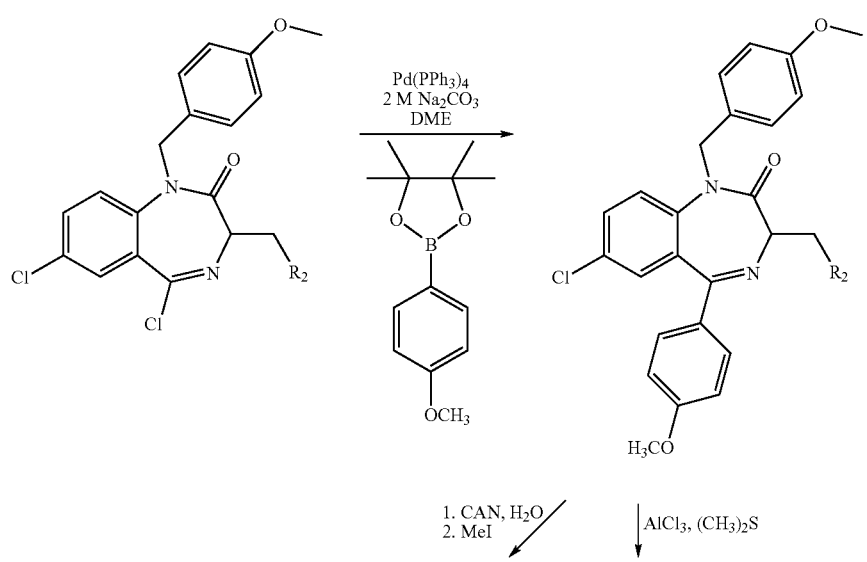
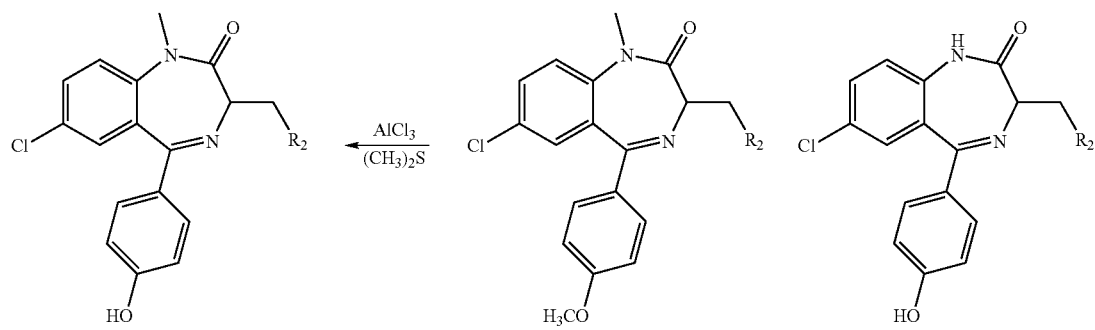
R₂ = naphthyl or optionally substituted phenyl

Example 3

The following compounds were assayed for their ability to cause apoptosis of Ramos B cells, based on the procedures described in Blatt et al. *J. Clin. Invest.* 110: 1123-1132 (2002). Each of the following compounds were found to have an $EC_{50} < 5$ µM.

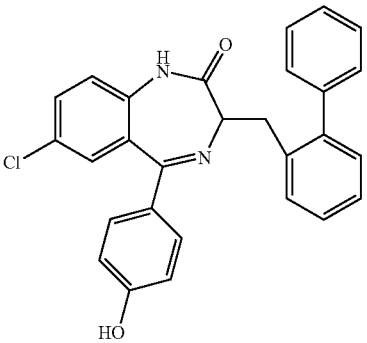

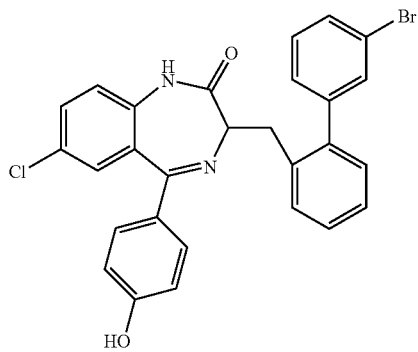

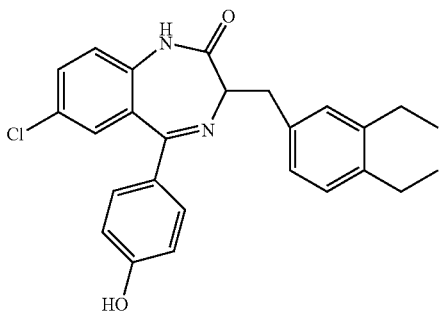

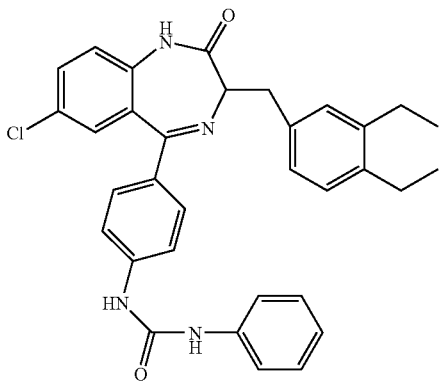

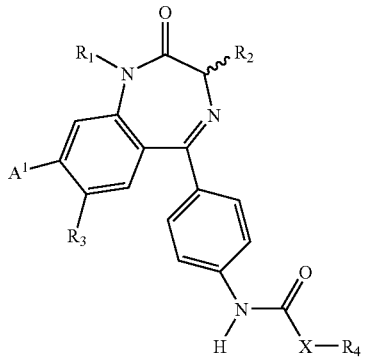

INCORPORATION BY REFERENCE

The entire disclosure of each of the publications and patent documents referred to herein is incorporated by reference in its entirety for all purposes to the same extent as if each individual publication or patent document were so individually denoted.

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein

I claim:

1. A compound represented by the following formula:

or an R-enantiomeric form, S-enantiomeric form, or racemic mixture thereof, or a pharmaceutically acceptable salt thereof;

wherein $A^1$ is H, Br, Cl, $NO_2$, or $CF_3$;

$R_1$ is $CH_3$ or H;

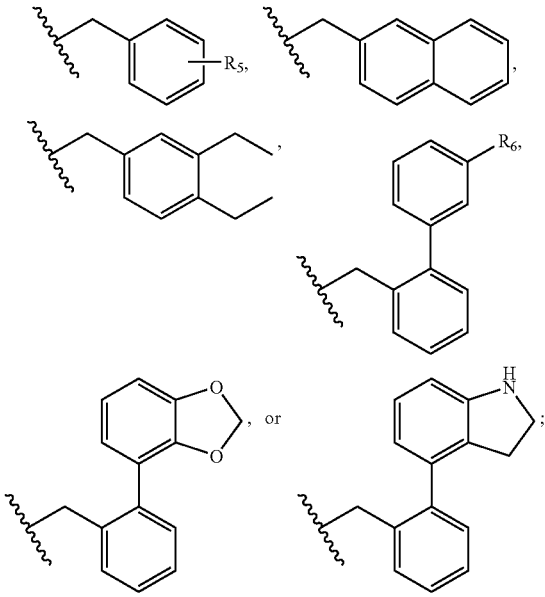

$R_3$ is H, Br, Cl, $NO_2$, or $CF_3$, $R_4$ is phenyl,

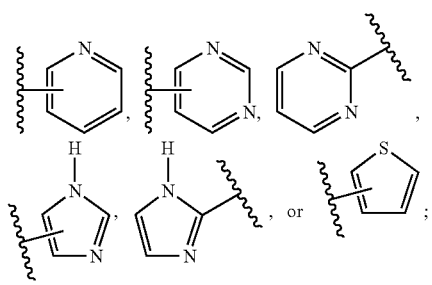

$R_5$ is $CH_3$, —$CH_2CH_3$, —$(CH_2)_2CH_3$, —$CH(CH_3)_2$, —$(CH_2)_3CH_3$, —$C(CH_3)_3$, phenyl, phenoxy, hydroxyphenyl, Br, F or Cl;

$R_6$ is H, Br, Cl, F, —$OCH_3$, or —$OCH(CH_3)_2$;

X is $CH_2$, or NH; and provided that at least one of $A^1$ and $R_3$ is not H.

2. The compound of claim 1, wherein $A^1$ is Cl or $NO_2$; and $R_3$ is H.

3. The compound of claim 1, wherein $A^1$ is H; and $R_3$ is Cl or $NO_2$.

4. The compound of claim 1, wherein $R_2$ is

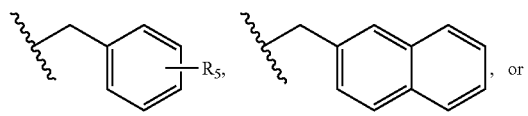, or

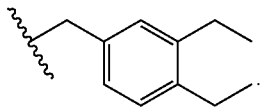.

5. The compound of claim 1, wherein X is $CH_2$.

6. The compound of claim 1, wherein X is NH.

7. The compound of claim 1, wherein $R_4$ is phenyl,

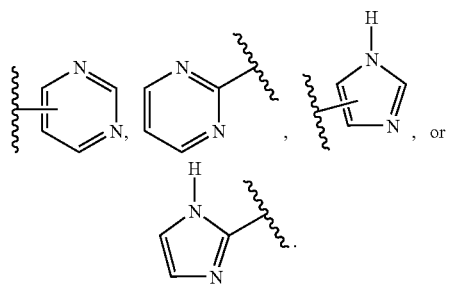

8. The compound of claim 1, wherein said compound is selected from the group consisting of:

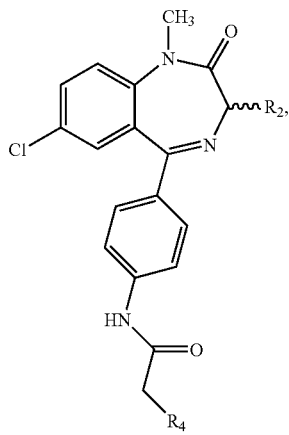

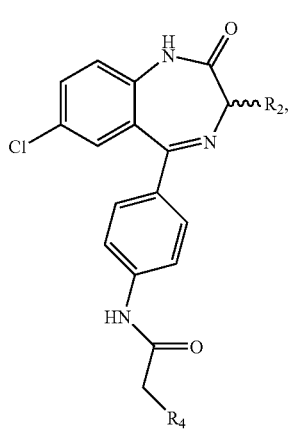

141
-continued
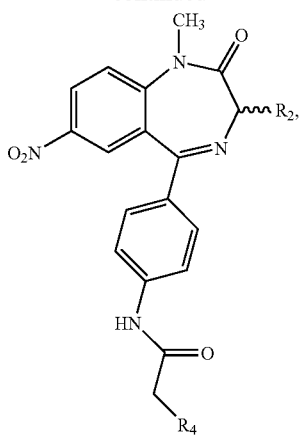
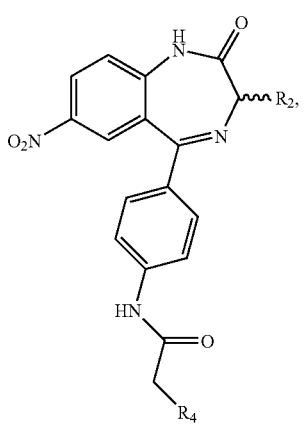
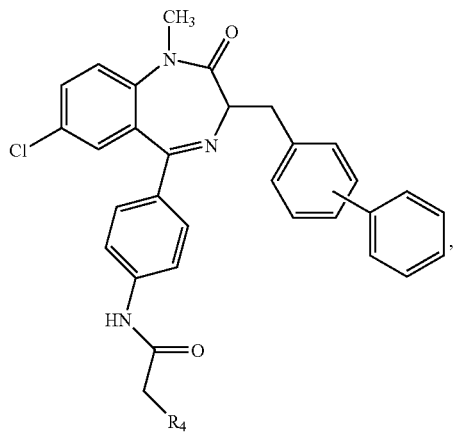
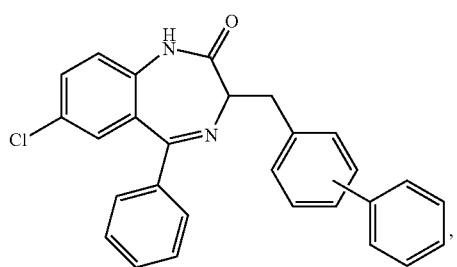
142
-continued
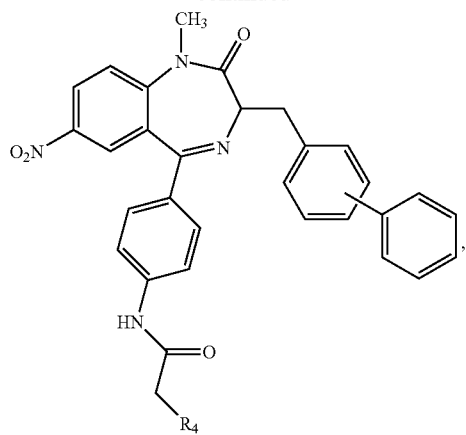
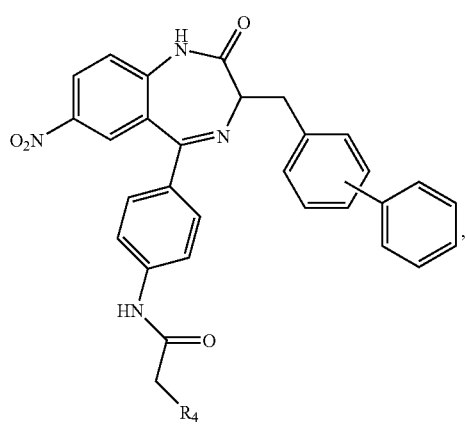
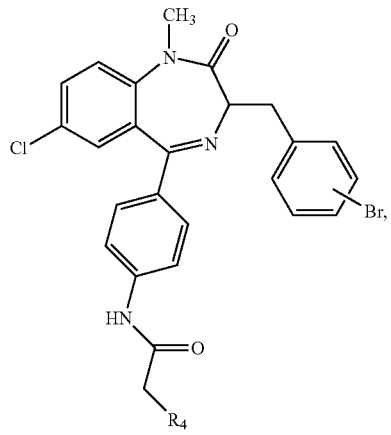
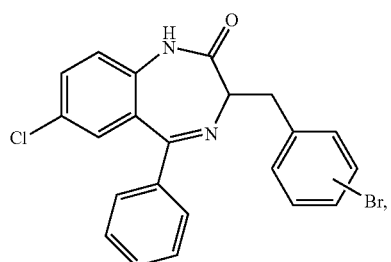

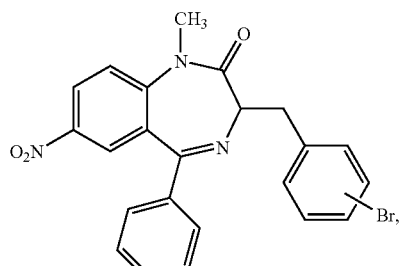
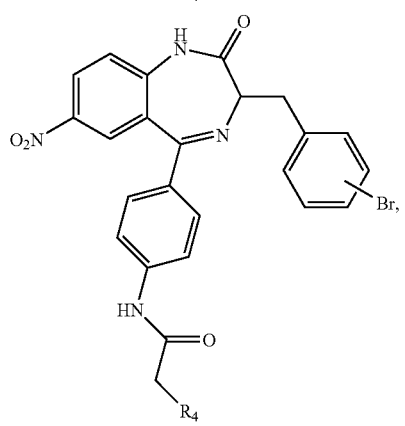
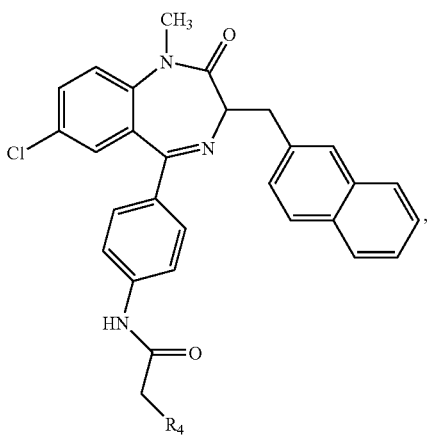
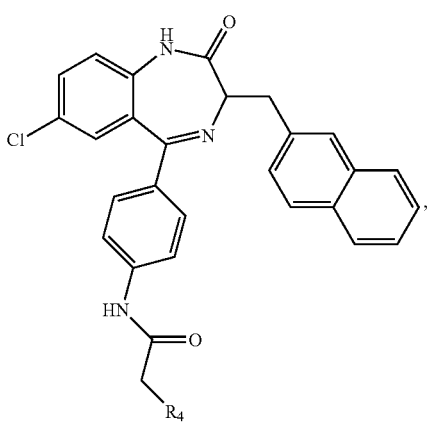
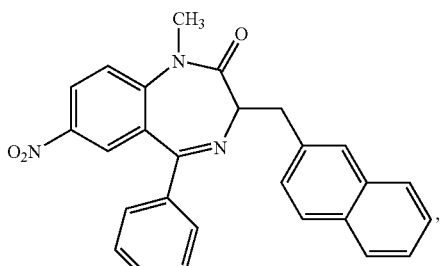
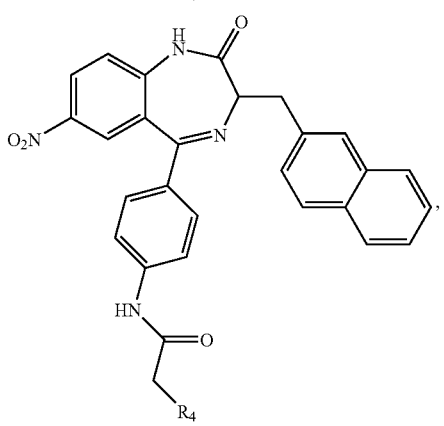
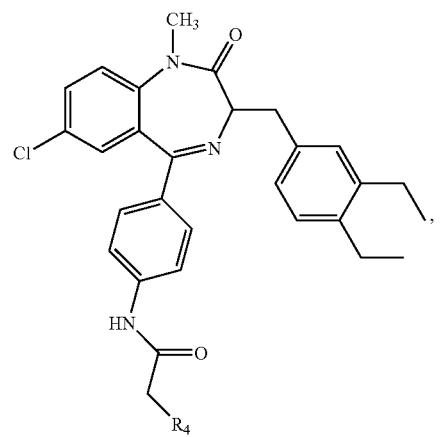
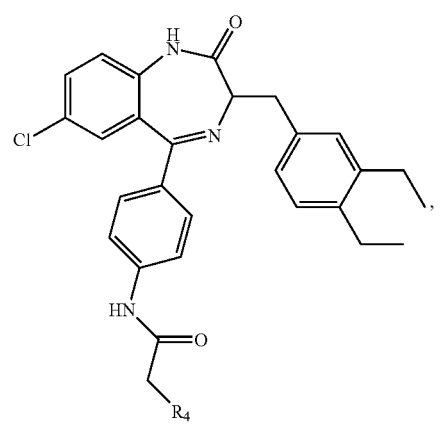

145
-continued
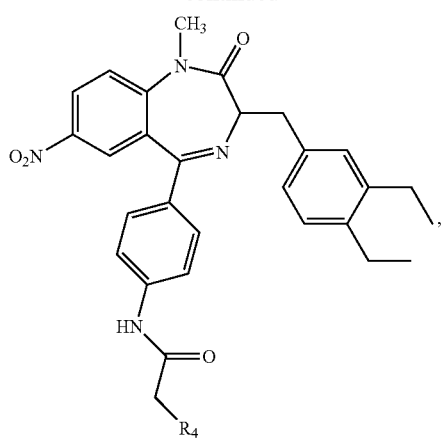
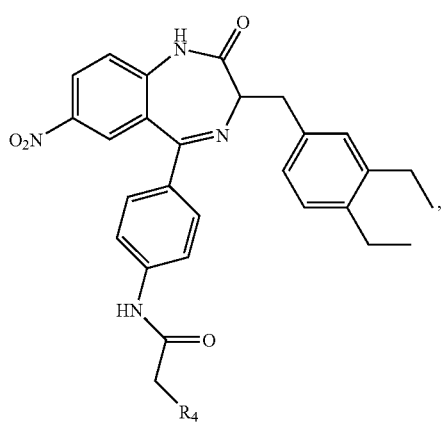
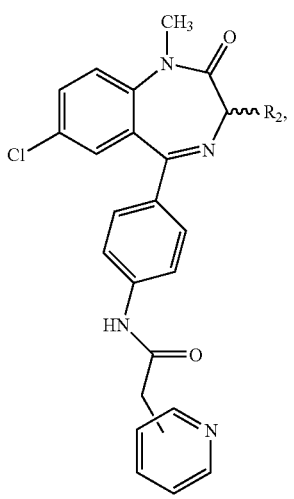
146
-continued
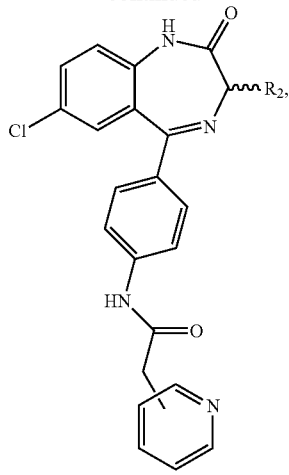
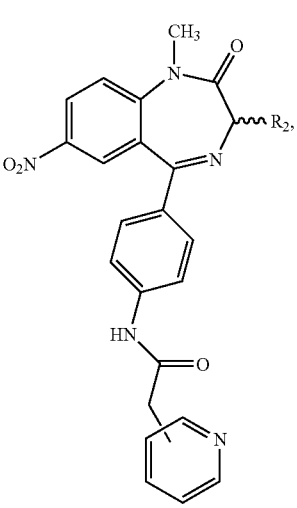
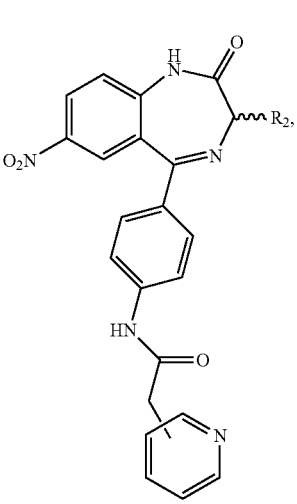

147
-continued
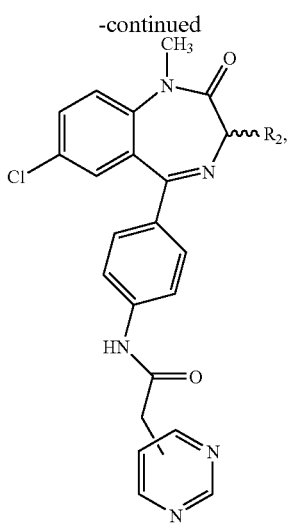
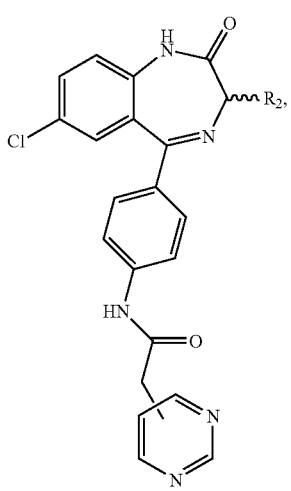
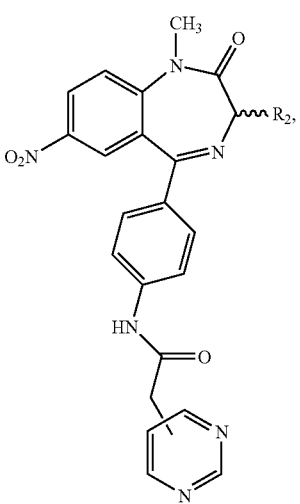
148
-continued
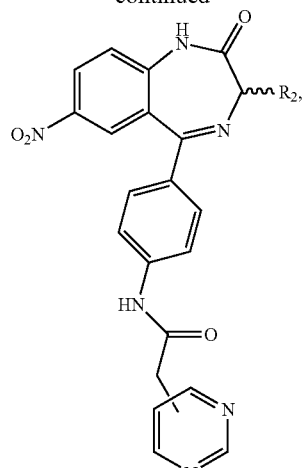
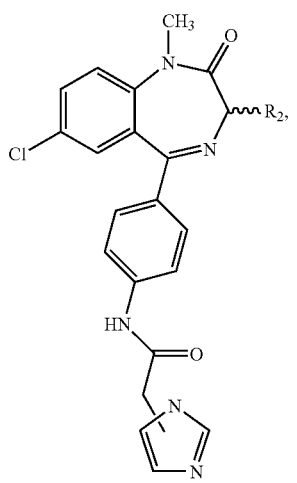
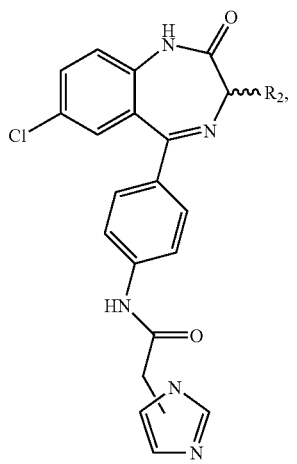

149 -continued | 150 -continued

151
-continued
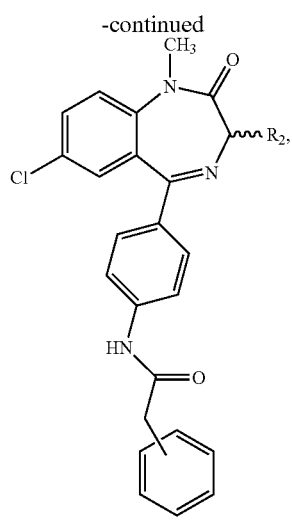
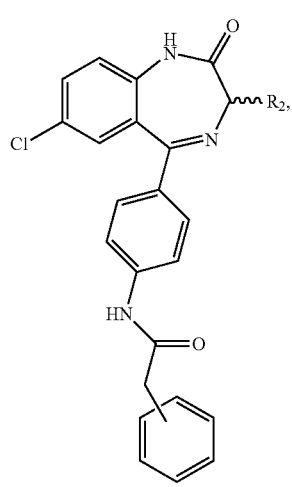
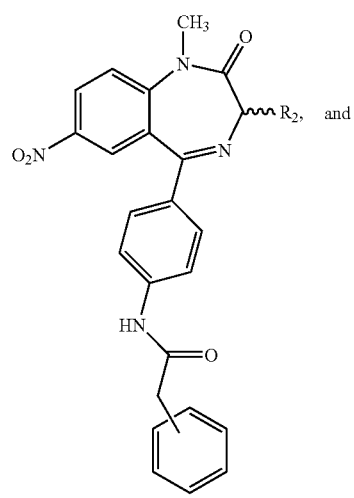
152
-continued
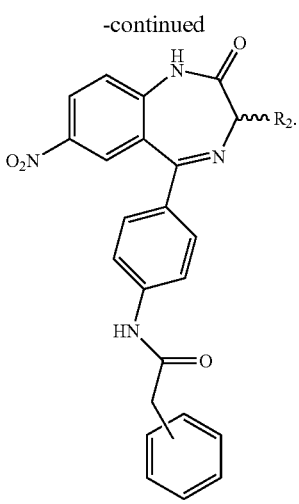
9. The compound of claim 1, wherein said compound is selected from the group consisting of:
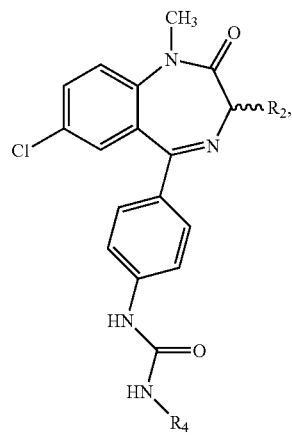
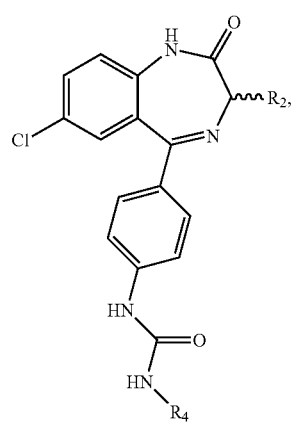

153
-continued
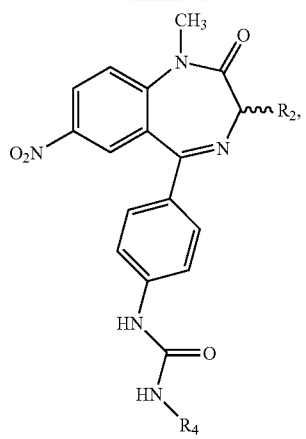
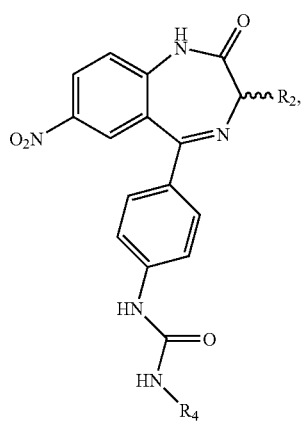
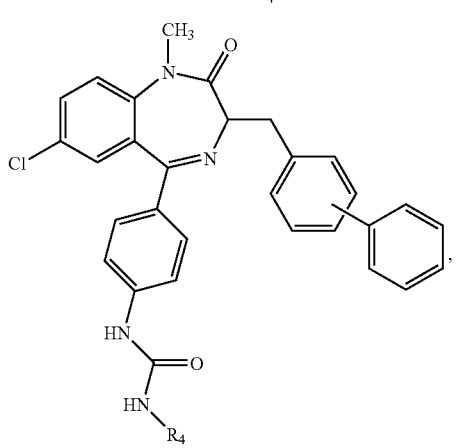
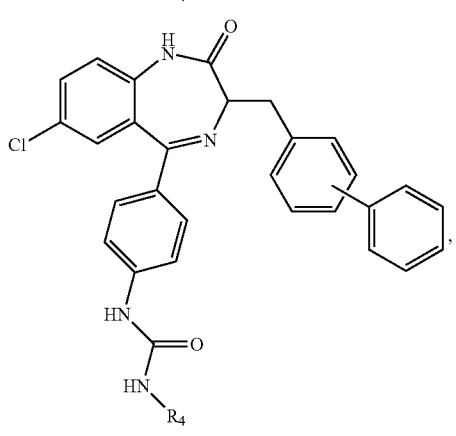
154
-continued
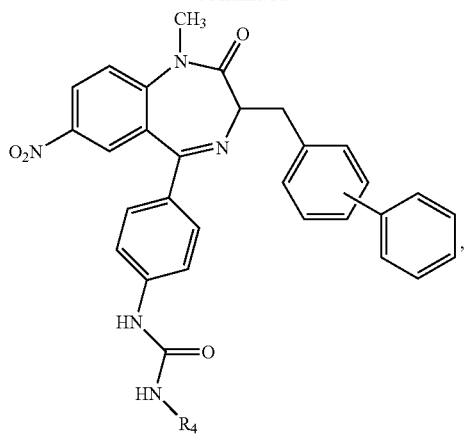
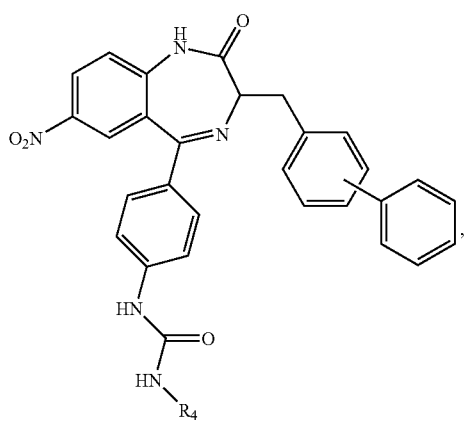
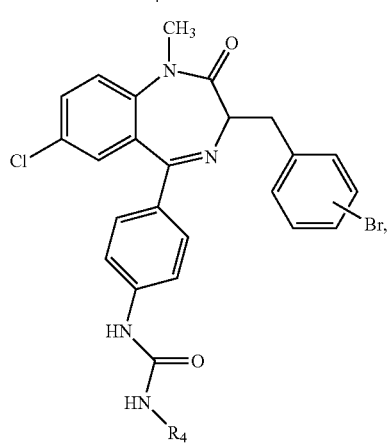
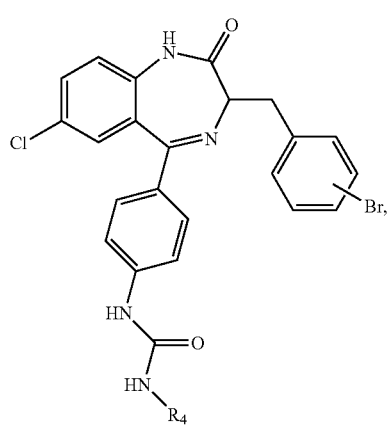

155
-continued
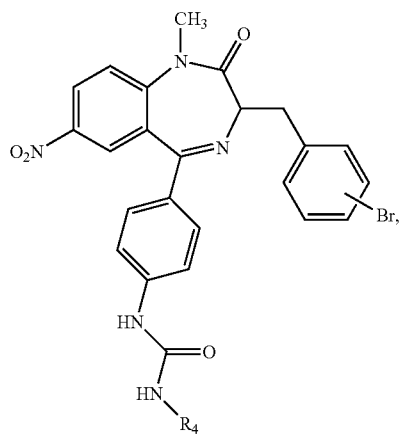
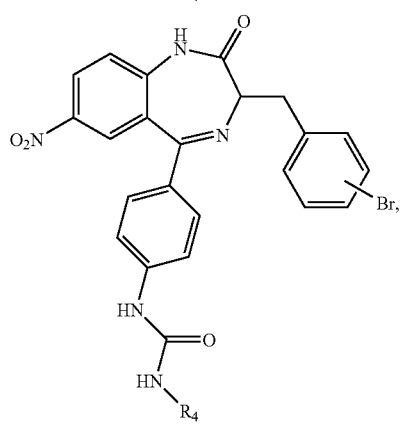
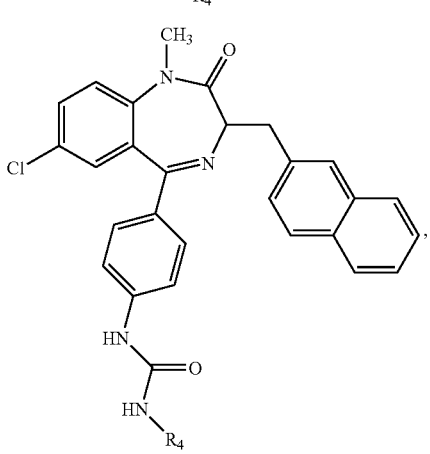
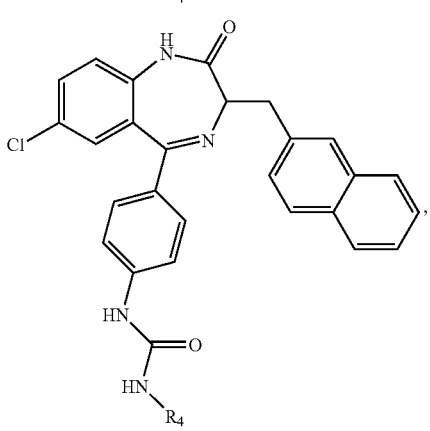
156
-continued
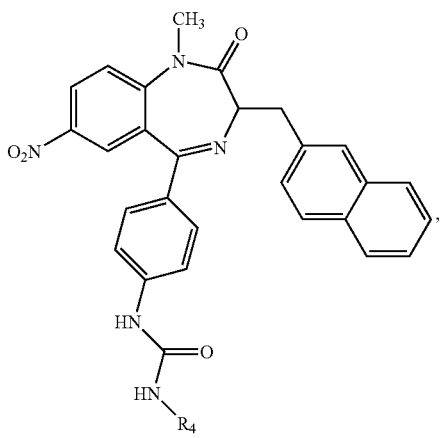
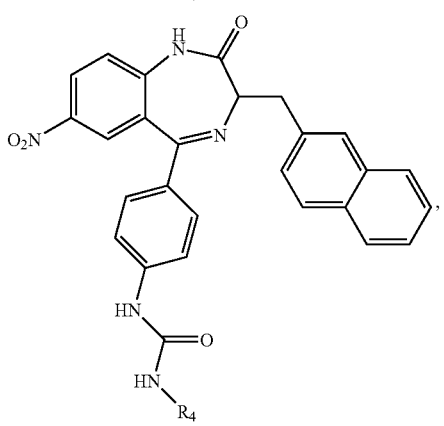
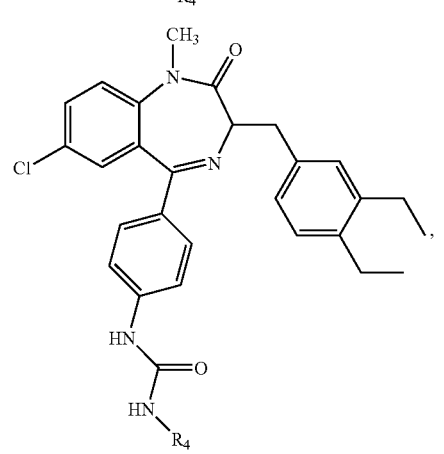
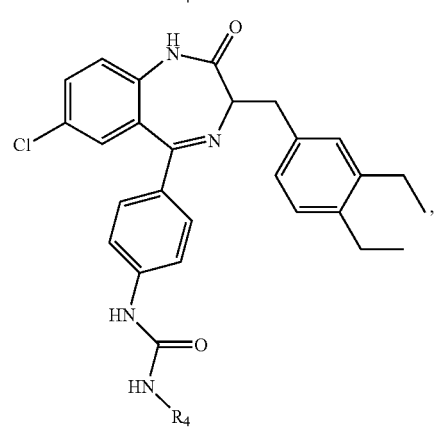

157
-continued
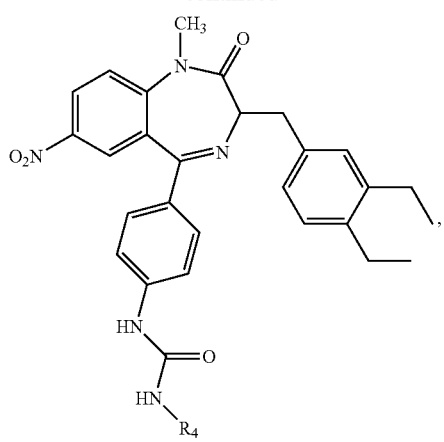
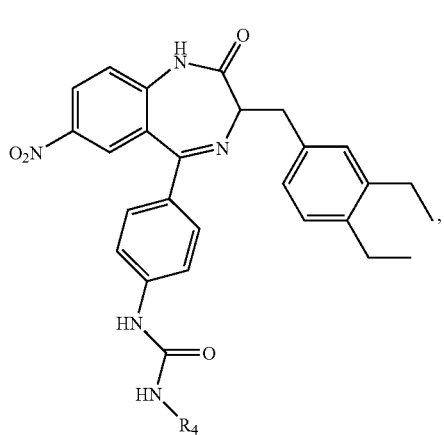
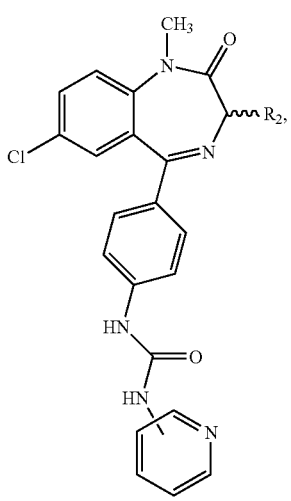
158
-continued
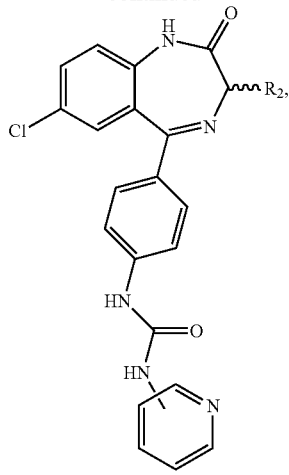
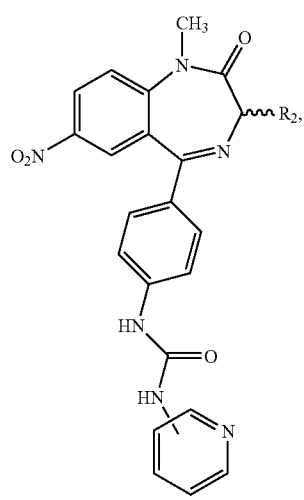
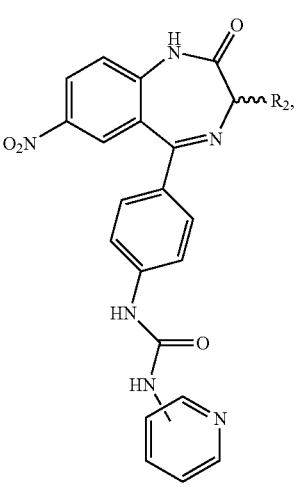

159 160

161
-continued
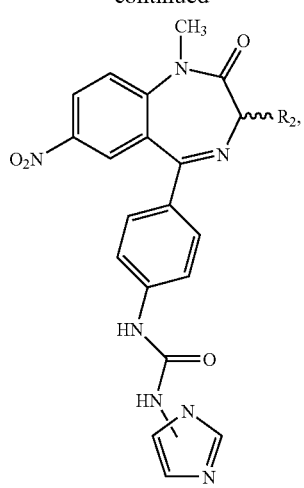
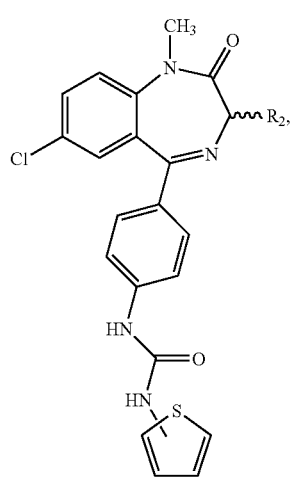
162
-continued
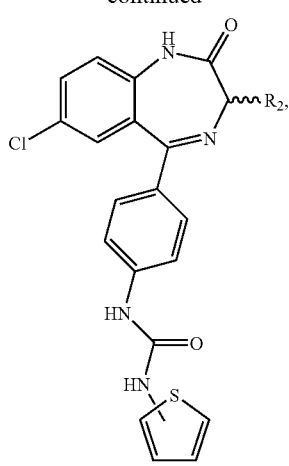
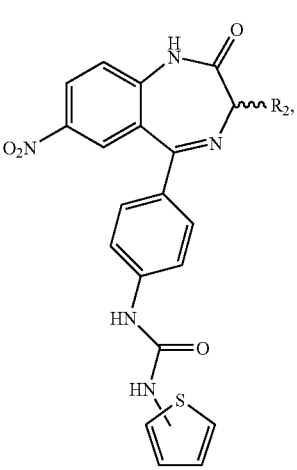

-continued
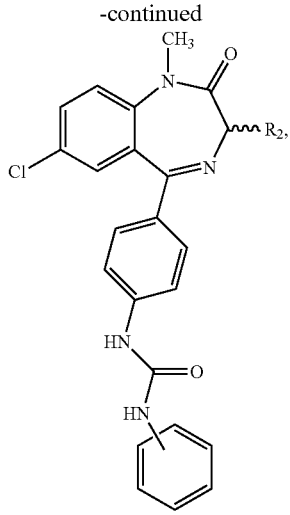
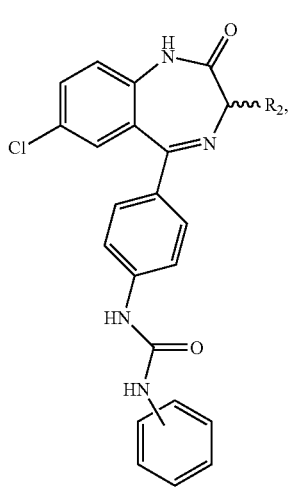
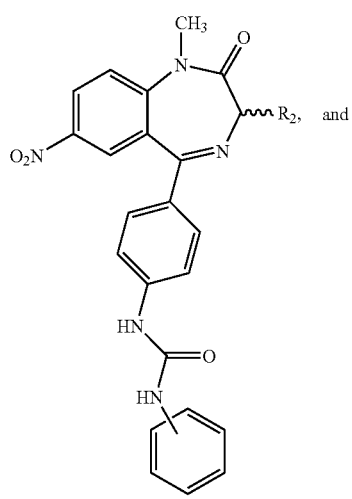 and
-continued
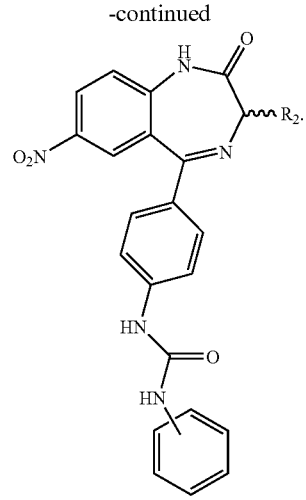
10. The compound of claim 1, wherein said compound is a compound listed in any one of Tables 1, 2, 3, or 4 presented herein.
11. A compound represented by the following formula:
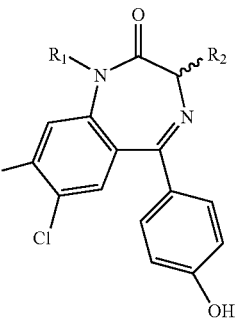
or an R-enantiomeric form, S-enantiomeric form, or racemic mixture thereof, or a pharmaceutically acceptable salt thereof;
wherein
$R_1$ is $CH_3$ or H;
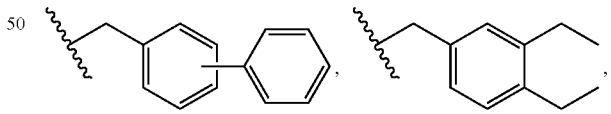
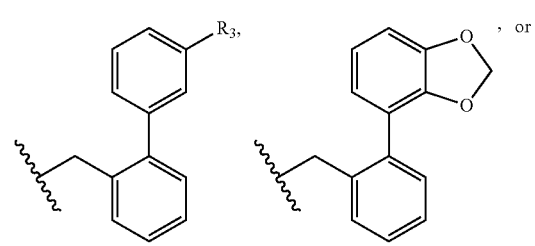

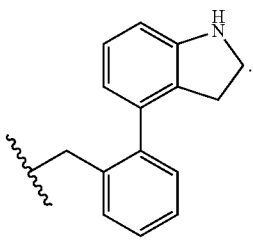
12. The compound of claim 11, wherein said compound is selected from the group consisting of:
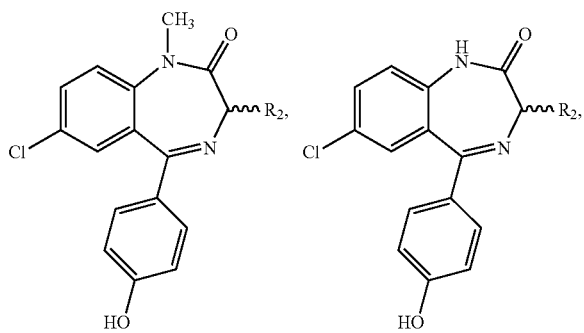
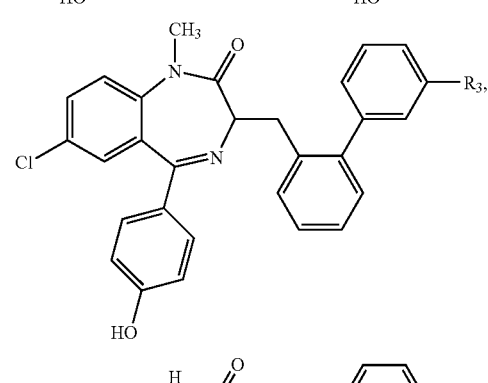
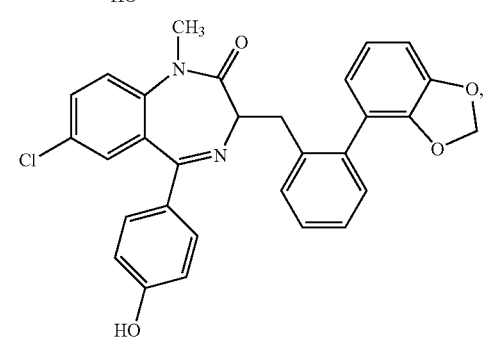
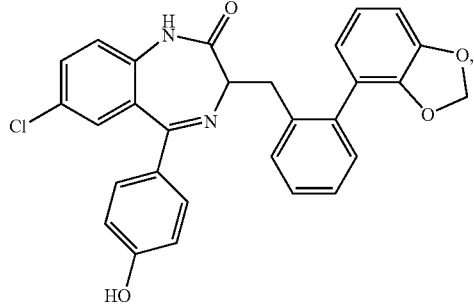
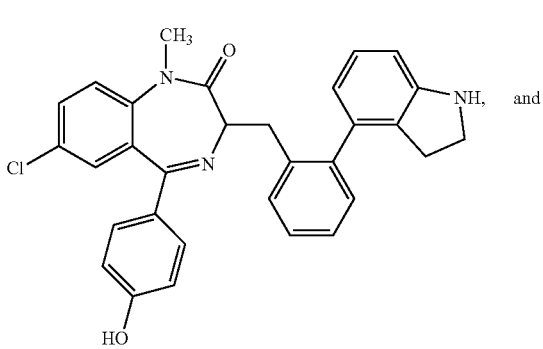
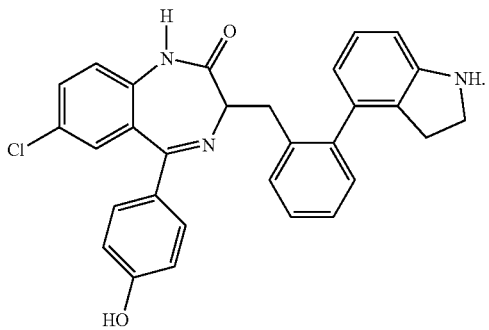
13. A compound represented by the following formula:
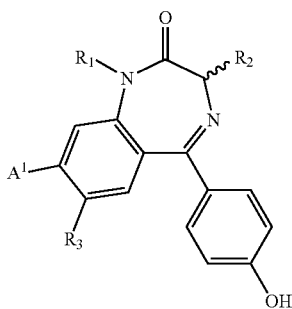
or an R-enantiomeric form, S-enantiomeric form, or racemic mixture thereof, or a pharmaceutically acceptable salt thereof;

wherein
A¹ is H or —NO₂;
R₁ is H or CH₃;
R₂ is
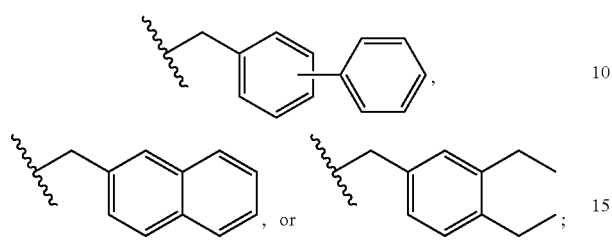
R₃ is H, —NO₂, or CF₃; and
provided that at least one of A¹ and R₃ is not H.
14. The compound of claim 13, wherein A¹ is H; and R₃ is —NO₂, or CF₃.
15. The compound of claim 13, wherein said compound is selected from the group consisting of:
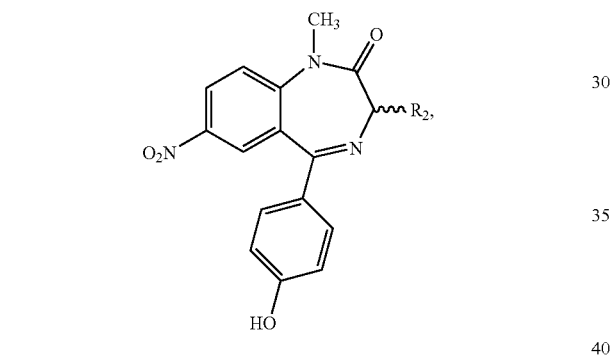
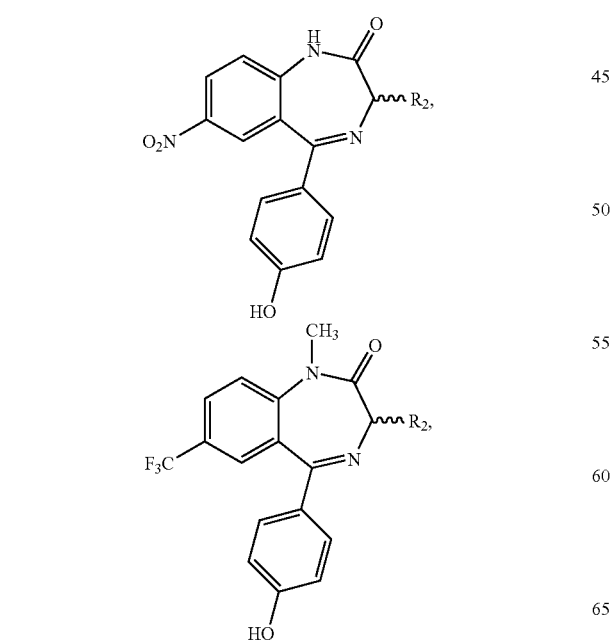
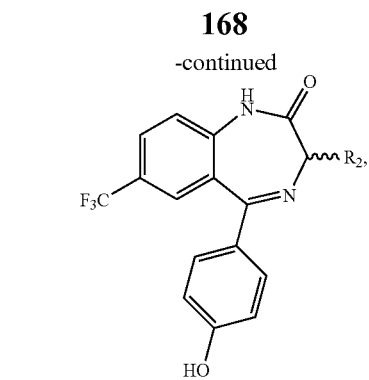
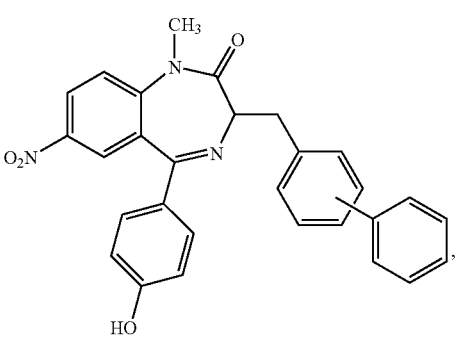
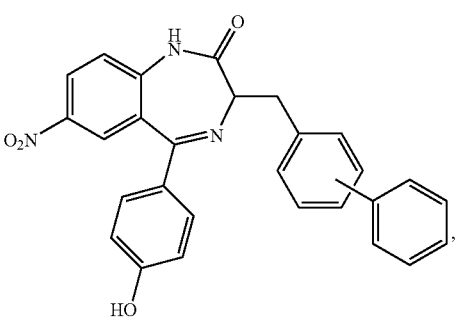
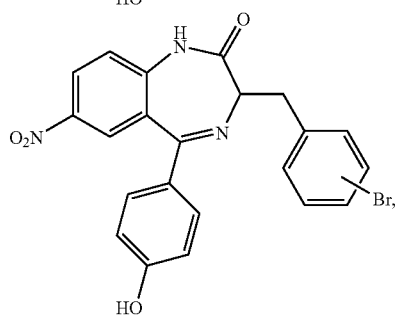

-continued
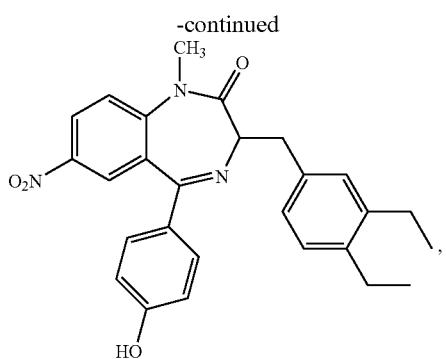
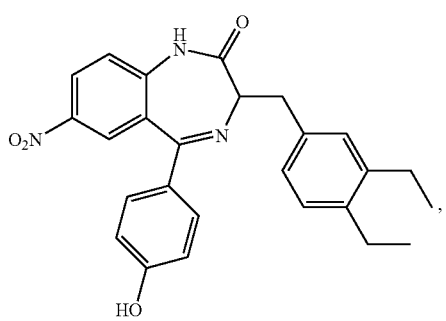
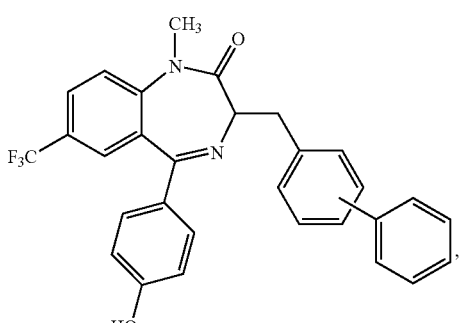
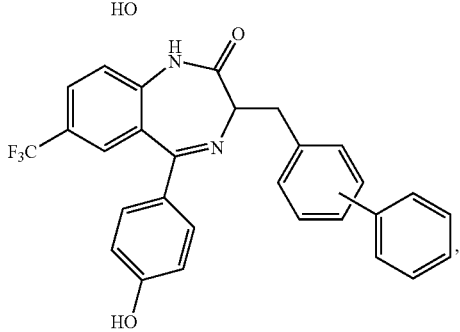
-continued
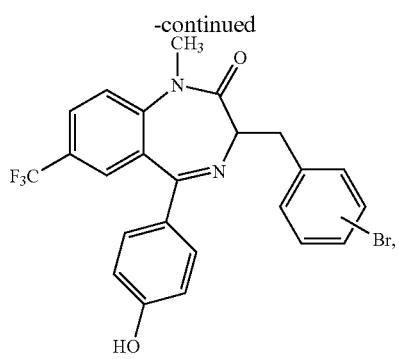
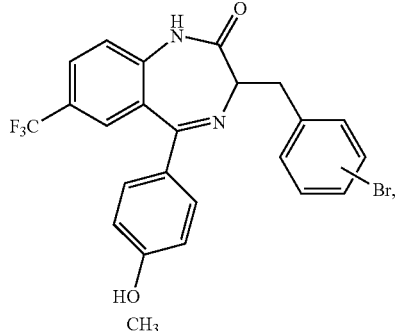
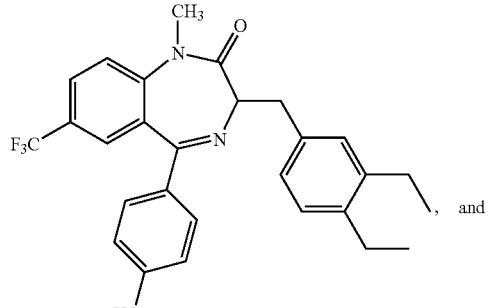, and
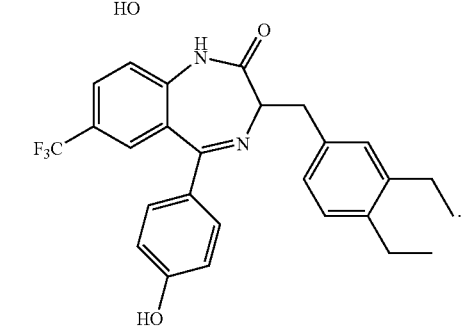.
16. A pharmaceutical composition comprising a compound of claim 1 and a pharmaceutically acceptable carrier.
* * * * *